(12) United States Patent
Brodney et al.

(10) Patent No.: US 9,045,498 B2
(45) Date of Patent: *Jun. 2, 2015

(54) HEXAHYDROPYRANO[3,4-D][1,3]THIAZIN-2-AMINE COMPOUNDS

(71) Applicant: Pfizer Inc., Groton, CT (US)

(72) Inventors: Michael Aaron Brodney, Newton, MA (US); Elizabeth Mary Beck, Cambridge, MA (US); Christopher Ryan Butler, Canton, MA (US); Jennifer Elizabeth Davoren, Cambridge, MA (US); Brian Thomas O'Neill, Haddam, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,409

(22) Filed: Jul. 8, 2014

(65) Prior Publication Data

US 2014/0323474 A1 Oct. 30, 2014

Related U.S. Application Data

(62) Division of application No. 14/101,462, filed on Dec. 10, 2013, now Pat. No. 8,822,456.

(60) Provisional application No. 61/895,623, filed on Oct. 25, 2013, provisional application No. 61/735,660, filed on Dec. 11, 2012.

(51) Int. Cl.
 *C07D 513/04* (2006.01)
 *A61K 31/542* (2006.01)

(52) U.S. Cl.
 CPC .................. *C07D 513/04* (2013.01)

(58) Field of Classification Search
 USPC .......................... 544/48; 514/224.2
 See application file for complete search history.

(56) References Cited

U.S. PATENT DOCUMENTS

| | | | |
|---|---|---|---|
| 5,750,349 A | 5/1998 | Suzuki et al. | |
| 7,115,600 B2 | 10/2006 | Wager et al. | |
| 7,285,293 B2 | 10/2007 | Castillo et al. | |
| 7,975,664 B2 | 7/2011 | Himsel et al. | |
| 8,158,620 B2 | 4/2012 | Suzuki et al. | |
| 8,278,441 B2 | 10/2012 | Mergott et al. | |
| 2003/0073655 A1 | 4/2003 | Chain | |
| 2003/0195205 A1 | 10/2003 | DeNinno et al. | |
| 2004/0192898 A1 | 9/2004 | Jia et al. | |
| 2004/0220186 A1 | 11/2004 | Bell et al. | |
| 2005/0019328 A1 | 1/2005 | Schenk et al. | |
| 2005/0043354 A1 | 2/2005 | Wager et al. | |
| 2005/0048049 A1 | 3/2005 | Schenk et al. | |
| 2005/0256135 A1 | 11/2005 | Lunn et al. | |
| 2005/0267009 A1 | 12/2005 | Bernardelli et al. | |
| 2005/0267100 A1 | 12/2005 | Elliott et al. | |
| 2006/0057701 A1 | 3/2006 | Rosenthal et al. | |
| 2006/0106035 A1 | 5/2006 | Hendrix et al. | |
| 2006/0111372 A1 | 5/2006 | Hendrix et al. | |
| 2006/0178501 A1 | 8/2006 | Summers et al. | |
| 2007/0031416 A1 | 2/2007 | Shoji et al. | |
| 2007/0160616 A1 | 7/2007 | Rosenthal et al. | |
| 2007/0179175 A1 | 8/2007 | Lunn | |
| 2008/0096955 A1 | 4/2008 | Wager et al. | |
| 2008/0176925 A1 | 7/2008 | Bulter et al. | |
| 2010/0056618 A1 | 3/2010 | Mascitti et al. | |
| 2010/0285145 A1 | 11/2010 | Darout et al. | |
| 2011/0027279 A1 | 2/2011 | Chain | |
| 2011/0038861 A1 | 2/2011 | Rosenthal | |
| 2011/0046122 A1 | 2/2011 | Andreini et al. | |
| 2011/0207723 A1 | 8/2011 | Motoki et al. | |
| 2012/0245155 A1 | 9/2012 | Yoshida et al. | |
| 2013/0296308 A1 | 11/2013 | Brodney et al. | |

FOREIGN PATENT DOCUMENTS

| | | |
|---|---|---|
| EP | 0994728 | 10/1998 |
| EP | 1257584 | 10/2004 |
| EP | 2332943 | 6/2011 |
| EP | 2511269 | 10/2012 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 6/2005 |

(Continued)

OTHER PUBLICATIONS

Haan, J., et al., "Amyloid in Central Nervous System Disease", Clinical Neurology and Neurosurgery, 1990, pp. 305-310, 92(4).
Glenner, G., et al., "Amyloidosis of the Nervous System", Journal of Neurological Science, Dec. 1989, pp. 1-28, vol. 94.

(Continued)

*Primary Examiner* — Kahsay Habte
(74) *Attorney, Agent, or Firm* — John A. Wichtowski

(57) ABSTRACT

The present invention provides compounds of Formula I, and the tautomers thereof, and the pharmaceutically acceptable salts of the compounds and tautomers, wherein the compounds have the structure

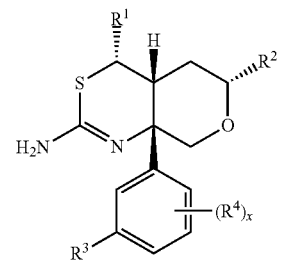

wherein the variables $R^1$, $R^2$, $R^3$, $R^4$ and x are as defined in the specification. Corresponding pharmaceutical compositions, methods of treatment, methods of synthesis, and intermediates are also disclosed.

17 Claims, No Drawings

(56) References Cited

FOREIGN PATENT DOCUMENTS

| | | |
|---|---|---|
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011071109 | 6/2011 |
| WO | 2012098461 | 7/2012 |
| WO | 2013030713 | 3/2013 |
| WO | 2013164730 | 11/2013 |

OTHER PUBLICATIONS

Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).

Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).

Esterhazy, Daria, et al., "BACE2 Is a β Cell-Enriched Protease that Regulates Pancreatic β Cell Function and Mass", Cell Metabolism, Sep. 2011, pp. 365-377, 14(3).

Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).

Alberti, K.G. et al., "The Metabolic Syndrome—A New Worldwide Definition," Lancet, Sep. 24-30, 2005, pp. 1059-1062, 366(9491).

Haleblian, John K., "Characterization of Habits and Crystalline Modification of Solids and Their Pharmaceutical Applications", Journal Pharmaceutical Sciences, Aug. 1975, pp. 1269-1288, 64(8).

Finnin, Barrie, et al., "Transdermal Penetration Enhancers" Applications, Limitations, and Potential, Journal Pharmaceutical Sciences, Oct. 1999, pp. 955-958, 88(10).

Zhang, S. et al., "PTP1B as a Drug Target: Recent Developments in PTP1B Inhibitor Discovery", Drug Discovery Today, May 2007, pp. 373-381, 12(9/10).

Chao, Edward, et al., "SGLT2 Inhibition—A Novel Strategy for Diabetes Treatment", Nature Reviews Drug Discovery, Jul. 2010, pp. 551-559, 9(7).

Demong, D.E. et al., "Chapter 8, Glucagon Receptor Antagonists for Type II Diabetes", Annual Reports in Medicinal Chemistry 2008, pp. 119-137, vol. 43.

Jones, R.M. et al., "Chapter 7, The Emergence of GPR119 Agonists as Anti-Diabetic Agents", Annual Reports in Medicinal Chemistry 2009, pp. 149-170, vol. 44.

Zhong, M., "TGR5 as a Therapeutic Target for Treating Obesity", Current Topics in Medicinal Chemistry, 2010, pp. 386-396, 10(4).

Medina, J.C., et al., "Chapter 5, GPR40 (FFAR1) Modulators", Annual Reports in Medicinal Chemistry 2008, pp. 75-85, vol. 43.

Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).

Spek, A.L., "Single-Crystal Structure Validation with the Program PLATON", Journal of Applied Crystallography, Feb. 2003, pp. 7-13, 36(1).

Macrae, Clare, et al., "Mercury: Visualization and Analysis of Crystal Structures", Journal of Applied Crystallography, Jun. 2006, pp. 453-457, 39(3).

Hooft, Rob, et al., "Determination of Absolute Structure Using Bayesian Statistics on Bijvoet differences", Journal of Applied Crystallography, Feb. 2008, , pp. 96-103, 41(1).

Flack, H.D., ", On Enantiomorph-Polarity Estimation", Acta Cryst., 1983, pp. 876-881, vol. A39.

England, et al., "An Improved Synthesis of a Novel α1A Partial Agonist Including A New Two-Step Synthesis of 4-Fluoropyrazole", Tetrahedron Letters, May 26, 2010, pp. 2849-2851, 51(21).

Kharitonenkov, A. et al., "FGF21: A Novel Prospect for the Treatment of Metabolic Diseases", Current Opinion in Investigational Drugs, Apr. 2009, pp. 359-364, 10(4).

Denmark, S.E., et al., "Allylation of Carbonyls: Methodology and Stereochemistry", Modern Carbonyl Chemistry, 2000, Chapter 10, pp. 299-401.

Miyaura, N., et al., "Palladium-Catalyzed Cross-Coupling Reactions of Organoborn Compounds", Chemical Review, Nov. 1995, pp. 2457-2483, 95(7).

Olsen, R., et al., "Secretase Inhibitors and Modulators for the Treatment of Alzheimer's Disease", Annual Reports In Medicinal Chemistry, 2007, pp. 27-47, vol. 42.

International Application No. PCT/IB2012/054198, filed Aug. 17, 2012, International Search Report and Written Opinion, mailed Jan. 23, 2013, 14 pages.

Sheppeck, J.E. II, et al., "A Convenient and Scaleable Procedure for Removing the Fmoc Group in Solution", Tetrahedron Letters, 2000, pp. 5329-5333, vol. 41(28).

Suzuki, Akira, "Recent advances in the cross-coupling reactions of organoboron derivatives with organic electrophiles 1995-1998", Journal Organometallic Chemistry, 1999, pp. 147-168, vol. 576.

International Application No. PCT/IB2013/053178, filed Apr. 22, 2013, International Written Opinion and Search Report, mailed Jul. 3, 2013, 10 pages.

English equivalent US Patent US 8,158,620; Suzuki, et al., filed Jan. 16, 2009 for WO 2009091016, published Jun. 23, 2007.

International Application No. PCT/IB2013/058402, filed Sep. 9, 2013, International Search Report, mailed Dec. 16, 2013, 11 pages.

International Application No. PCT/IB2013/060456, filed Nov. 27, 2013, International Search Report, mailed Feb. 21, 2014, 8 pages.

PCT/IB2013/060633 application filed Dec. 4, 2013.
PCT/IB2013/058402 application filed Sep. 9, 2013.
PCT/IB2013/060456 application filed Nov. 27, 2013.
PCT/IB2014/058760 application filed Feb. 3, 2014.
PCT/IB2014/058777 application filed Feb. 4, 2014.

Guidance for Industry, Q3C—Tables and List, U.S. Department of Health and Human Services, Food and Drug Administration, Center for Drug Evaluation and Research (CDER), Center for Biologics Evaluation and Research (CBER), Nov. 2003, ICH, Revision I.

HEXAHYDROPYRANO[3,4-*D*][1,3]THIAZIN-2-AMINE COMPOUNDS

This application is a Divisional Application of U.S. patent application Ser. No. 14/101,462, filed on Dec. 10, 2013, which claims the benefit of U.S. Provisional Patent Application No. 61/895,623 filed on Oct. 25, 2013 and U.S. Provisional Patent Application No. 61/735,660 filed on Dec. 11, 2012, the disclosures of which are hereby incorporated by reference in its entirety.

FIELD OF THE INVENTION

The present invention relates to small molecule inhibitors of β-site amyloid precursor protein (APP) Cleaving Enzyme 1 (BACE1). In particular, this invention relates to inhibiting the production of A-beta peptides that can contribute to the formation of neurological deposits of amyloid protein, which may be applicable in the treatment of Alzheimer's Disease (AD) and other neurodegenerative and/or neurological disorders in mammals. In addition, this invention is related to the treatment of diabetes and obesity in mammals, including humans.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4): 305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's Disease (AD), which is the most common cause of cognitive decline in the elderly (Hardy & Allsop, Trends Pharmacol Sci., 1991; 12(10):383-8; Selkoe, Behav. Brain Res., 2008; 192(1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane bound C99 fragment by the γ-secretase liberates the various Aβ peptide species, of which Aβ40 and Aβ42 are the most predominant forms (Vassar et al, J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 Diabetes (de la Monte, J. Diabetes Sci. Technol., 2008; 2(6):1101-1113). Of special interest is the fact that AD and Type 2 diabetes share common pathogenic mechanisms and possibly treatments (Park SA., J. Clin. Neurol., 2011; 7:10-18; Raffa, Br. J. Clin. Pharmacol 2011/71:3/365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients. (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. PCT application, PCT/IB2012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

The present invention relates to:
(1) A compound of Formula I,

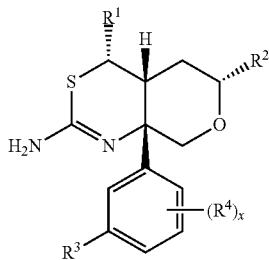

I wherein
$R^1$ is hydrogen or methyl, wherein said methyl is optionally substituted with one to three substituents independently selected from halogen or methoxy;
$R^2$ is $C_{1-6}$ alkyl, —$(C(R^5)_2)_m$—$(C_{3-6}$ cycloalkyl), —$(C(R^5)_2)_m$—, —$(C_{6-10}$ aryl), —$(C(R^5)_2)_m$—(5- to 10-membered heteroaryl) or —$(C(R^5)_2)_t$—$OR^6$; wherein said alkyl, cycloalkyl, aryl or heteroaryl moieties are optionally substituted with one to three substituents independently selected from halogen, $C_{1-6}$ alkyl, —$CH_2F$, —$CHF_2$, —$CF_3$, —CN or —$OR^7$;
$R^3$ is —$(C(R^5)_2)_m$—, —(CN) or —$(C(R^5)_2)_n$—$(NHR^7)$;
$R^4$ is independently halogen, $C_{1-6}$ alkyl or $C_{1-6}$ alkoxy; wherein said alkyl or alkoxy is optionally substituted with one to three fluoro;
$R^5$ at each occurrence is independently hydrogen or $C_{1-3}$ alkyl, wherein said alkyl is optionally substituted with one to three halogen;
$R^6$ is hydrogen, $C_{1-6}$ alkyl or —$(C(R^6)_2)_n$—$(C_{6-10}$ aryl), wherein said alkyl and aryl are optionally substituted with one to three substituents independently selected from halogen, $C_{1-3}$ alkyl, —$CH_2F$, —$CHF_2$, —$CF_3$, —CN or —OH;
$R^7$ for each occurrence is hydrogen or $C_{1-6}$ alkyl, wherein said alkyl is optionally substituted with one to three substituents independently selected from halogen or —$C_{1-6}$ alkoxy;
m for each occurrence is 0, 1 or 2;
n for each occurrence is 1 or 2; and
t is 1 or 2; and
x is 0, 1, 2 or 3;
or a tautomer thereof or a pharmaceutically acceptable salt of said compound or tautomer.
(2) A pharmaceutical composition comprising a compound of the invention, or a tautomer thereof or a pharmaceutically acceptable salt of said compound or tautomer, or a solvate thereof, and a pharmaceutically acceptable vehicle, diluent or carrier;
(3) The pharmaceutical composition described herein for inhibiting production of amyloid-β protein and for inhibiting beta-site amyloid precursor protein cleaving enzyme 1 (BACE1);
(4) The pharmaceutical composition described herein for treating a neurodegenerative disease and, in particular, Alzheimer's Disease;
(5) The pharmaceutical composition described herein for inhibiting BACE activity for the therapeutic and/or prophylactic treatment of diseases and disorders characterized by elevated β-amyloid levels, including diabetes or type 2 diabetes;
(6) The pharmaceutical composition described herein for increasing insulin sensitivity in skeletal muscle and liver in a mammal, including humans;
(7) The pharmaceutical composition described herein for treating and/or preventing obesity.
(8) A compound or tautomer thereof or pharmaceutically acceptable salt of said compound or tautomer, or the solvate thereof, wherein the compound is selected from Examples 1-20, further described in Table 1;
(9) Methods of inhibiting BACE enzyme activity, by administering a therapeutically effective amount of a thioamidine compound of any of the embodiments of Formula I or a pharmaceutically acceptable salt thereof, and a pharmaceutically acceptable carrier, to a mammal or a patient in need thereof.
(10) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/ hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(11) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(12) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(13) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005);

(14) Methods for the treatment of nonalcoholic fatty liver disease (NAFLD) and hepatic insulin resistance;

(15) Combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendent claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

The term "alkyl" refers to a linear or branched-chain saturated hydrocarbyl substituent (i.e., a substituent obtained from a hydrocarbon by removal of a hydrogen); in one embodiment from one to six carbon atoms; and in another embodiment from one to four carbon atoms; and in another embodiment one to three carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$-cycloalkyl or $C_{3-6}$-cycloalkyl refers to saturated cycloalkyl containing from 3 to 6 carbon ring atoms.

The term "alkoxy" refers to a straight chain saturated alkyl or branched chain saturated alkyl bonded through an oxygen atom. Non-limiting examples of such alkoxy groups are methoxy, ethoxy, propoxy, isopropoxy, butoxy, isobutoxy, tertiary butoxy, and pentoxy.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl, and 1,2,3,4-tetrahydronaphthalenyl.

The term "cycloalkyl" refers to a nonaromatic ring that is fully hydrogenated and exists as a single ring. Examples of such carbocyclic rings include cyclopropyl, cyclobutyl, cyclopentyl, and cyclohexyl.

The term "halo" or "halogen" refers to fluorine (which may be depicted as —F), chlorine (which may be depicted as —Cl), bromine (which may be depicted as —Br), or iodine (which may be depicted as —I).

The term "heteroaryl" refers to an aromatic ring structure containing from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered ring substituents such as pyridyl, pyrazyl, pyrimidinyl, and pyridazinyl; and 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" also includes fused ring systems having one or two rings wherein such rings may be fused, wherein fused is as defined above. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "5- to 6-membered heteroaryl" refers to a heteroaryl containing from 5 to 6 atoms, including one or more heteroatoms, in the cyclic moiety of the heteroaryl. The heteroatoms for this invention are selected from nitrogen, oxygen and sulfur.

If substituents are described as "independently" having more than one variable, each instance of a substituent is selected independent of the other from the list of variables available. Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, tautomers and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64(8), 1269-1288 by Haleblian (August 1975).

The compounds of the invention have asymmetric carbon atoms. The carbon-carbon bonds of the compounds of the invention may be depicted herein using a solid line ( ——— ), a solid wedge ( ▬◀ ), or a dotted wedge ( ........ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism and are regarded as compounds of the invention. For example, the compounds of Formula I may exist in several tautomeric forms, including the 2-amino-dihydrothiazine form, Ia, and the 2-imino-tetrahydrothiazine form, Ib.

All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula Ia' and Ib' and, collectively and generically, are referred to as compounds of Formula I.

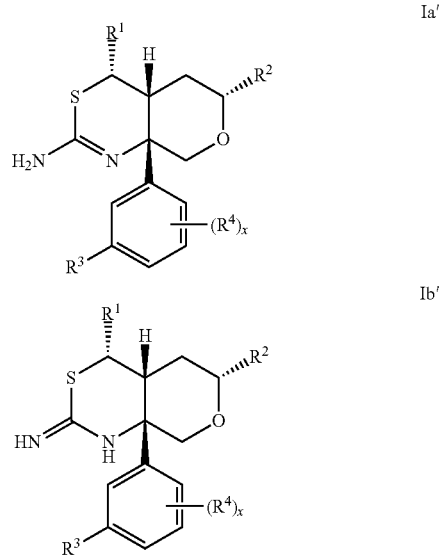

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention, which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenate, β-hydroxybutyrate, galactarate, galacturonate, adipate, alginate, butyrate, camphorate, cam phorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "promoieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature.

Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

In one embodiment of compounds of Formula I, $R^3$ is $-(C(R^5)_2)_m-(CN)$; m is 0 or 1; and $R^5$ at each occurrence is hydrogen; or a tautomer thereof or a pharmaceutically acceptable salt of said compound or tautomer.

In another embodiment of compounds of Formula I, $R^3$ is $-(C(R^5)_2)_n-(NHR^7)$; n is 1; and $R^5$ at each occurrence is hydrogen; or a tautomer thereof or a pharmaceutically acceptable salt of said compound or tautomer.

In another further embodiment of compounds of Formula I, $R^2$ is $C_{1-6}$ alkyl, optionally substituted with one to three fluoro, or $-(C(R^5)_2)_t-OR^6$; wherein t is 1; $R^5$ at each occurrence is hydrogen, and $R^6$ is $C_{1-3}$ alkyl, optionally substituted with one to three fluoro, or $-(C(R^5)_2)_n-(C_{6-10}$ aryl), wherein said aryl is optionally substituted with one to three substituents independently selected from halogen, $C_{1-6}$ alkyl, $-CH_2F$, $-CHF_2$, $-CF_3$, $-CN$ or $-OH$; or a tautomer thereof or a pharmaceutically acceptable salt of said compound or tautomer.

In a further embodiment of compounds of Formula I, $R^6$ is $-(C(R^5)_2)_n-(C_{6-10}$ aryl), said aryl is phenyl optionally substituted with substituents independently selected from halogen, $C_{1-6}$ alkyl, $-CH_2F$, $-CHF_2$, $-CF_3$, $-CN$ or $-OH$; n is 1; and $R^5$ at each occurrence is hydrogen; or a tautomer thereof or a pharmaceutically acceptable salt of said compound or tautomer.

In another embodiment, $R^2$ is $-(C(R^5)_2)_m-(C_{3-6}$ cycloalkyl) or $-(C(R^5)_2)_m-$(5- to 10-membered heteroaryl), wherein said cycloalkyl or heteroaryl is optionally substituted with halogen or $C_{1-6}$ alkyl optionally substituted with one to three fluoro; m is 0; and $R^5$ at each occurrence is hydrogen; or a tautomer thereof or a pharmaceutically acceptable salt of said compound or tautomer.

In further embodiments, $R^4$ is independently fluoro, chloro, methyl, ethyl, propyl, methoxy or ethoxy, wherein said methyl, ethyl and propyl groups are optionally substituted with one to three fluoro; and x is 0, 1 or 2; or a tautomer thereof or a pharmaceutically acceptable salt of said compound or tautomer.

In yet another embodiment, $R^1$ is hydrogen; $R^2$ is $C_{1-6}$ alkyl, $C_{3-6}$ cycloalkyl, 5-membered heteroaryl or $-CH_2-OR^6$; wherein said alkyl is optionally substituted with one F; $R^3$ is $-CN$ or $-CH_2-(NHR^7)$; $R^4$ is independently halogen or $C_{1-6}$ alkoxy; $R^6$ is hydrogen, $C_{1-6}$ alkyl, or $-CH_2$-phenyl; $R^7$ is $C_{1-6}$ alkyl optionally substituted with one to three substituents independently selected from halogen or $C_{1-6}$ alkoxy; and x is 0, 1, or 2; or a tautomer thereof or a pharmaceutically acceptable salt of said compound or tautomer.

In one embodiment, a compound of Formula I is represented by a compound of Formula Ia

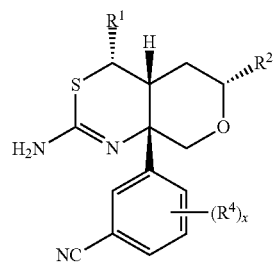

Ia wherein $R^1$, $R^2$, and $R^4$ are defined as described above, or a tautomer thereof or a pharmaceutically acceptable salt of said compound or tautomer.

In a further embodiment of the compound of Formula Ia, $R^4$ is independently fluoro, chloro, methyl, ethyl, propyl, methoxy, or ethoxy, wherein said methyl, ethyl and propyl groups are optionally substituted with one to three fluoro; and x is 0, 1 or 2; or a tautomer thereof or a pharmaceutically acceptable salt of said compound or tautomer. In a further embodiment, $R^2$ is methyl, optionally substituted with fluoro;

$R^4$ is independently methoxy, chloro or fluoro; x is 0, 1 or 2; or a tautomer thereof or a pharmaceutically acceptable salt of said compound or tautomer.

In a further embodiment of a compound of Formula Ia, $R^2$ is $—(C(R^5)_2)_m$-(5-membered heteroaryl); $R^4$ is independently methoxy, chloro or fluoro; m is 0; and x is 0, 1 or 2; or a tautomer thereof or a pharmaceutically acceptable salt of said compound or tautomer.

In a further embodiment of a compound of Formula Ia, $R^2$ is $—(C(R^5)_2)_t—OR^6$; $R^6$ is hydrogen, methyl or $—(C(R^5)_2)_n—(C_{6-10}$ aryl), wherein the aryl of $R^6$ is phenyl optionally substituted with substituents independently selected from halogen, $C_{1-6}$ alkyl, $—CH_2F$, $—CHF_2$, $—CF_3$, $—CN$ or $—OH$; $R^4$ is independently methoxy, chloro or fluoro; x is 0, 1 or 2; n is 1; and t is 1; or a tautomer thereof or a pharmaceutically acceptable salt of said compound or tautomer.

In a further embodiment of a compound of Formula Ia, $R^2$ is $—(C(R^5)_2)_m—(C_{3-6}$ cycloalkyl), wherein said cycloalkyl is optionally substituted with halogen or $C_{1-6}$ alkyl optionally substituted with one to three fluoro; $R^4$ is independently methoxy, chloro or fluoro; m is 0 or 1; and x is 0, 1 or 2; or a tautomer thereof or a pharmaceutically acceptable salt of said compound or tautomer. In a further embodiment, $R^2$ is cyclopropyl; and m is 0; or a tautomer thereof or a pharmaceutically acceptable salt of said compound or tautomer.

In another embodiment of a compound of Formula I is represented by a compound of Formula Ib

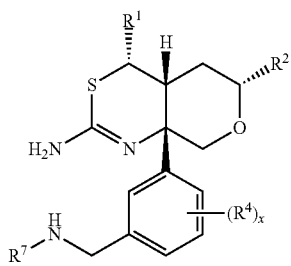

Ib wherein $R^1$, $R^2$, $R^4$ and $R^7$ are defined as described above; or a tautomer thereof or a pharmaceutically acceptable salt of said compound or tautomer.

In another embodiment, $R^7$ for each occurrence is methyl optionally substituted with one to three fluoro; or a tautomer thereof or a pharmaceutically acceptable salt of said compound or tautomer. In another embodiment, $R^2$ is $C_{1-3}$ alkyl, optionally substituted with one to three fluoro; $R^4$ is independently fluoro, chloro or methoxy; and x is 0, 1 or 2; or a tautomer thereof or a pharmaceutically acceptable salt of said compound or tautomer.

Yet another embodiment of the present invention is the compound of Formula I in which $R^1$ is hydrogen or fluoromethyl; $R^2$ is methyl, fluoromethyl, or 1-methyl-1H-pyrazol-4-yl; and $R^3$ is (2,2,2-trifluoroethyl)aminomethyl or (1-methoxypropan-2-yl)aminomethyl.

A further embodiment of the present invention is the compound of Formula I in which $R^1$ is hydrogen or fluoromethyl; $R^2$ is methyl, fluoromethyl, or 1-methyl-1H-pyrazol-4-yl; $R^3$ is (2,2,2-trifluoroethyl)aminomethyl or (1-methoxypropan-2-yl)aminomethyl; $R^4$ is fluoro and x is 1 or 2.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88(10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), including gut-selective MTP inhibitors (e.g., lomitapide, usistapide, granotapide, dirlotapide, mitratapide, implitapide and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide, described in PCT Publication No. WO 2005/116034 or US Publication No. 2005-0267100 A1), 5-HT$_{2c}$ agonists (e.g., lorcaserin), MCR4 agonists (e.g., compounds described in U.S. Pat. No. 6,818,658), lipase inhibitors (e.g., Cetilistat), PYY$_{3-36}$ (as used herein "PYY$_{3-36}$" includes analogs, such as peglated PYY$_{3-36}$, e.g., those described in US Publication 2006/0178501), opioid antagonists (e.g., naltrexone), oleoylestrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor [e.g., trodusquemine, hyrtiosal extract, and compounds disclosed by Zhang, S. et al., Drug Discovery Today, 12(9/10), 373-381 (2007)], a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211, as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g., SSTR1, SSTR2, SSTR3 and SSTR5), inhibitors or modulators of PDHK2 or PDHK4, inhibitors of MAP4K4, modulators of IL1 family including IL1 beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos. WO04/032868, WO05/025616, WO06/036291, WO06/069081, WO06/118959, in US Patent Publication Nos. US2003/0073655, US2004/0192898, US2005/0048049, US2005/0019328, in European Patent Publication Nos. EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®, KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos. US2005-0043354, US2005-0267095, US2005-0256135, US2008-0096955, US2007-1079175, and US2008-0176925; International Patent Publication Nos. WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (1-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos. US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(xiv) serotonin (5-hydroxytryptamine) 1A ($5-HT_{1A}$) receptor antagonists, such as spiperone, levo-pindolol, lecozotan;

(xv) serotonin (5-hydroxytryptamine) 2C ($5-HT_{2c}$) receptor agonists, such as vabicaserin, and zicronapine; serotonin (5-hydroxytryptamine) 4 ($5-HT_4$) receptor agonists/antagonists, such as PRX-03140 (Epix) and PF-04995274;

(xvi) serotonin (5-hydroxytryptamine) 3C ($5-HT_{3c}$) receptor antagonists, such as Ondansetron (Zofran);

(xvii) serotonin (5-hydroxytryptamine) 6 ($5-HT_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide; and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

Scheme 1 refers to the preparation of compounds of Formula I. Referring to Scheme 1, the compound of Formula I can be prepared from the compound of Formula II through removal of protecting group $P^1$. $P^1$ in this case refers to groups well known to those skilled in the art for amine protection. For example, $P^1$ may be a benzoyl group (Bz), which can be cleaved via acidic conditions, or through treatment with 1,8-diazabicyclo[5.4.0]undec-7-ene (DBU) in methanol. Alternatively $P^1$ may be one of many other protecting group suitable for amines, including 9-fluorenylmethoxycarbonyl (Fmoc) or tert-butoxycarbonyl (BOC) and can be cleaved under standard conditions known to one skilled in the art.

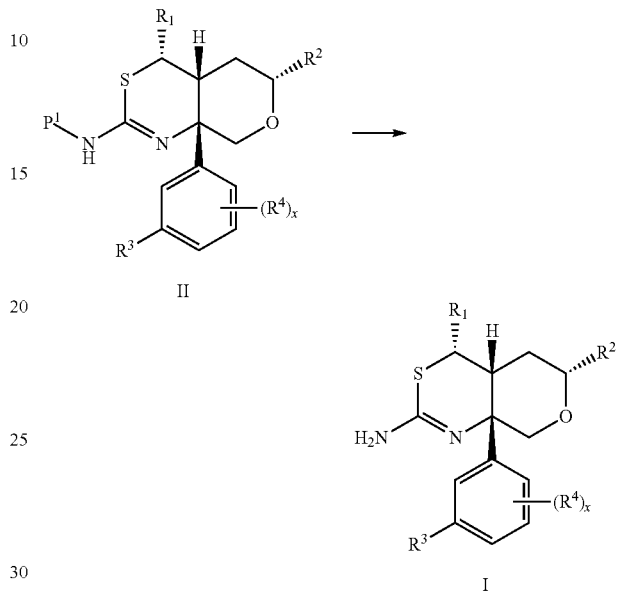

Scheme 1

Scheme 2 refers to the preparation of compounds II wherein $P^1$ is Bz or Boc and $R^3$ is CN. Protected thiazin-2-amines of Formula III are subjected to standard palladium-catalyzed cyanation conditions (as in *J. Med. Chem.* 2005, 48, 1132-1144), for example, zinc cyanide and bis-palladium trisdibenzylideneacetone, to give compounds of Formula II. Compound II can be converted into a compound of Formula I according to the methods of Scheme 1.

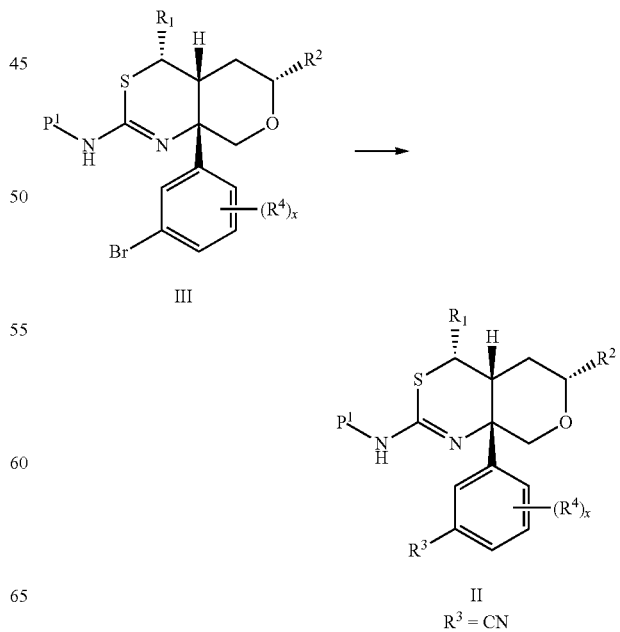

Scheme 2

Scheme 3 refers to the preparation of compounds III wherein $P^1$ is Bz or Boc. The oxidation of compounds of Formula IV to carboxylic acids V can be accomplished by a number of standard oxidation protocols, for instance using tetrapropylammonium perruthenate (TPAP) and N-methyl-morpholine-N-oxide (NMO) in acetonitrile. Carboxylic acid V can be converted to compounds of Formula III via a number of methods outlined in the following reference: Practical Synthetic Organic Chemistry: Reactions, Principles, and Techniques. 2011, Chapter 13, Wiley & Sons, Inc., Caron, S., ed., as well as additional methods known to those skilled in the art. A compound of Formula III can be converted into a compound of Formula I according to the methods of Schemes 2, 7 and 1.

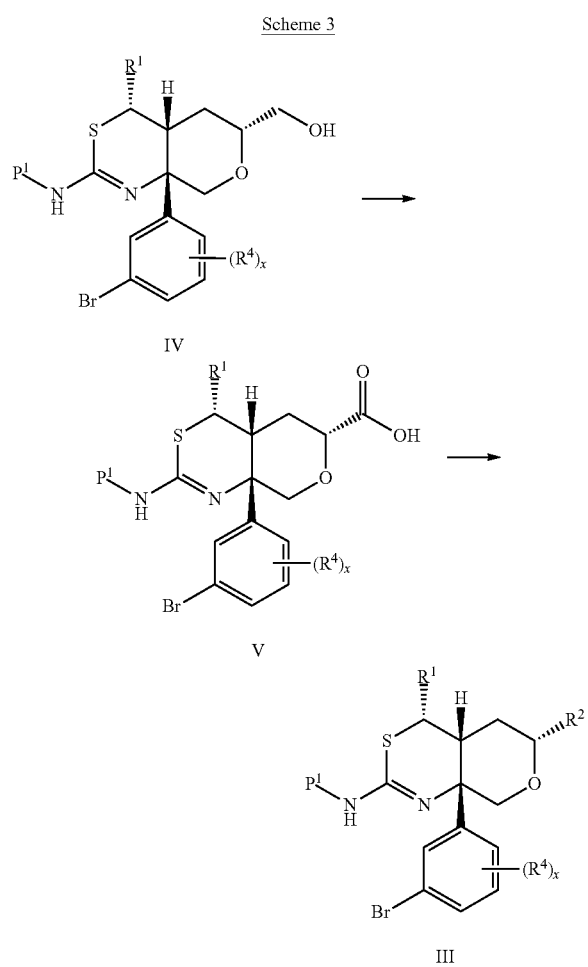

Scheme 4 refers to the preparation of compounds III wherein $P^1$ is Bz or Boc. The oxidation of compounds of Formula IV to aldehydes VI can be effected by a number of standard oxidation protocols, for instance using Dess-Martin periodinane or sulfur trioxide-pyridine with DMSO (Parikh-Doering conditions). Aldehyde VI can be converted to compounds of Formula III via a number of methods outlined in the following reference: Practical Synthetic Organic Chemistry: Reactions, Principles, and Techniques. 2011, Chapter 13, Wiley & Sons, Inc., Caron, S., ed. Compound III can be converted into a compound of Formula I according to the methods of Schemes 2, 7 and 1.

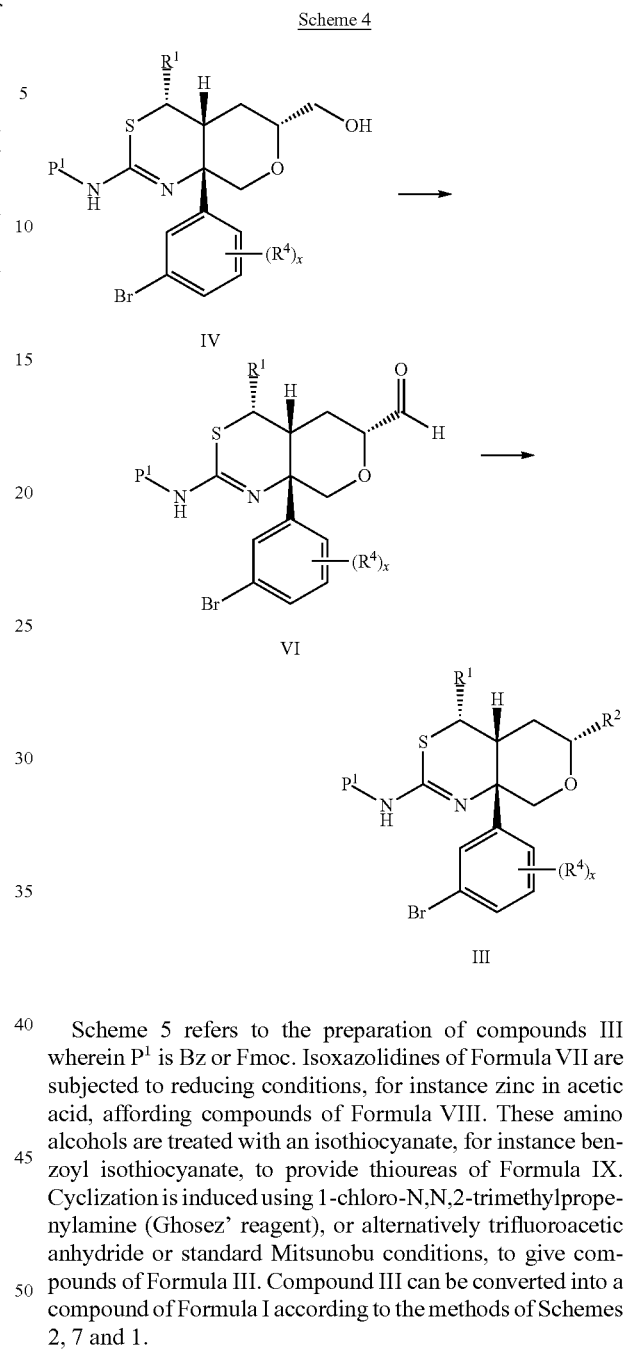

Scheme 5 refers to the preparation of compounds III wherein $P^1$ is Bz or Fmoc. Isoxazolidines of Formula VII are subjected to reducing conditions, for instance zinc in acetic acid, affording compounds of Formula VIII. These amino alcohols are treated with an isothiocyanate, for instance benzoyl isothiocyanate, to provide thioureas of Formula IX. Cyclization is induced using 1-chloro-N,N,2-trimethylpropenylamine (Ghosez' reagent), or alternatively trifluoroacetic anhydride or standard Mitsunobu conditions, to give compounds of Formula III. Compound III can be converted into a compound of Formula I according to the methods of Schemes 2, 7 and 1.

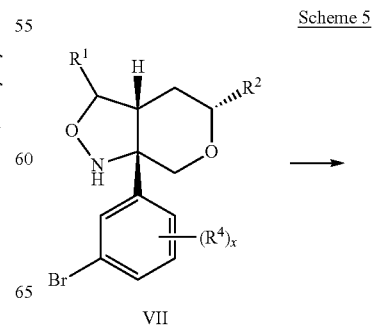

-continued

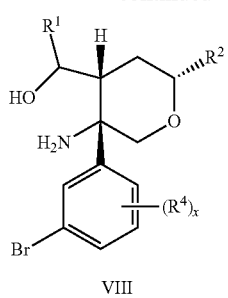

VIII

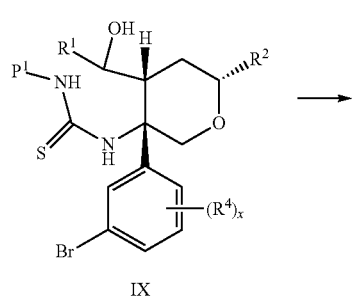

IX

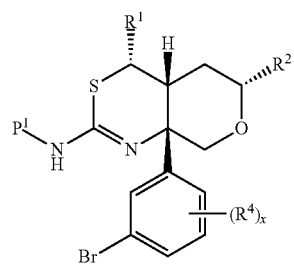

III

Scheme 6 refers to the preparation of compounds III wherein $R^2$ is $CH_2F$. Primary alcohols of Formula IV (which may be obtained via the chemistry depicted in Scheme 8) are treated with an appropriate fluorinating reagent, for instance diethylaminosulfur trifluoride (DAST), although other suitable fluorinating reagents known to one skilled in the art can be utilized. The resulting compounds of Formula III can be converted into compounds of Formula I according to the methods of Schemes 2, 7 and 1.

Scheme 6

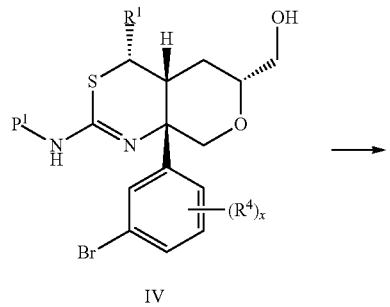

IV

-continued

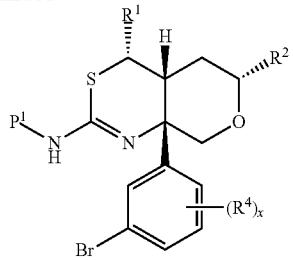

III
$R^2 = CH_2F$

Scheme 7 refers to the preparation of compounds II wherein $R^3$ is —$CH_2NH$-alkyl. Nitriles of Formula X (which may be obtained via the chemistry depicted in Scheme 2) are subjected to reduction conditions in the presence of an electrophilic protecting group reagent, for instance sodium borohydride in the presence of nickel chloride and di-tert-butyl dicarbonate ($Boc_2O$), although other suitable reducing reagents or protecting groups known to one skilled in the art can be utilized. The amines of Formula XI are then deprotected under suitable conditions, for instance hydrochloric acid in dioxane, although other methods for removing the tert-butoxycarbonyl (Boc) group can also be used. The resulting compounds of Formula XII are then treated with an appropriate alkylating agent, for instance trifluoroethyl trifluoromethanesulfonate, to provide compounds of Formula II wherein $R^3$ is —$CH_2NH$-alkyl, which can be converted into compounds of Formula I according to the methods of Scheme 1.

Scheme 7

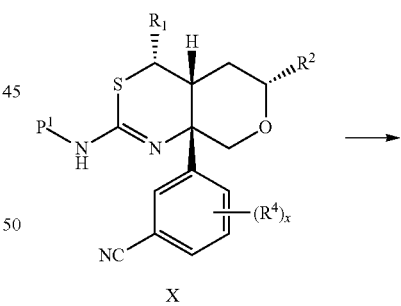

X

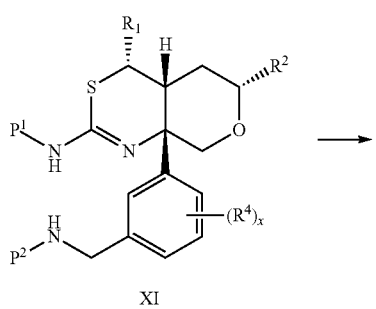

XI

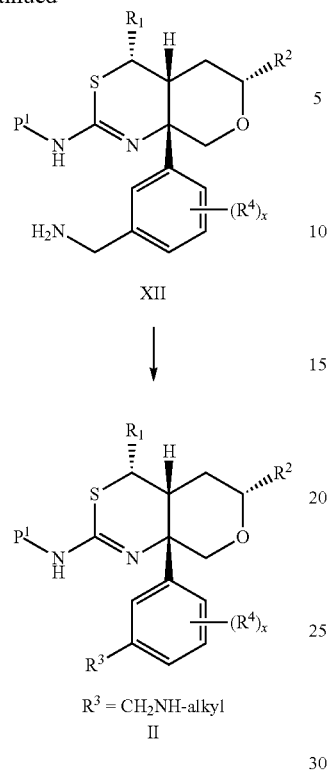

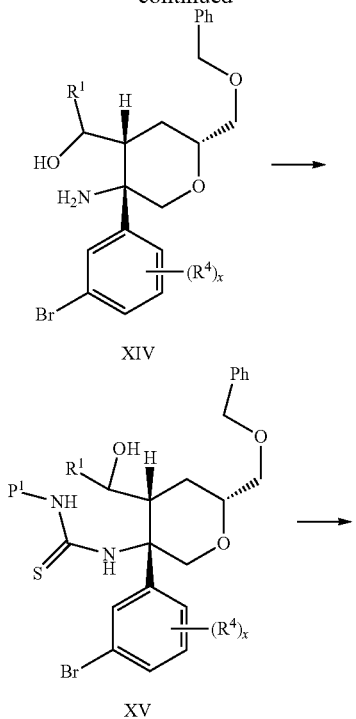

Scheme 8 refers to the preparation of compounds IV wherein $P^1$ is Bz or Fmoc. Isoxazolidines of Formula XIII (which may be obtained via the chemistry depicted in Scheme 9, utilizing a benzyloxymethyl group in place of $R^2$) are subjected to reducing conditions, for instance zinc in acetic acid, affording compounds of Formula XIV. The amino alcohols XIV are treated with an isothiocyanate, for instance benzoyl isothiocyanate, to provide thioureas of Formula XV. Cyclization is induced using Ghosez' reagent or strong acid, including for instance sulfuric acid; alternatively, standard Mitsunobu conditions can be employed, to give compounds of Formula XVI. Cleavage of the benzyl ether under standard conditions, for instance using boron trichloride, provides alcohols of Formula IV. Compound IV can be converted into a compound of Formula I according to the methods of Schemes 2-4, 6, 7 and 1.

Scheme 8

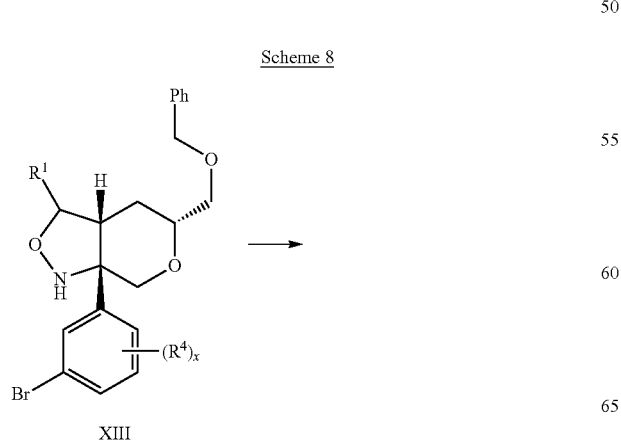

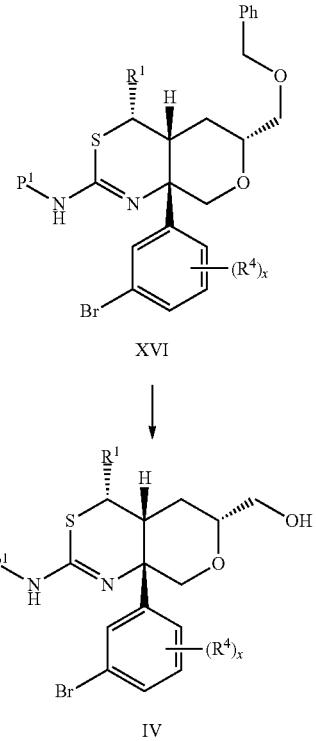

Scheme 9 refers to the preparation of compound VII. Homoallylic alcohol XVII is alkylated with 2-bromo-1,1-dimethoxyethane under basic conditions, such as treatment with potassium hydride, to provide the corresponding ether XVIII. The acetal is cleaved under acidic conditions, aqueous hydrochloric acid as an example, to give aldehyde XIX. Condensation with a hydroxylamine salt, such as hydroxylamine sulfate, provides a geometric mixture of the corresponding oxime XX. Cycloaddition to form isoxazoline XXI may be carried out by treatment of oxime XX with an oxidizing agent, such as sodium hypochlorite or N-chlorosuccinimide. Reaction of isoxazoline XXI with an appropriate arylmetallic reagent [for instance, an aryllithium such as (5-bromo-2,4-difluorophenyl)lithium or (5-bromo-2-fluorophenyl)lithium, or the corresponding aryl Grignard reagents] at low temperature, e.g., −78° C., yields compounds of Formula VII. One of ordinary skill in the art will recognize that the stereochemistry of addition of the arylmetallic reagent is determined by the stereochemistry of the adjacent methine center, yielding a racemic mixture of cis-fused diastereomers, which can be converted into compounds of Formula I according to the methods of Schemes 5, 2, 7 and 1.

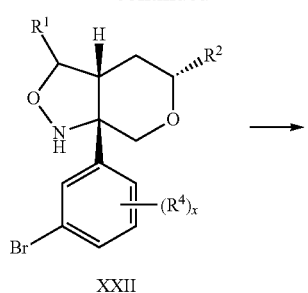

Scheme 9

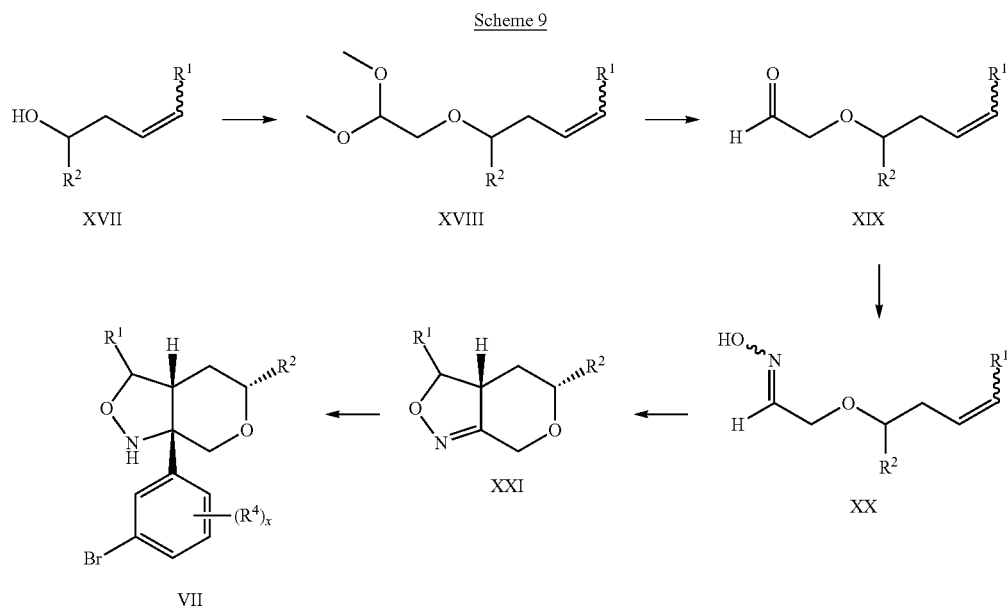

Scheme 10 refers to the preparation of compounds II wherein $P^1$ is Bz or Fmoc. Reaction of isoxazoline XXI with an appropriate arylmetallic reagent (for instance, an aryllithium such as 2-fluoro-5-cyanophenyllithium, or the corresponding aryl Grignard reagent) at low temperature, e.g., −78° C., yields compounds of Formula XXII. Isoxazolidines of Formula XXII are subjected to reducing conditions, for instance zinc in acetic acid, affording compounds of Formula XXIII. These amino alcohols are treated with an isothiocyanate, for instance benzoyl isothiocyanate, to provide thioureas of Formula XXIV. Cyclization is induced using 1-chloro-N,N,2-trimethylpropenylamine (Ghosez' reagent) to give compounds of Formula II. Compound II can be converted into a compound of Formula I according to the methods of Scheme 1.

Scheme 10

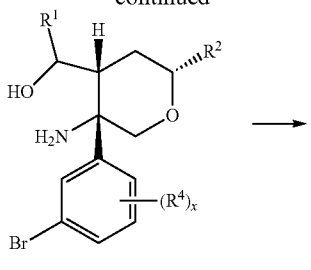

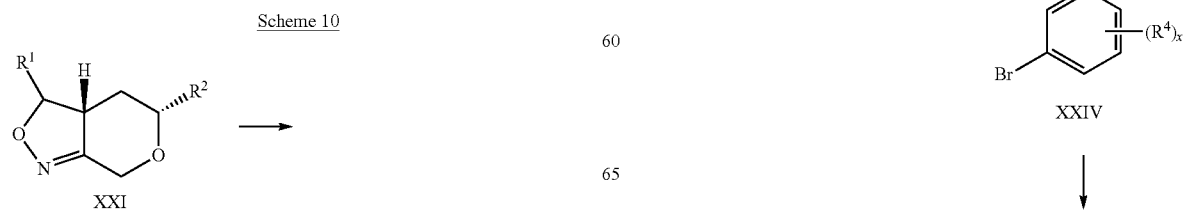

-continued

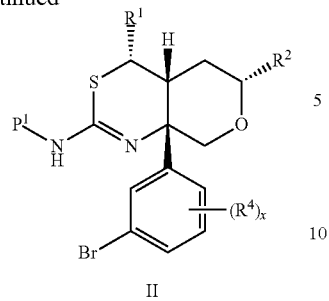

II

Scheme 11 refers to the preparation of secondary alcohols of Formula XXV. Reaction of (R)-2-[(benzyloxy)methyl]oxirane with an appropriate alkenylmetallic reagent (for instance, an alkenyl Grignard such as propenylmagnesium bromide), in the presence of copper iodide, yields compounds of Formula XXV. Compound XXV can be converted into a compound of Formula I according to the methods of Scheme 9, 5, 2 and 1.

Scheme 11

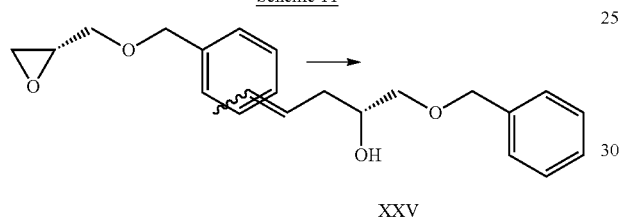

XXV

Scheme 12 refers to an alternative preparation of compounds II. Treatment of aryl bromide III under palladium-catalyzed carbonylation conditions, such as catalytic [1,1'-bis(diphenylphosphino)ferrocene]dichloropalladium(II) in methanol under an atmosphere of carbon monoxide, affords the corresponding methyl ester XXVI. Subsequent reduction using an appropriate hydride source, including but not limited to lithium aluminum hydride, yields compounds of Formula XXVII. Oxidation of the primary alcohols using an appropriate oxidant, including but not limited to pyridinium chlorochromate (PCC), affords the corresponding aldehyde of Formula XXVIII. Treatment of the aldehyde with the desired amine, such as 1-methoxypropane-2-amine, and a reductant suitable for reductive amination conditions, such as sodium borohydride or sodium triacetoxyborohydride, provides compounds of Formula II. Compound II can be converted into a compound of Formula I according to the methods of Scheme 1.

Scheme 12

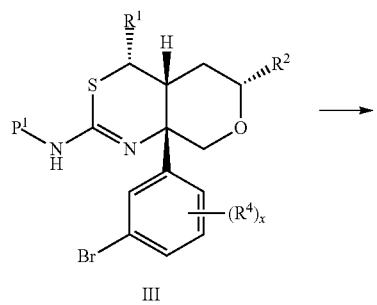

III

-continued

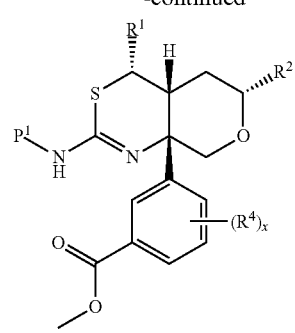

XXVI

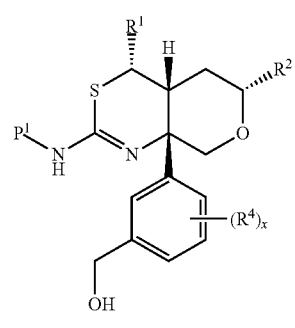

XXVII

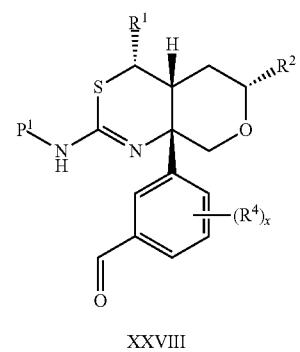

XXVIII

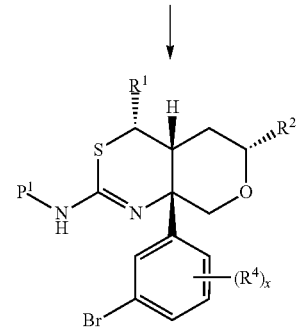

II

Scheme 13 describes an alternative preparation of compounds of Formula XXVIII. Treatment of aryl bromide III under lithium-halogen exchange conditions using an alkyllithium, such as methyllithium or sec-butyllithium, and subsequent trapping with an aldehyde equivalent, including but not limited to N-methyl-N-phenylformamide, provides compounds of Formula XXVIII. Compound XXVIII can be converted into a compound of Formula I according to the methods of Schemes 12 and 1.

Scheme 13

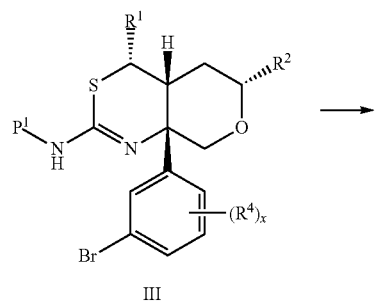

III

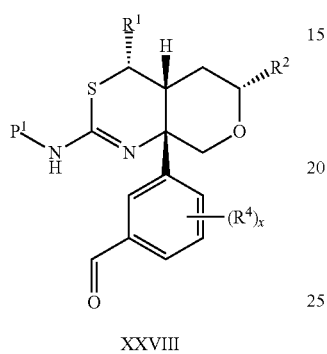

XXVIII

Scheme 14 describes an alternative preparation of compounds of Formula XVIIIb, where the stereochemistry of the double bond is of the E configuration. Treatment of secondary alcohol XXIX (prepared by the methods described by G. V. M. Sharma and K. Veera Babu, *Tetrahedron: Asymmetry* 2007, 18, 2175-2184) with 1,1-diethoxy-2-iodoethane using a base, such as sodium hydride, provides compounds of Formula XXX. Deprotection of compound XXX, for instance when P² is 2-tetrahydropyranyl, with benzenesulfonic acid, provides propargyl alcohols of Formula XXXI. Reduction using a stereospecific reducing agent, including but not limited to lithium aluminum hydride, provides allylic alcohols of Formula XVIIIb. Compounds of Formula XVIIIb can be converted into a compound of Formula I according to the methods of Schemes 9, 5, 2 and 1.

Scheme 14

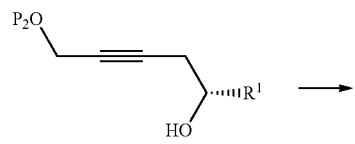

XXIX

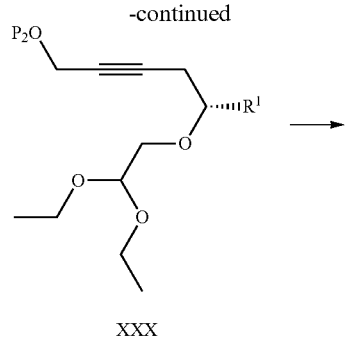

XXX

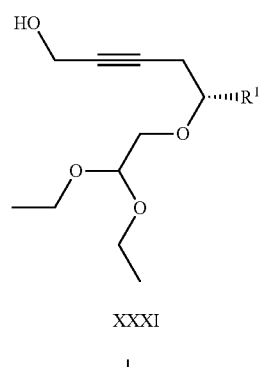

XXXI

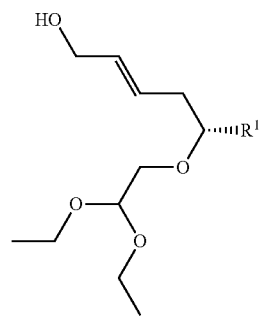

XVIIIb

Preparation P1

(3aR,5R)-5-[(Benzyloxy)methyl]-3,3a,4,5-tetrahydro-7H-pyrano[3,4-c][1,2]oxazole (P1)

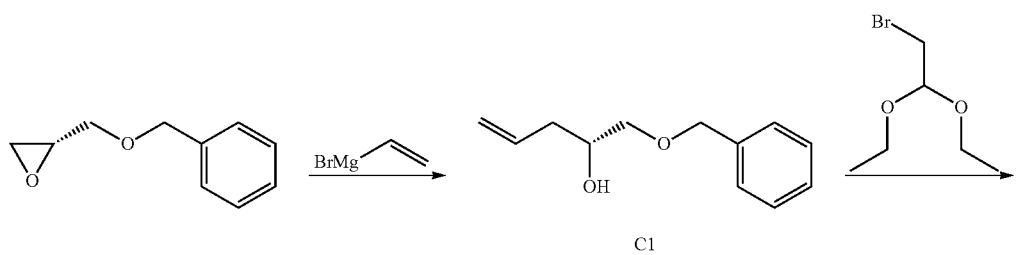

C1

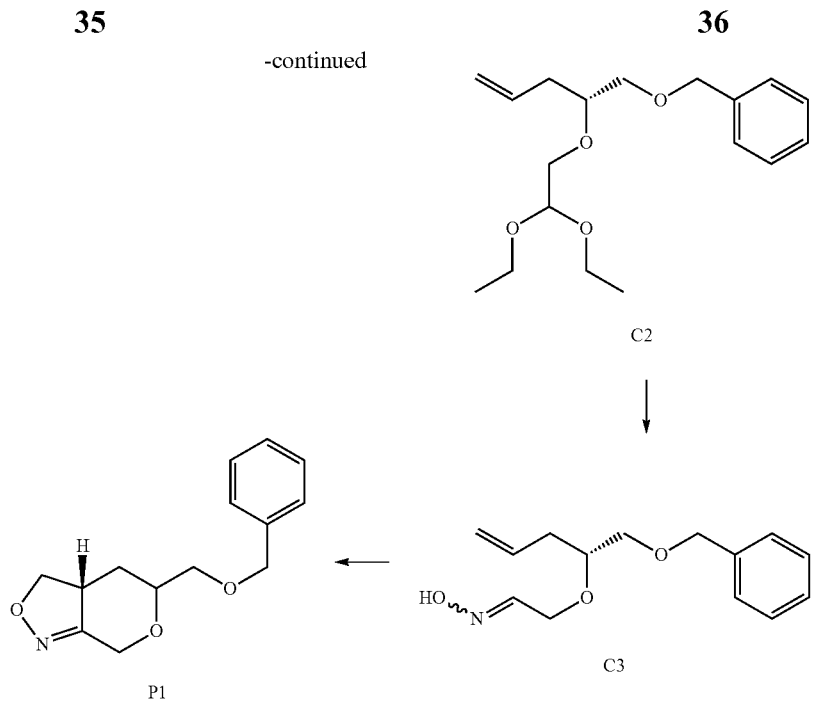

Step 1. Synthesis of (2R)-1-(benzyloxy)pent-4-en-2-ol (C1)

To a solution of (2R)-2-[(benzyloxy)methyl]oxirane (167 g, 1.02 mol) in tetrahydrofuran (2 L) was added copper(I) iodide (11.62 g, 61.02 mmol) at room temperature. The mixture was stirred for 5 minutes, then cooled to −78° C. A solution of vinylmagnesium bromide (1 M in tetrahydrofuran, 1.12 L, 1.12 mol) was added drop-wise over 1 hour while the reaction temperature was maintained below −70° C. Upon completion of the addition, the cooling bath was removed and the reaction mixture was left to stir at room temperature for 1 hour, then quenched by slow addition of aqueous ammonium chloride solution (200 mL). After dilution with additional aqueous ammonium chloride solution (1.5 L) and ethyl acetate (1.5 L), the aqueous layer was extracted with ethyl acetate (1 L) and the combined organic layers were washed with aqueous ammonium chloride solution (1.5 L), dried over magnesium sulfate, filtered, and concentrated in vacuo. Three batches of this reaction were carried out and combined to give the product as an orange oil. Yield: 600 g, 3.1 mmol, quantitative. $^1$H NMR (400 MHz, $CDCl_3$) δ 7.28-7.40 (m, 5H), 5.78-5.90 (m, 1H), 5.08-5.17 (m, 2H), 4.57 (s, 2H), 3.86-3.94 (m, 1H), 3.53 (dd, J=9.6, 3.3 Hz, 1H), 3.39 (dd, J=9.6, 7.4 Hz, 1H), 2.26-2.34 (m, 3H).

Step 2. Synthesis of ({[(2R)-2-(2,2-diethoxyethoxy)pent-4-en-1-yl]oxy}methyl)benzene (C2)

To a suspension of sodium hydride (60% in mineral oil, 98.8 g, 2.47 mol) in tetrahydrofuran (1 L) at room temperature was added drop-wise over 30 minutes a solution of (2R)-1-(benzyloxy)pent-4-en-2-ol (C1) (190 g, 0.988 mol) in tetrahydrofuran (500 mL), while the reaction temperature was maintained below 30° C. After 30 minutes, a solution of 2-bromo-1,1-diethoxyethane (390 g, 1.98 mol) in tetrahydrofuran (500 mL) was added drop-wise. The reaction mixture was stirred at room temperature for 1 hour, then the temperature was gradually increased to 70° C. and the reaction mixture was left to stir at 70° C. for 18 hours. It was then cooled to room temperature, subsequently cooled in an ice bath, and quenched by slow addition of ice/water (200 mL), while keeping the internal reaction temperature at approximately 18° C. The mixture was partitioned between saturated aqueous sodium chloride solution (1 L) and ethyl acetate (1 L), and the organic layer was washed with saturated aqueous sodium chloride solution (1 L), dried over magnesium sulfate, filtered, and concentrated under reduced pressure. Purification was effected by filtration through a pad of silica (Gradient: 0% to 20% ethyl acetate in heptane) to afford the product as an orange oil. Yield: 257 g of 60% purity, approximately 500 mmol, 51% yield and 57.76 g of 90% purity, approximately 170 mmol, 17% yield. $^1$H NMR (400 MHz, $CDCl_3$), product peaks only: δ 7.26-7.38 (m, 5H), 5.78-5.90 (m, 1H), 5.02-5.13 (m, 2H), 4.61 (t, J=5.3 Hz, 1H), 4.55 (s, 2H), 3.48-3.74 (m, 9H), 2.31-2.37 (m, 2H), 1.22 (t, J=7.1 Hz, 3H), 1.21 (t, J=7.1 Hz, 3H).

Step 3. Synthesis of 2-{[(2R)-1-(benzyloxy)pent-4-en-2-yl]oxy}-N-hydroxyethanimine (C3)

A solution of ({[(2R)-2-(2,2-diethoxyethoxy)pent-4-en-1-yl]oxy}methyl)benzene (C2) (234 g, 0.759 mol) in formic acid (400 mL) and water (100 mL) was stirred at room temperature for 2 hours. As LCMS analysis revealed a small amount of remaining starting material, formic acid (50 mL) was added and the reaction mixture was stirred for a further 30 minutes. The reaction mixture was diluted with ethanol (1 L) and water (400 mL). Hydroxylamine sulfate (435 g, 2.65 mol) and sodium acetate (217 g, 2.64 mol) were added and the reaction was stirred at room temperature for 18 hours. The reaction mixture was then filtered and concentrated in vacuo; the residue was partitioned between ethyl acetate (500 mL) and water (1 L), and the aqueous layer was extracted with ethyl acetate (3×500 mL). The combined organic layers were washed with saturated aqueous sodium chloride solution (2×500 mL), dried over magnesium sulfate, filtered, and concentrated under reduced pressure to provide the product as an orange oil (234 g), which was taken directly to the following step. By ¹H NMR, this material consisted of a roughly 1:1 mixture of oxime isomers. LCMS m/z 250.1 [M+H⁺]. ¹H NMR (400 MHz, CDCl₃), characteristic peaks: δ [7.52 (t, J=5.5 Hz) and 6.96 (t, J=3.6 Hz), total 1H], 7.28-7.39 (m, 5H), 5.74-5.87 (m, 1H), 5.04-5.14 (m, 2H), 4.55 and 4.56 (2 s, total 2H), {4.45-4.55 (m) and [4.27 (dd, half of ABX pattern, J=13.2, 5.4 Hz) and 4.21 (dd, half of ABX pattern, J=13.2, 5.6 Hz)], total 2H}, 2.30-2.37 (m, 2H).

Step 4. Synthesis of (3aR,5R)-5-[(benzyloxy)methyl]-3,3a,4,5-tetrahydro-7H-pyrano[3,4-c][1,2]oxazole (P1)

An aqueous solution of sodium hypochlorite (14.5% solution, 600 mL) was added drop-wise to a 0° C. solution of 2-{[(2R)-1-(benzyloxy)pent-4-en-2-yl]oxy}-N-hydroxyethanimine (C3) (224 g from the previous step, ≤0.759 mol) in dichloromethane (1 L), while the internal temperature was maintained below 15° C. After completion of the addition, the reaction mixture was left to stir at 0° C. for 1.5 hours, then diluted with water (1 L) and dichloromethane (500 mL). The aqueous layer was extracted with dichloromethane (2×500 mL), and the combined organic layers were washed with saturated aqueous sodium chloride solution (500 mL), water (500 mL) and again with saturated aqueous sodium chloride solution (500 mL). They were subsequently dried over magnesium sulfate, filtered, and concentrated in vacuo. Purification via silica gel chromatography (Gradient: 0% to 25% ethyl acetate in heptane) afforded the product as a colorless oil. The indicated relative stereochemistry of compound P1 was assigned based on nuclear Overhauser enhancement studies, which revealed an interaction between the methine protons on carbons 3a and 5. Yield: 85.3 g, 345 mmol, 45% over 2 steps. LCMS m/z 248.1 [M+H⁺]. ¹H NMR (400 MHz, CDCl₃) δ 7.27-7.40 (m, 5H), 4.77 (d, J=13.5 Hz, 1H), 4.54-4.65 (m, 3H), 4.22 (dd, J=13.5, 1 Hz, 1H), 3.79 (dd, J=11.7, 8.0 Hz, 1H), 3.69-3.76 (m, 1H), 3.57 (dd, half of ABX pattern, J=10.1, 5.9 Hz, 1H), 3.49 (dd, half of ABX pattern, J=10.1, 4.3 Hz, 1H), 3.39-3.5 (m, 1H), 2.20 (ddd, J=12.9, 6.5, 1.6 Hz, 1H), 1.51-1.62 (m, 1H).

Alternate conversion of ({[(2R)-2-(2,2-diethoxyethoxy)pent-4-en-1-yl]oxy}methyl)benzene (C2) to (3aR,5R)-5-[(benzyloxy)methyl]-3,3a,4,5-tetrahydro-7H-pyrano[3,4-c][1,2]oxazole (P1)

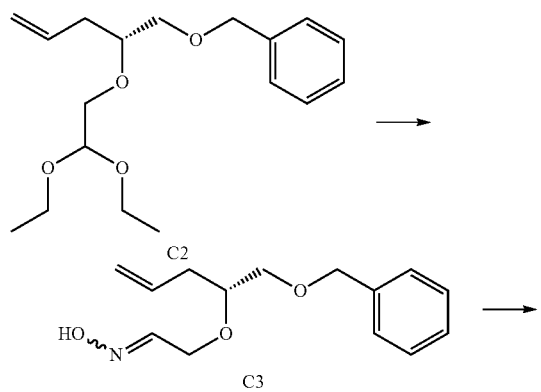

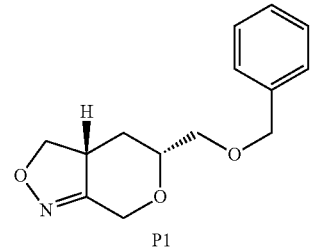

P1

Step 1. Synthesis of 2-{[(2R)-1-(benzyloxy)pent-4-en-2-yl]oxy}-N-hydroxyethanimine (C3)

({[(2R)-2-(2,2-Diethoxyethoxy)pent-4-en-1-yl]oxy}methyl)benzene (C2) (12.4 g, 40.2 mmol) was dissolved in acetic acid (28 mL) and water (12 mL). Hydroxylamine hydrochloride (2.84 g, 40.9 mmol) was added as a solid. After 1 hour, additional hydroxylamine hydrochloride (2.84 g, 40.9 mmol) was added. After 1 more hour, the reaction mixture was diluted with tert-butyl methyl ether (100 mL) and washed with water (3×50 mL), then washed with aqueous potassium carbonate solution (0.5 M, 100 mL). The organic layer was concentrated to provide the product as a pale yellow oil, which consisted of a roughly equimolar mixture of oxime isomers, as assessed by ¹H NMR. Yield: 9.60 g, 38.5 mmol, 96%. ¹H NMR (400 MHz, CDCl₃) δ 7.98 and 7.67 (2 br s, total 1H), [7.50 (t, J=5.6 Hz) and 6.95 (t, J=3.6 Hz), total 1H], 7.28-7.39 (m, 5H), 5.74-5.87 (m, 1H), 5.04-5.14 (m, 2H), 4.55 and 4.56 (2 s, total 2H), 4.47-4.49 (m, 1H), 4.18-4.28 (m, 1H), 3.47-3.65 (m, 3H), 2.30-2.37 (m, 2H).

Step 2. Synthesis of (3aR,5R)-5-[(benzyloxy)methyl]-3,3a,4,5-tetrahydro-7H-pyrano[3,4-c][1,2]oxazole (P1)

Pyridine (23.1 mL, 286 mmol) was added to a solution of 2-{[(2R)-1-(benzyloxy)pent-4-en-2-yl]oxy}-N-hydroxyethanimine (C3) (35.6 g, 143 mmol) in dichloromethane (350 mL). N-Chlorosuccinimide (19.4 g, 145 mmol) was added in portions over roughly 2 hours. The reaction was stirred for 3 hours, then diluted with an aqueous solution of sodium sulfite (5 g in 100 mL water). The mixture was stirred for 20 minutes, and the aqueous layer was extracted with dichloromethane; the combined organic layers were washed with water, dried, and concentrated. Purification via silica gel chromatography (Eluent: 1:2 ethyl acetate/hexanes) afforded the product. Yield: 21.2 g, 85.7 mmol, 60%. ¹H NMR (400 MHz, CDCl₃) δ 7.28-7.40 (m, 5H), 4.77 (d, J=13.4 Hz, 1H), 4.55-4.65 (m, 3H), 4.22 (dd, J=13.5, 1.3 Hz, 1H), 3.79 (dd, J=11.7, 8.0 Hz, 1H), 3.69-3.76 (m, 1H), 3.57 (dd, half of ABX pattern, J=10.2, 5.9 Hz, 1H), 3.49 (dd, half of ABX pattern, J=10.2, 4.3 Hz, 1H), 3.40-3.5 (m, 1H), 2.21 (ddd, J=12.9, 6.5, 1.8 Hz, 1H), 1.57 (ddd, J=13, 12, 11 Hz, 1H).

Preparation P2

(3aR,5S)-5-Methyl-3,3a,4,5-tetrahydro-7H-pyrano[3,4-c][1,2]oxazole

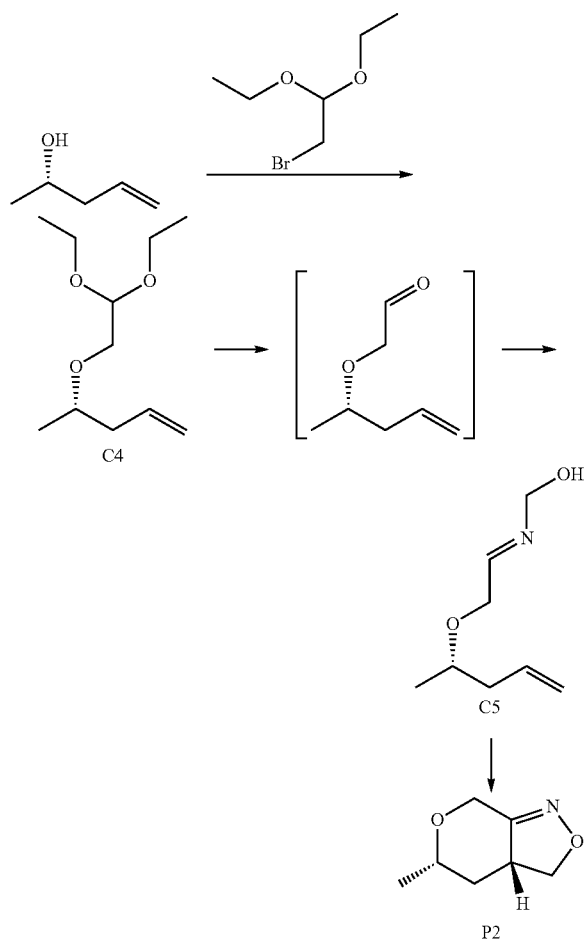

Step 1: Synthesis of (4S)-4-(2,2-dimethoxyethoxy)pent-1-ene (C4)

To a suspension of sodium hydride (60% in mineral oil, 13.9 g, 0.348 mol) in tetrahydrofuran (350 mL) was added a solution of (S)-pent-4-en-2-ol (10.0 g, 0.116 mol) in tetrahydrofuran (50 mL) at 0° C. The reaction was warmed to room temperature and stirred for 30 minutes and 2-bromo-1,1-diethoxyethane (68.6 g, 0.348 mol) was added at the same temperature. The reaction mixture was refluxed for 18 hours. The mixture was cooled to 0° C. and quenched with water (50 mL). The mixture was partitioned between ethyl acetate (300 mL) and water (200 mL). The organic phase was washed with brine (2×100 mL), dried and concentrated in vacuo. Silica gel chromatography (petroleum ether/ethyl acetate=30:1) provided the product as a yellow oil. Yield: 17.3 g, 99.6 mmol, 74%. $^1$H NMR (400 MHz, CDCl$_3$), δ 5.76-5.85 (m, 1H), 5.02-5.09 (m, 2H), 4.58-4.60 (m, 1H), 3.66-3.74 (m, 2H), 3.43-3.61 (m, 5H), 2.29-2.36 (m, 1H), 2.13-2.20 (m, 1H), 1.21 (t, J=7.2 Hz, 6H), 1.14 (d, J=6.4 Hz, 3H).

Step 2: Synthesis of (1E)-N-hydroxy-2-[(2S)-pent-4-en-2-yloxy]ethanimine (C5)

To a solution of C4 (17.4 g, 85.8 mmol) in tetrahydrofuran (100 mL) was added aqueous hydrochloric acid (2 M, 51.0 mL, 0.102 mol) at room temperature. The reaction was heated to 75° C. for 1 hour. The mixture was concentrated in vacuo, at which point ethanol (100 mL) and water (20 mL) were added, followed by the addition of sodium acetate (35.17 g, 0.429 mol) and hydroxylamine hydrochloride (17.9 g, 0.257 mol). The reaction was stirred at 60° C. for 18 hours. The reaction mixture was concentrated in vacuo and the residue was partitioned between water and dichloromethane. The aqueous layer was extracted with dichloromethane (3×200 mL). The combined organic phases were dried over sodium sulfate, filtered and concentrated in vacuo. Silica gel chromatography (petroleum ether/ethyl acetate=10:1) provided the product as a yellow oil, which was used without further purification in the subsequent step. Yield: 8.6 g, 60.1 mmol, 70%.

Step 3: Synthesis of (3aR,5S)-5-methyl-3,3a,4,5-tetrahydro-7H-pyrano[3,4-c][1,2]oxazole (P2)

To a solution of C5 (8.6 g, 0.06 mol) and triethylamine (0.455 g, 4.50 mmol) in dichloromethane (150 mL) at room temperature was slowly added a 6% aqueous solution of sodium hypochlorite (90 mL) while maintaining the internal temperature between 20° C. and 25° C. After the addition, the organic phase was separated, dried and concentrated in vacuo. Silica gel chromatography (petroleum ether/ethyl acetate=10:1) provided the product as a yellow oil. Yield: 5.70 g, 40.4 mmol, 67%. LCMS m/z 142.1 [M+H$^+$], $^1$H NMR (400 MHz, CDCl$_3$), δ 4.68 (d, J=13.2 Hz, 1H), 4.59 (dd, J=10, 8 Hz, 1H), 4.18 (d, J=13.2 Hz, 1H), 3.76 (dd, J=12, 8 Hz, 1H), 3.59-3.66 (m, 1H), 3.39-3.50 (m, 1H), 2.14-2.19 (m, 1H), 1.42-1.51 (m, 1H), 1.25 (d, J=6 Hz, 3H).

Preparation P3

(3S,3aR,5R)-5-[(Benzyloxy)methyl]-3-methyl-3,3a,4,5-tetrahydro-7H-pyrano[3,4-c][1,2]oxazole (P3)

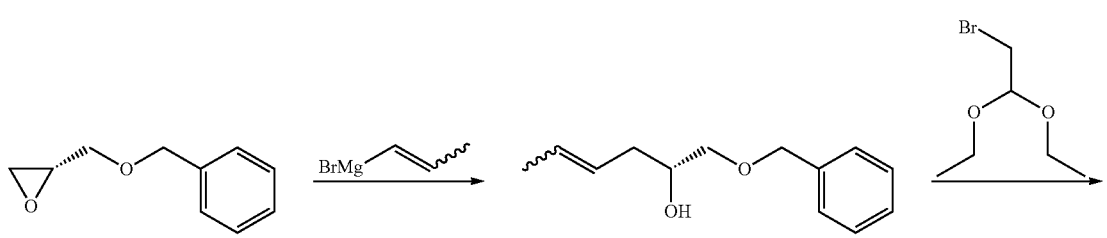

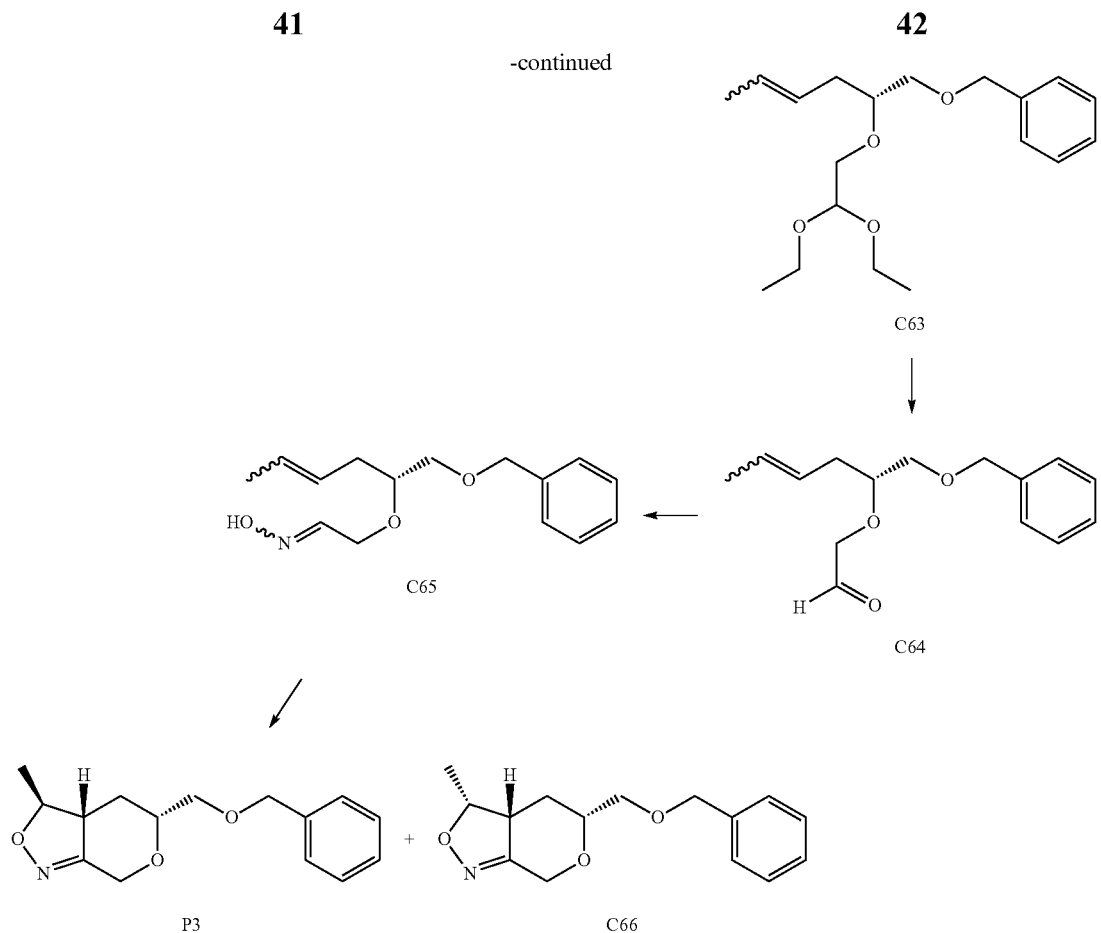

Step 1. Synthesis of (2R)-1-(benzyloxy)hex-4-en-2-ol (C62)

The product was obtained according to the method used for synthesis of C1 in Preparation P1, except that 1-propenylmagnesium bromide was used in place of vinylmagnesium bromide. The product was obtained as a brown oil, which was used without further purification; by $^1$H NMR, this material consisted of a 1:1 mixture of geometric isomers. Yield: 140 g, 0.679 mol, 100%. $^1$H NMR (400 MHz, CDCl$_3$) δ 7.28-7.42 (m, 5H), 5.39-5.67 (m, 2H), 4.57 (s, 2H), 3.80-3.92 (m, 1H), 3.48-3.57 (m, 1H), 3.35-3.43 (m, 1H), 2.36-2.50 (br m, 1H), 2.24-2.33 (m, 1H), 2.17-2.24 (m, 1H), [1.68 (br d, J=6 Hz) and 1.64 (br d, J=7 Hz), total 3H].

Step 2. Synthesis of ({[(2R)-2-(2,2-diethoxyethoxy)hex-4-en-1-yl]oxy}methyl)benzene (C63)

Compound C62 (150 g, 0.73 mol) was converted to the product according to the method used for synthesis of C2 in Preparation P1, except that the initial combination of reagents was carried out at 0° C. The product was obtained as a brown oil (400 g, ≤0.73 mol), which was used for the next step without further purification. By $^1$H NMR analysis, this material contained a roughly 1:1 mixture of geometric isomers. $^1$H NMR (400 MHz, CDCl$_3$), characteristic peaks for product: δ 7.25-7.38 (m, 5H), 5.38-5.60 (m, 2H), 4.55 and 4.55 (2 s, total 2H), 2.22-2.37 (m, 2H), 1.60-1.68 (m, 3H).

Step 3. Synthesis of {[(2R)-1-(benzyloxy)hex-4-en-2-yl]oxy}acetaldehyde (C64)

To a solution of C63 (350 g from the previous step, ≤0.64 mol) in tetrahydrofuran (1.4 L) was added aqueous hydrochloric acid (2 M, 700 mL), and the reaction mixture was stirred at 75° C. for 1 hour. Solvent was removed in vacuo and the aqueous residue was extracted with ethyl acetate (2.0 L). The combined organic layers were washed with saturated aqueous sodium chloride solution (3×500 mL), dried over sodium sulfate, filtered, and concentrated under reduced pressure. The product was obtained as a pale brown oil (210 g, ≤0.64 mol), which was taken directly to the following step.

Step 4. Synthesis of 2-{[(2R)-1-(benzyloxy)hex-4-en-2-yl]oxy}-N-hydroxyethanimine (C65)

To a mixture of C64 (207 g, ≤0.63 mol) and sodium acetate (342 g, 4.17 mol) in aqueous ethanol (2:1 ethanol/water, 2.1 L) was added hydroxylamine hydrochloride (207 g, 2.98 mol). The reaction mixture was stirred at 60° C. for 18 hours, then concentrated in vacuo and extracted with ethyl acetate (2.0 L). The combined organic layers were dried over sodium sulfate, filtered, concentrated under reduced pressure, and purified by chromatography on silica gel (Eluent: ethyl acetate in petroleum ether) to afford the product as a brown oil. By $^1$H NMR, this was assigned as a mixture of geometric isomers at both the oxime and olefin functional groups. Yield: 117 g, 0.444 mol, 70% over three steps. $^1$H NMR (400 MHz, CDCl$_3$), characteristic peaks: δ [7.42-7.48 (m) and 6.88-6.92 (m), total 1H], 7.20-7.36 (m, 5H), 5.29-5.61 (m, 2H), [4.48-4.54 (m) and 4.41-4.45 (m), total 3H], 2.13-2.32 (m, 2H), 1.54-1.65 (m, 3H).

Step 5. Synthesis of (3S,3aR,5R)-5-[(benzyloxy) methyl]-3-methyl-3,3a,4,5-tetrahydro-7H-pyrano[3, 4-c][1,2]oxazole (P3) and (3R,3aR,5R)-5-[(benzyloxy)methyl]-3-methyl-3,3a,4,5-tetrahydro-7H-pyrano[3,4-c][1,2]oxazole (C66)

An aqueous solution of sodium hypochlorite (6.15% solution, 6.6 L) was slowly added to a solution of C65 (660 g, 2.51 mol) and triethylamine (19 g, 0.19 mol) in dichloromethane (6.6 L) at 25° C. After completion of the addition, the reaction mixture was stirred at 25° C. for 30 minutes. The organic layer was washed with water (3×3 L), dried over sodium sulfate, filtered, and concentrated in vacuo; purification via chromatography on silica gel (Eluent: ethyl acetate in petroleum ether) provided (3S,3aR,5R)-5-[(benzyloxy)methyl]-3-methyl-3,3a,4,5-tetrahydro-7H-pyrano[3,4-c][1,2]oxazole (P3) as a white solid. Yield: 90 g, 0.34 mol, 14%. The indicated relative stereochemistry of compound P3 was assigned based on nuclear Overhauser enhancement studies, which revealed interactions of the methine proton on carbon 3a with both the protons of the methyl group on carbon 3 and the methine proton on carbon 5. LCMS m/z 261.9 [M+H+]. $^1$H NMR (400 MHz, CDCl$_3$) δ 7.24-7.39 (m, 5H), 4.69 (d, J=13.7 Hz, 1H), 4.57 (AB quartet, J$_{AB}$=12.2 Hz, Δv$_{AB}$=13.8 Hz, 2H), 4.13-4.25 (m, 2H), 3.62-3.70 (m, 1H), 3.55 (dd, half of ABX pattern, J=10, 6 Hz, 1H), 3.47 (dd, half of ABX pattern, J=10, 4 Hz, 1H), 2.93 (br ddd, J=11, 11, 7 Hz, 1H), 2.11 (br dd, J=12.6, 6.8 Hz, 1H), 1.45-1.56 (m, 1H), 1.45 (d, J=6.2 Hz, 3H).

Also obtained from the chromatographic separation was (3R,3aR,5R)-5-[(benzyloxy)methyl]-3-methyl-3,3a,4,5-tetrahydro-7H-pyrano[3,4-c][1,2]oxazole (C66), as a brown oil. Yield: 126 g, 0.482 mol, 19%. The indicated relative stereochemistry of compound C66 was assigned based on nuclear Overhauser enhancement studies, which revealed interactions of the methine proton on carbon 3a with both the methine proton on carbon 3 and the methine proton on carbon 5. LCMS m/z 261.9 [M+H+]. $^1$H NMR (400 MHz, CDCl$_3$) δ 7.26-7.39 (m, 5H), 4.76-4.86 (m, 1H), 4.75 (d, J=13.5 Hz, 1H), 4.58 (AB quartet, J$_{AB}$=12.2 Hz, Δv$_{AB}$=12.4 Hz, 2H), 4.19 (dd, J=13.5, 1.2 Hz, 1H), 3.63-3.70 (m, 1H), 3.57 (dd, half of ABX pattern, J=10.2, 6.0 Hz, 1H), 3.49 (dd, half of ABX pattern, J=10.1, 4.2 Hz, 1H), 3.36 (br ddd, J=11.4, 11.4, 6.3 Hz, 1H), 1.86 (ddd, J=12.8, 6.4, 1.2 Hz, 1H), 1.55-1.66 (m, 1H), 1.16 (d, J=6.6 Hz, 3H).

Example 1

5-[(4aR,6R,8aS)-2-Amino-6-[(benzyloxy)methyl]-4, 4a,5,6-tetrahydropyrano[3,4-d][1,3]thiazin-8a(8H)-yl]-4-fluoro-2-methoxybenzonitrile (1)

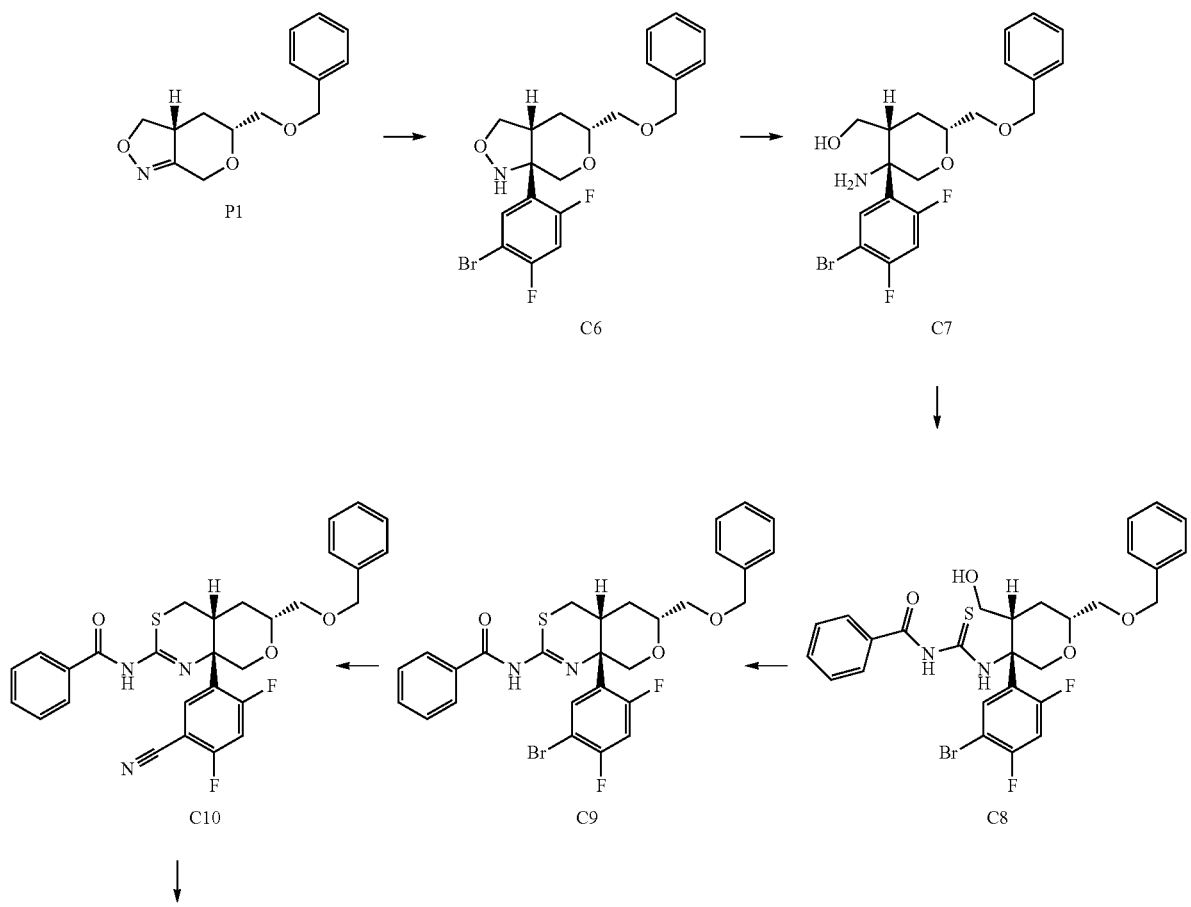

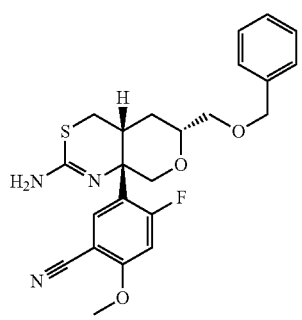

1

Step 1: Synthesis of (3aR,5R,7aS)-5-[(benzyloxy)methyl]-7a-(5-bromo-2,4-difluorophenyl)hexahydro-1H-pyrano[3,4-c][1,2]oxazole (C6)

P1 (4.01 g, 16.5 mmol) was added to a three neck round-bottomed flask (oven dried) equipped with a thermocouple, a nitrogen inlet and mechanical overhead stirrer. Toluene:isopropyl ether (1:1, 160 mL) was added and the resulting solution was cooled to −74° C. Boron trifluoride-diethyl etherate (46.5%, 4.91 ml, 18.5 mmol) was added and the resulting solution was allowed to stir at −74° C. for 30 minutes. 2,4-Difluoro-1,5-di-bromobenzene (5.01 g, 18.4 mmol) was added followed by a slow addition of n-butyllithium (2.5 M in hexanes, 6.96 mL, 17.4 mmol) ensuring the internal temperature did not rise >5° C. The resulting solution was allowed to stir at −78° C. for 90 minutes. Saturated aqueous ammonium chloride (100 mL) was added and the resulting mixture was allowed to warm to room temperature, at which point it was partitioned between ethyl acetate (1×200 mL) and water (1×600 mL). The organic layer was extracted and the aqueous was back extracted with ethyl acetate (3×200 mL). The combined organics were washed with brine (1×100 mL) and the organic layer was dried over sodium sulfate, filtered, and the filtrate concentrated in vacuo. Silica gel chromatography (Gradient 10% to 70% ethyl acetate in heptane) provided the product as a clear oily residue. Yield: 3.11 g, 7.06 mmol, 43%. $^1$H NMR (400 MHz, CD$_3$OD), δ 8.09 (t, J=8.3 Hz, 1H), 7.31-7.36 (m, 4H), 7.25-7.29 (m, 1H), 7.12 (dd, J=11.5, 8.4 Hz, 1H), 4.55 (s, 2H), 4.06 (dd, J=12.6, 1.7 Hz, 1H), 3.78 (d, J=12.5 Hz, 1H), 3.73-3.8 (m, 1H), 3.69 (d, J=7.2 Hz, 1H), 3.53-3.57 (m, 2H), 3.49 (dd, J=7.3, 5.2 Hz, 1H), 3.05-3.11 (m, 1H), 1.82-1.87 (m, 1H), 1.52-1.61 (m, 1H).

Step 2: Synthesis of [(2R,4R,5S)-5-amino-2-((benzyloxy)methyl)-5-(5-bromo-2,4-difluorophenyl)tetrahydro-2H-pyran-4-yl]methanol (C7)

To C6 (1.0 g, 2.27 mmol) in tetrahydrofuran (1 mL) cooled to 0° C. was added a tetrahydrofuran solution of samarium iodide (0.1 M, 90.8 mL, 9.08 mmol) in a drop-wise manner. The resulting solution was allowed to stir at room temperature for 90 minutes. A saturated aqueous solution of sodium thiosulfate pentahydrate (1 L) was added to the reaction, followed by extraction with ethyl acetate (3×250 mL). The combined organics were washed with brine (1×500 mL), dried over sodium sulfate, filtered and concentrated in vacuo to afford a clear oily residue. The residue was dissolved in dichloromethane (5 mL) and filtered through a silica gel plug (approx 100 g) with dichloromethane (3×100 mL). The combined filtrates were concentrated in vacuo to afford the product as a clear oily residue, which was used directly in the next step. Yield: 947 mg, 2.14 mmol, 94%. LCMS m/z 443.1 [M+H$^+$], Br isotopic pattern. $^1$H NMR (400 MHz, CD$_3$OD), characteristic peaks: δ 8.00 (t, J=8.1 Hz, 1H), 7.24-7.38 (m, 5H), 7.10 (dd, J=12.1, 8.4 Hz, 1H), 4.58 (s, 2H), 4.03 (dd, J=11.2, 2.2 Hz, 1H), 3.72-3.80 (m, 1H), 3.56-3.64 (m, 2H), 3.44 (d, J=11.3 Hz, 1H), 3.34, (d, J=5.1 Hz, 1H), 2.46-2.53 (m, 1H), 1.68-1.80 (m, 2H).

Step 3: Synthesis of N-[((3S,4R,6R)-6-((benzyloxy)methyl)-3-(5-bromo-2,4-difluorophenyl)-4-(hydroxymethyl)tetrahydro-2H-pyran-3-yl)carbamothioyl]benzamide (C8)

To C7 (0.946 g, 2.14 mmol) in dichloromethane (22 mL) was added benzoyl isothiocyanate (0.273 mL, 2.04 mmol) and the resulting solution was allowed to stir at room temperature for 18 hours. The reaction mixture was concentrated in vacuo, providing the product as an orange oily residue, which was carried forward into the next step without further purification. Yield: 964 mg, 1.59 mmol, 74%. LCMS m/z 607.6 [M+H$^+$], Br isotopic pattern. $^1$H NMR (400 MHz, CD$_3$OD), characteristic peaks: δ 7.89-7.90 (m, 2H), 7.62-7.66 (m, 2H), 7.50-7.54 (m, 2H), 7.31 (d, J=6.6 Hz, 2H), 7.18-7.25 (m, 2H), 7.06 (dd, J=11.9, 8.8 Hz, 2H), 4.52-4.59 (m, 2H), 3.84-3.90 (m, 3H), 3.55-3.64 (m, 3H), 3.45-4.51 (m, 1H) 1.90-1.99 (m, 3H).

Step 4: Synthesis of N-[(6R)-6-[(benzyloxy)methyl]-8a-(5-bromo-2,4-difluorophenyl)-4,4a,5,6,8,8a-hexahydropyrano[3,4-d][1,3]thiazin-2-yl]benzamide (C9)

A solution of C8 (0.964 g, 1.59 mmol) and pyridine (0.487 ml, 6.05 mmol) in dichloromethane (27.0 mL) was cooled to −50° C. internal temperature. Trifluoromethanesulfonic anhydride (0.535 mL, 3.18 mmol) was added drop-wise to the solution and the mixture was gradually warmed to 0° C. and allowed to stir at that temperature for 3.5 hours. The reaction mixture was partitioned between dichloromethane (250 mL) and water (250 mL). The organic layer was removed and washed with water (2×300 mL) and brine (1×250 mL), then dried over magnesium sulfate, filtered and concentrated in vacuo. Silica gel chromatography (Gradient 0% to 50% ethyl acetate in heptane) provided the product as a white solid. Yield: 822 mg, 1.40 mmol, 88%. LCMS m/z 589.6 [M+H$^+$], Br isotopic pattern. $^1$H NMR (400 MHz, CD$_3$OD), characteristic peaks: δ 8.05-8.16 (m, 2H), 7.62 (t, J=7.9 Hz, 1H), 7.61-7.67 (m, 1H), 7.42-7.49 (m, 2H), 7.28-7.33 (m, 2H), 7.16-7.25 (m, 3H), 4.58 (d, J=11.7 Hz, 1H), 4.52 (d, J=11.7 Hz, 1H), 4.07 (dd, J=11.9, 1.6 Hz, 1H), 3.89 (br d, J=11.9 Hz, 2H), 3.54-3.62 (m, 2H), 3.11-3.18 (m, 1H), 2.96 (dd, J=13.2, 4.2 Hz, 1H), 2.74 (dd, J=13.2, 2.8 Hz, 1H), 1.88-1.98 (m, 1H), 1.69 (d, J=11.7 Hz, 1H).

Step 5: Synthesis of N-[(6R)-6-[(benzyloxy)methyl]-8a-(5-cyano-2,4-difluorophenyl)-4,4a,5,6,8,8a-hexahydropyrano[3,4-d][1,3]thiazin-2-yl]benzamide (C10)

C9 (300 mg, 0.511 mmol), zinc cyanide (72.0 mg, 0.613 mmol), tetrakis(triphenylphosphine)palladium(0) (342 mg, 0.296 mmol) and N,N-dimethylformamide (9 mL) were added to a 16 ml Emry microwave vial. The vial was sealed and purged with nitrogen for 10 minutes while stirring. The reaction was heated at 80° C. in a Biotage microwave for 120 minutes. The reaction mixture was partitioned between ethyl acetate (100 mL) and saturated aqueous sodium bicarbonate (200 mL). The organic was separated and the aqueous layer was extracted with ethyl acetate (3×50 mL). The combined organics were washed with brine (1×200 mL), dried over sodium sulfate, filtered, and absorbed on silica gel. The obtained solid after removal of solvent was subjected to silica gel chromatography (Gradient: 0% to 100% ethyl acetate in heptane) to provide the desired product as a yellow solid. Yield: 269 mg, 0.503 mmol, 98%. LCMS m/z 534.3 [M+H$^+$].

Step 6: Synthesis of 5-[(4aR,6R,8aS)-2-amino-6-[(benzyloxy)methyl]-4,4a,5,6-tetrahydropyrano[3,4-d][1,3]thiazin-8a(8H)-yl]-4-fluoro-2-methoxybenzonitrile (1)

To a solution of C10 (30.0 mg, 0.056 mmol) in methanol (2 mL) was added 1,8-diazabicycloundec-7-ene (6 μL, 0.039 mmol) and the resulting solution was heated to reflux for 18 hours. The reaction mixture was cooled to room temperature and concentrated in vacuo. Silica gel chromatography (Gradient 0% to 20% methanol in dichloromethane) provided the product as a yellow solid. Yield: 16.6 mg, 0.037 mmol, 66%. LCMS m/z 442.2 [M+H$^+$]. $^1$H NMR (400 MHz, CD$_3$OD), δ 7.48 (d, J=8.6 Hz, 1H), 7.29-7.35 (m, 4H), 7.24-7.27 (m, 1H), 7.02 (d, J=14.2 Hz, 1H), 4.57 (d, J=11.9 Hz, 1H), 4.53 (d, J=11.9 Hz, 1H), 4.02 (dd, J=11, 2.4 Hz, 1H), 3.78-3.84 (m, 1H), 3.66 (d, J=11.1 Hz, 1H), 3.47-3.57 (m, 4H), 2.83-2.89 (m, 2H), 2.65-2.69 (m, 1H), 1.73-1.82 (m, 1H), 1.50-1.55 (m, 1H), 1.50-1.55 (m, 2H).

Example 2

5-[(4aR,6R,8aS)-2-Amino-6-[(benzyloxy)methyl]-4,4a,5,6-tetrahydropyrano[3,4-d][1,3]thiazin-8a(8H)-yl]-2,4-difluorobenzonitrile (2)

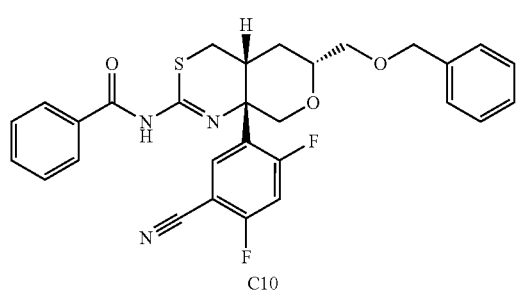

Step 1: Synthesis of 5-[(4aR,6R,8aS)-2-amino-6-[(benzyloxy)methyl]-4,4a,5,6-tetrahydropyrano[3,4-d][1,3]thiazin-8a(8H)-yl]-2,4-difluorobenzonitrile (2)

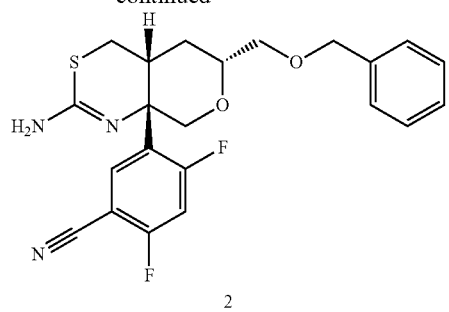

To a solution of C10 (30.0 mg, 0.056 mmol) in absolute ethanol (0.5 mL) was added hydrazine monohydrate (0.030 mL, 0.392 mmol) and the resulting solution was allowed to stir at room temperature for 45 minutes. The reaction mixture was concentrated in vacuo. Silica gel chromatography (Gradient 0% to 10% methanol in dichloromethane) provided the desired product as a yellow solid. Yield: 8.00 mg, 0.017 mmol, 30%. LCMS m/z 430.2 [M+H$^+$]. $^1$H NMR (400 MHz, CD$_3$OD), characteristic peaks: δ 4.52-4.59 (m, 2H), 4.02 (dd, J=11.4, 2.2 Hz, 1H), 3.82-3.86 (m, 1H), 3.72 (d, J=11.5 Hz, 1H), 2.76 (dd, J=12.8, 2.6 Hz, 1H), 1.75-1.83 (m, 1H), 1.57-1.62 (m, 1H).

Example 3

5-[(4aR,6R,8aS)-2-Amino-6-(hydroxymethyl)-4,4a,5,6-tetrahydropyrano[3,4-d][1,3]thiazin-8a(8H)-yl]-2,4-difluorobenzonitrile (3)

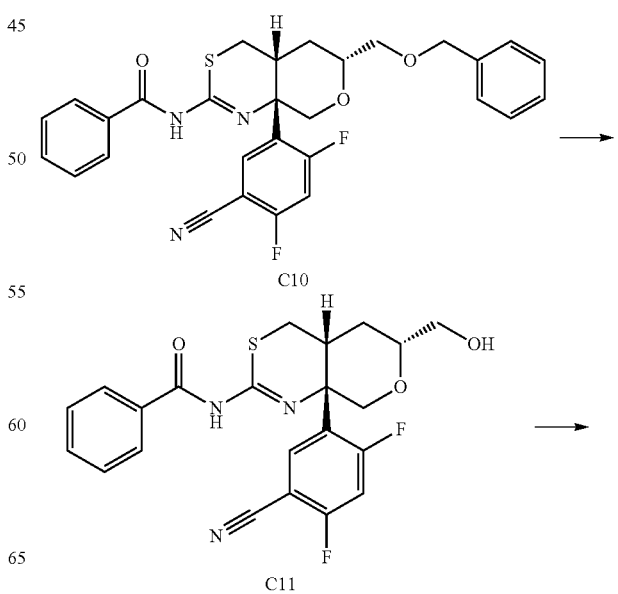

-continued

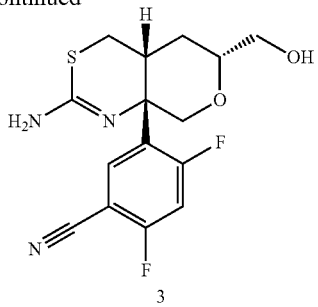

3

Step 1: Synthesis of N-[(6R)-8a-(5-cyano-2,4-difluorophenyl)-6-(hydroxymethyl)-4,4a,5,6,8,8a-hexahydropyrano[3,4-d][1,3]thiazin-2-yl]benzamide (C11)

To a solution of C10 (180 mg, 0.337 mmol) in dichloromethane (2 mL) cooled to −10° C. was added boron trichloride (1.52 mL, 1.52 mmol) drop-wise. The resulting solution was allowed to stir at −10° C. for 3 hours. Methanol (15 mL) was added and the reaction was concentrated in vacuo. Methanol (15 mL) was added to the residue and the solution was concentrated in vacuo. The process was then repeated. The residue was flushed through a plug of silica gel with a 9:1 mixture of dichloromethane/methanol (3×50 mL). The filtrates were combined and concentrated in vacuo to provide the desired product as a yellow solid. Yield: 161 mg, 0.364 mmol, 108%. LCMS m/z 444.1 [M+H⁺]. ¹H NMR (400 MHz, CD₃OD), δ 8.07 (br s, 2H), 7.85 (t, J=6.8 Hz, 1H), 7.54-7.57 (m, 1H), 7.45-7.49 (m, 2H), 7.38 (dd, J=12.1, 9.2 Hz, 1H), 4.06 (dd, J=11.4, 1.7 Hz, 1H), 3.9 (d, J=11.9 Hz, 1H), 3.70-3.77 (m, 1H), 3.57 (d, J=5.3 Hz, 2H), 3.09-3.17 (m, 1H), 2.96 (dd, J=12.9, 4.1 Hz, 1H), 2.75 (dd, J=13.2, 2.8 Hz, 1H), 1.78-1.88 (m, 1H), 1.64-1.71 (m, 1H).

Step 2: Synthesis of 5-[(4aR,6R,8aS)-2-amino-6-(hydroxymethyl)-4,4a,5,6-tetrahydropyrano[3,4-d][1,3]thiazin-8a(8H)-yl]-2,4-difluorobenzonitrile (3)

N-[(6R)-8a-(5-Cyano-2,4-difluorophenyl)-6-(hydroxymethyl)-4,4a,5,6,8,8a-hexahydropyrano[3,4-d][1,3]thiazin-2-yl]benzamide (C11) was converted to the product using the method described for the synthesis of 5-[(4aR,6R,8aS)-2-amino-6-[(benzyloxy)methyl]-4,4a,5,6-tetrahydropyrano[3,4-d][1,3]thiazin-8a(8H)-yl]-2,4-difluorobenzonitrile (2) in Example 2. Yield: 14.2 mg, 0.042 mmol, 62%. LCMS m/z 340.1 [M+H⁺]. ¹H NMR (400 MHz, CD₃OD), δ 7.64 (t, J=7.9 Hz, 1H), 7.30 (dd, J=12.1, 9.2 Hz, 1H), 4.02 (dd, J=11.1, 2.5 Hz, 1H), 3.64-3.70 (m, 2H), 3.50-3.58 (m, 2H), 2.85-2.93 (m, 2H), 2.68-2.72 (m, 1H), 1.68-1.78 (m, 1H), 1.50-1.55 (m, 1H).

Example 4

5-[(4aR,6R,8aS)-2-Amino-6-(fluoromethyl)-4,4a,5,6-tetrahydropyrano[3,4-d][1,3]thiazin-8a(8H)-yl]-2,4-difluorobenzonitrile (4)

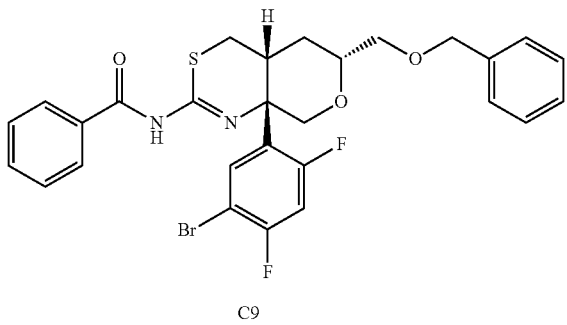

C9

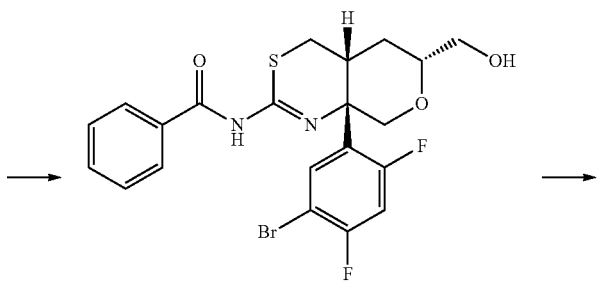

C12

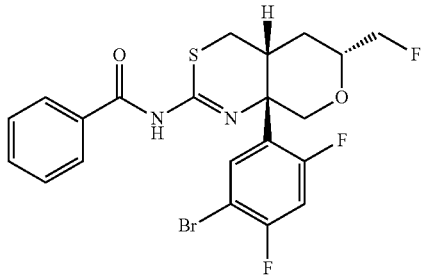

C13

↓ Zn(CN)₂

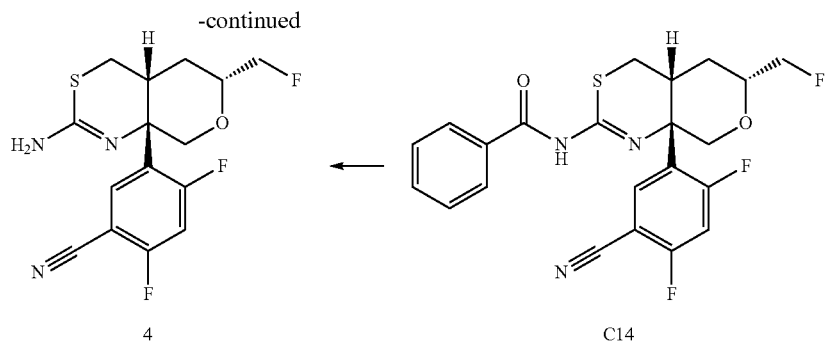

Step 1: Synthesis of N-[(4aR,6R,8aS)-8a-(5-bromo-2,4-difluorophenyl)-6-(hydroxymethyl)-4,4a,5,6,8,8a-hexahydropyrano[3,4-d][1,3]thiazin-2-yl]benzamide (C12)

A solution of C9 (3.22 g, 5.48 mmol) in ethyl acetate (100 mL) was treated with a solution of sodium bromate (4.14 g, 27.4 mmol) in water (66 mL). To the well stirred biphasic system was added a solution of sodium dithionite (4.77 g, 27.4 mmol) in water (134 mL) drop-wise over 30 minutes. The reaction mixture was stirred for 90 minutes and then diluted with ethyl acetate (500 mL). The organic layer was removed and the aqueous was extracted with ethyl acetate (3×100 mL). The combined organics were then washed with an aqueous solution of sodium thiosulfate pentahydrate (3×300 mL), brine (300 mL), and then dried over sodium sulfate, filtered and concentrated in vacuo. Silica gel chromatography (Gradient: 0% to 100% ethyl acetate in heptane) provided the product as a white solid. Yield: 1.77 g, 3.57 mmol, 65%. LCMS m/z 499.1 [M+H⁺], Br isotopic pattern. $^1$H NMR (400 MHz, CD$_3$OD), characteristic peaks: δ 8.11 (d, J=6.5 Hz, 2H), 7.64 (t, J=7.9 Hz, 1H), 7.53-7.57 (m, 1H), 7.44-7.48 (m, 2H), 7.24 (dd, J=12, 8.3 Hz, 1H), 4.09 (dd, J=11.6, 1.9 Hz, 1H), 3.9 (d, J=11.9 Hz, 1H), 3.72-3.77 (m, 1H), 3.58 (d, J=5.1 Hz, 2H), 3.11-3.19 (m, 1H), 2.97 (dd, J=13.3, 4.1 Hz, 1H), 2.75 (dd, J=13.1, 2.7 Hz, 1H), 1.84 (q, J=11.6 Hz, 1H), 1.66-1.71 (m, 1H).

Step 2: Synthesis of N-[(4aR,6R,8aS)-8a-(5-bromo-2,4-difluorophenyl)-6-(fluoromethyl)-4,4a,5,6,8,8a-hexahydropyrano[3,4-d][1,3]thiazin-2-yl]benzamide (C13)

Diethylaminosulfur trifluoride (0.860 g, 5.34 mmol) was added to a solution of pentanes (70 mL) and dichloromethane (35 mL). To the resulting clear solution was added a solution of C12 (1.77 g, 3.56 mmol) in dichloromethane (71 mL) in a drop-wise manner and the mixture was allowed to stir at room temperature for 16 hours. Aqueous saturated sodium bicarbonate solution (200 mL) was added and the aqueous was extracted with dichloromethane (3×200 mL). The combined organics were washed with brine (200 mL), dried over magnesium sulfate, filtered and concentrated. Silica gel chromatography (Gradient: 0% to 100% ethyl acetate in heptane) provided 1.5 g of a white solid, which was triturated with diethyl ether (20 mL) to provide the product as a white solid. Yield: 1.10 g, 2.20 mmol, 62%. LCMS m/z 501.0 [M+H⁺], Br isotopic pattern. $^1$H NMR (400 MHz, CD$_3$OD), δ 8.09 (br s, 2H), 7.64 (t, J=8.0 Hz, 1H), 7.53-7.56 (m, 1H), 7.44-7.48 (m, 2H), 7.23 (dd, J=12.1, 8.4 Hz, 1H), 4.47-4.49 (m, 1H), 4.35-4.37 (m, 1H), 4.1 (dd, J=11.7, 1.6 Hz, 1H), 3.94-4.01 (m, 1H), 3.9 (d, J=11.7 Hz, 1H), 3.13-3.21 (m, 1H), 2.96 (dd, J=13.2, 4.2 Hz, 1H), 2.75 (dd, J=13.4, 2.8 Hz, 1H), 1.88 (q, J=12.1 Hz, 1H), 1.63-1.71 (m, 1H).

Step 3: Synthesis of N-[(4aR,6R,8aS)-8a-(5-cyano-2,4-difluorophenyl)-6-(fluoromethyl)-4,4a,5,6,8,8a-hexahydropyrano[3,4-d][1,3]thiazin-2-yl]benzamide (C14)

N-[(4aR,6R,8aS)-8a-(5-Bromo-2,4-difluorophenyl)-6-(fluoromethyl)-4,4a,5,6,8,8a-hexahydropyrano[3,4-d][1,3]thiazin-2-yl]benzamide (C13) was converted to the product using the method described for the synthesis of N-[(6R)-6-[(benzyloxy)methyl]-8a-(5-cyano-2,4-difluorophenyl)-4,4a,5,6,8,8a-hexahydropyrano[3,4-d][1,3]thiazin-2-yl]benzamide (C10) in Example 1. Yield: 98.5 mg, 0.220 mmol, 44%. LCMS m/z 446.2 [M+H⁺]. $^1$H NMR (400 MHz, CD$_3$OD), δ 8.06 (d, J=7.2 Hz, 2H), 7.85 (t, J=7.8 Hz, 1H), 7.54-7.57 (m, 1H), 7.45-7.49 (m, 2H), 7.37 (dd, J=12.1, 9.2 Hz, 1H), 4.44-4.51 (m, 1H), 4.32-4.39 (m, 1H), 4.06-4.10 (m, 1H), 3.89-4.0 (m, 2H), 3.11-3.19 (m, 1H), 2.96 (dd, J=13.3, 4.1 Hz, 1H), 2.75 (dd, J=13.3, 2.9 Hz, 1H), 1.83-1.93 (m, 1H), 1.64-1.69 (m, 1H).

Step 4: Synthesis of 5-[(4aR,6R,8aS)-2-amino-6-(fluoromethyl)-4,4a,5,6-tetrahydropyrano[3,4-d][1,3]thiazin-8a(8H)-yl]-2,4-difluorobenzonitrile (4)

N-[(4aR,6R,8aS)-8a-(5-Cyano-2,4-difluorophenyl)-6-(fluoromethyl)-4,4a,5,6,8,8a-hexahydropyrano[3,4-d][1,3]thiazin-2-yl]benzamide (C14) was converted to the product using the method described for the synthesis of 5-[(4aR,6R,8aS)-2-amino-6-[(benzyloxy)methyl]-4,4a,5,6-tetrahydropyrano[3,4-d][1,3]thiazin-8a(8H)-yl]-2,4-difluorobenzonitrile (2) in Example 2. Yield: 67.0 mg, 0.197 mmol, 88%. LCMS m/z 342.2 [M+H⁺]. $^1$H NMR (400 MHz, CD$_3$OD), δ 7.64 (t, J=7.9 Hz, 1H), 7.31 (dd, J=12.1, 9.2 Hz, 1H), 4.41-4.48 (m, 1H), 4.29-4.36 (m, 1H), 4.04 (dd, J=11, 2.4 Hz, 1H), 3.83-3.93 (m, 1H), 3.69 (d, J=11.1 Hz, 1H), 2.86-2.97 (m, 2H), 2.69-2.73 (m, 1H), 1.82 (qd, J=12.4, 2.7 Hz, 1H), 1.52 (ddd, J=13.2, 4.2, 2.5 Hz, 1H).

Example 5

5-[(4aR,6R,8aS)-2-Amino-6-(methoxymethyl)-4,4a,5,6-tetrahydropyrano[3,4-d][1,3]thiazin-8a(8H)-yl]-2,4-difluorobenzonitrile (5)

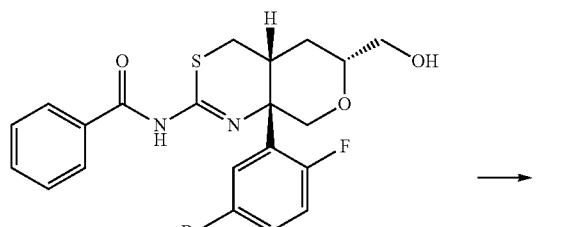

C12

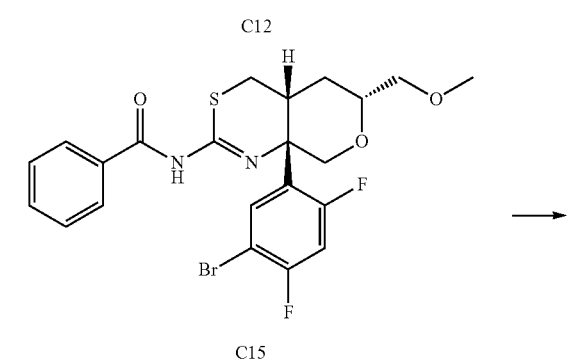

C15

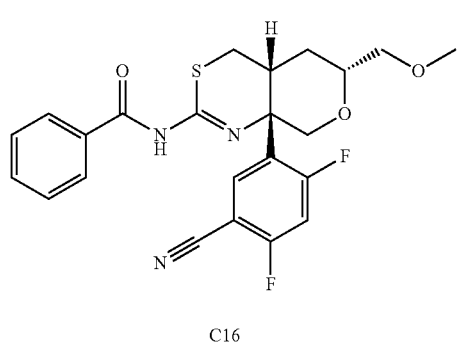

C16

↓

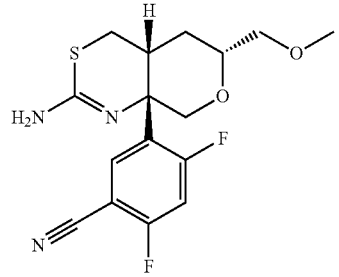

5

Step 1: Synthesis of N-[(4aR,6R,8aS)-8a-(5-bromo-2,4-difluorophenyl)-6-(methoxymethyl)-4,4a,5,6,8,8a-hexahydropyrano[3,4-d][1,3]thiazin-2-yl]benzamide (C15)

To C12 (100 mg, 0.201 mmol) in tetrahydrofuran (4 mL) was added sodium hydride (60% in mineral oil, 22 mg, 0.54 mmol) and the reaction was allowed to stir at room temperature for 30 minutes. Methyl iodide (16.7 µL, 0.270 mmol) was added and the reaction was allowed to stir at room temperature for 16 hours. Saturated aqueous sodium bicarbonate was added (50 mL) and the aqueous was extracted with ethyl acetate (3×20 mL). The combined organics were washed with brine (10 mL), dried over sodium sulfate, filtered and concentrated in vacuo to provide the product as a yellow solid. This was used in the next step without further purification. Yield: 98.0 mg, 0.191 mmol, 95%. LCMS m/z 513.1 [M+H$^+$], Br isotope.

Step 2: Synthesis of N-[(4aR,6R,8aS)-8a-(5-cyano-2,4-difluorophenyl)-6-(methoxymethyl)-4,4a,5,6,8,8a-hexahydropyrano[3,4-d][1,3]thiazin-2-yl]benzamide (C16)

N-[(4aR,6R,8aS)-8a-(5-Bromo-2,4-difluorophenyl)-6-(methoxymethyl)-4,4a,5,6,8,8a-hexahydropyrano[3,4-d][1,3]thiazin-2-yl]benzamide (C15) was converted to the product using the method described for the synthesis of N-[(6R)-6-[(benzyloxy)methyl]-8a-(5-cyano-2,4-difluorophenyl)-4,4a,5,6,8,8a-hexahydropyrano[3,4-d][1,3]thiazin-2-yl]benzamide (C10) in Example 1. Yield: 92.0 mg, 0.209 mmol, 110%. LCMS m/z 458.2 [M+H$^+$].

Step 3: Synthesis of 5-[(4aR,6R,8aS)-2-amino-6-(methoxymethyl)-4,4a,5,6-tetrahydropyrano[3,4-d][1,3]thiazin-8a(8H)-yl]-2,4-difluorobenzonitrile (5)

N-[(4aR,6R,8aS)-8a-(5-Cyano-2,4-difluorophenyl)-6-(methoxymethyl)-4,4a,5,6,8,8a-hexahydropyrano[3,4-d][1,3]thiazin-2-yl]benzamide (C16) was converted to the product using the method described for the synthesis of 5-[(4aR,8aS)-2-amino-6-[(benzyloxy)methyl]-4,4a,5,6-tetrahydropyrano[3,4-d][1,3]thiazin-8a(8H)-yl]-2,4-difluorobenzonitrile (2) in Example 2. Yield: 13.2 mg, 38.0 µmol, 19%. LCMS m/z 354.2 [M+H$^+$]. $^1$H NMR (400 MHz, CD$_3$OD), δ 7.64 (t, J=7.8 Hz, 1H), 7.3 (dd, J=12, 9.1 Hz, 1H), 4.01 (dd, J=11.1, 2.5 Hz, 1H), 3.76-3.82 (m, 1H), 3.66 (d, J=11.1 Hz, 1H), 3.45 (dd, J=10.3, 6.4 Hz, 1H), 3.39 (dd, J=10.3, 3.9 Hz, 1H), 3.36 (s, 3H), 2.84-2.92 (m, 2H), 2.67-2.71 (m, 1H), 1.70-1.80 (m, 1H), 1.50-1.55 (m, 1H).

Example 6

3-[(4aR,6S,8aS)-2-Amino-6-methyl-4,4a,5,6-tetrahydropyrano[3,4-d][1,3]thiazin-8a(8H)-yl]-4-chlorobenzonitrile (6)

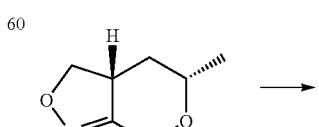

P2

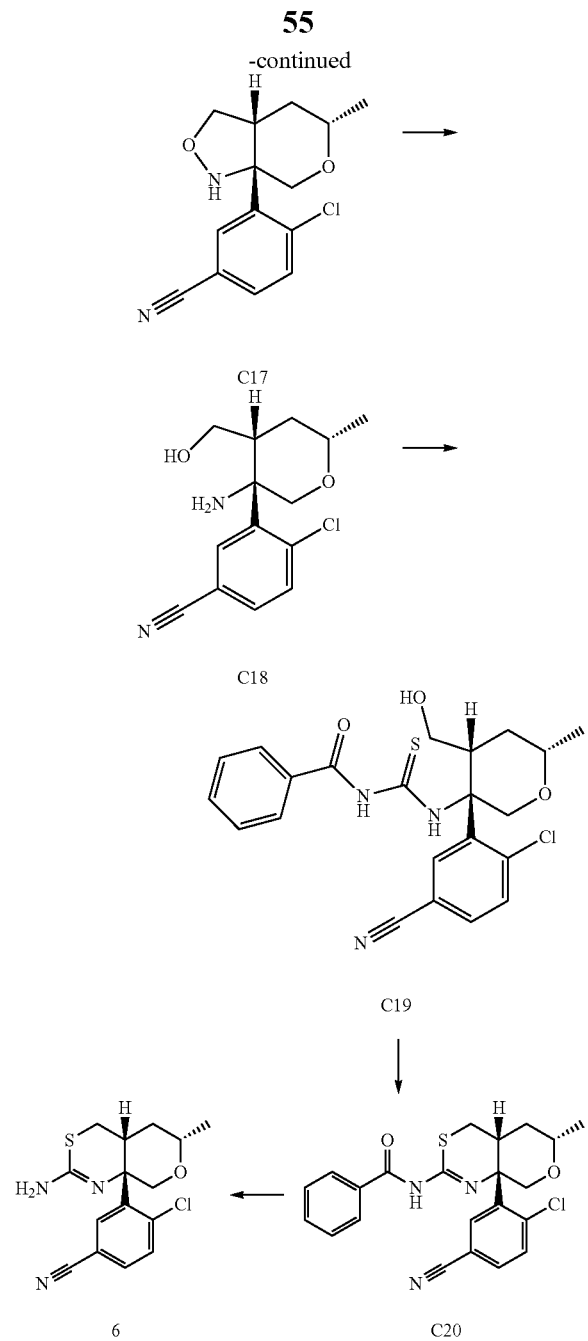

Step 1: Synthesis of 4-chloro-3-[(3aR,5S,7aS)-5-methyltetrahydro-1H-pyrano[3,4-c][1,2]oxazol-7a(7H)-yl]benzonitrile (C17)

To P2 (55 mg, 0.39 mmol) in toluene (3 mL) cooled to −78° C. was added boron trifluoride-diethyl etherate (46.5%, 95 μL, 0.437 mmol). The reaction was then allowed to warm to room temperature for 30 minutes at which point 3-bromo-4-chlorobenzonitrile (106 mg, 0.488 mmol) was added as a solid. Once the solution became homogenous it was cooled to −78° C. at which point tert-butyllithium (1.7 M solution in pentanes, 0.514 mL, 0.874 mmol) was added drop-wise. The reaction was allowed to stir at −78° C. for 20 minutes followed by addition of saturated aqueous ammonium chloride solution (3 mL) and dichloromethane (6 mL). The reaction was warmed to room temperature, and the organics were separated, dried over sodium sulfate, and concentrated in vacuo. The residue was carried into the next step without further purification. Yield: 75 mg, 0.266 mmol, 68%.

LCMS m/z 281.1 [M+H$^+$] Cl isotope pattern.

Step 2: Synthesis of 3-[(3S,4R,6S)-3-amino-4-(hydroxymethyl)-6-methyltetrahydro-2H-pyran-3-yl]-4-chlorobenzonitrile (C18)

To crude C17 (75.0 mg, 0.270 mmol) in glacial acetic acid (1 mL) was added zinc dust (30.0 mg, 0.458 mmol). The reaction was stirred at room temperature for 1 hour at which point dichloromethane (10 mL) was added. The reaction mixture was then filtered through a pad of Celite and the filtrate was concentrated in vacuo. The residue was taken up in methanol (1 mL) and loaded onto an Oasis® MCX cation exchange solid-phase extraction cartridge (Waters, 12 mL, 1 g bed weight) and washed with dichloromethane (30 mL) and methanol (30 mL). The product was eluted from the column with a solution of ammonia in methanol (2 M, 20 mL) and the filtrate was concentrated in vacuo to provide product that was utilized in the next step without additional purification. Yield: 35.0 mg, 0.124 mmol, 46%.

Step 3: Synthesis of N-{[(3S,4R,6S)-3-(2-chloro-5-cyanophenyl)-4-(hydroxymethyl)-6-methyltetrahydro-2H-pyran-3-yl]carbamothioyl}benzamide (C19)

To crude C18 (35.0 mg, 0.124 mmol) in dichloromethane (3 mL) was added benzoyl isothiocyanate (16.0 μL, 0.125 mmol) and the reaction was allowed to stir at room temperature for 22 hours. The reaction mixture was concentrated in vacuo to provide the product as a yellow oily residue, which was used in the subsequent step without further purification. Yield: 60.0 mg, 0.131 mmol, 109%. LCMS m/z 442.2 [M−H$^+$].

Step 4: Synthesis of N-[(4aR,6S,8aS)-8a-(2-chloro-5-cyanophenyl)-6-methyl-4,4a,5,6,8,8a-hexahydropyrano[3,4-d][1,3]thiazin-2-yl]benzamide (C20)

To a solution of C19 (60.0 mg, 0.134 mmol) and pyridine (41 μL, 0.51 mmol) in dichloromethane (2.31 mL) cooled to −78° C. was added trifluoromethanesulfonic anhydride (45 μL, 0.27 mmol) drop-wise. The reaction mixture was gradually warmed to 0° C. over 3 hours at which point water (1 mL) was added. The aqueous was extracted with dichloromethane (2×2 mL). The combined organics were dried over sodium sulfate, filtered and concentrated in vacuo. Silica gel chromatography (Gradient: 0% to 100% ethyl acetate in heptane) provided the product as a yellow residue. Yield: 16.0 mg, 38.0 μmol, 28%. LCMS m/z 426.2 [M+H$^+$], Cl isotope pattern.

Step 5: Synthesis of 3-[(4aR,6S,8aS)-2-amino-6-methyl-4,4a,5,6-tetrahydropyrano[3,4-d][1,3]thiazin-8a(8H)-yl]-4-chlorobenzonitrile (6)

To a solution of C20 (16 mg, 38 μmol) in ethanol (1 mL) was added hydrazine monohydrate (20 μL, 0.27 mmol). The reaction was stirred at room temperature for 1 hour at which point the reaction mixture was concentrated in vacuo, dissolved in dimethyl sulfoxide (0.9 mL) and purified by reverse phase HPLC (Column: Waters XBridge C18, 19×100 mm, 5 μm; Mobile phase A: 0.03% ammonium hydroxide in water (v/v); Mobile phase B: 0.03% ammonium hydroxide in acetonitrile (v/v); Gradient: 20% to 50% B, linear over 8.5 minutes). Post purification QC conditions: (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute). Yield 1.80 mg, 4.44 μmol, 12%. LC/MS m/z 322.2 [M+H$^+$], Cl isotope pattern. Analytical retention time: 1.8 minutes.

Example 7

3-[(4aR,6S,8aS)-2-Amino-6-methyl-4,4a,5,6-tetrahydropyrano[3,4-d][1,3]thiazin-8a(8H)-yl]benzonitrile (7)

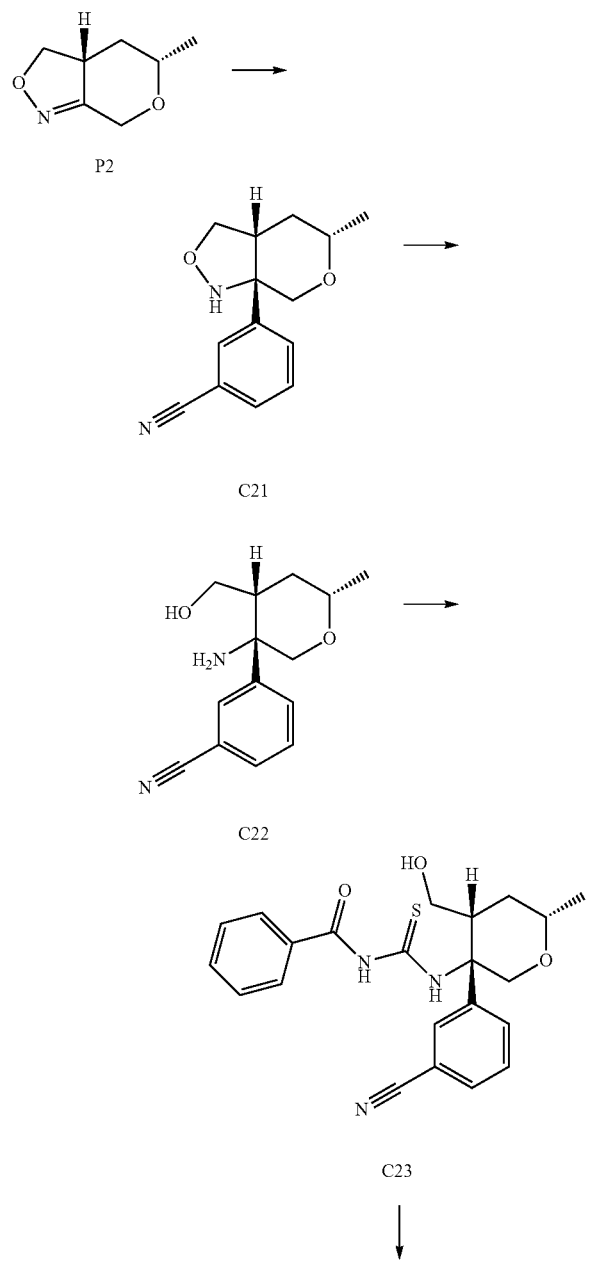

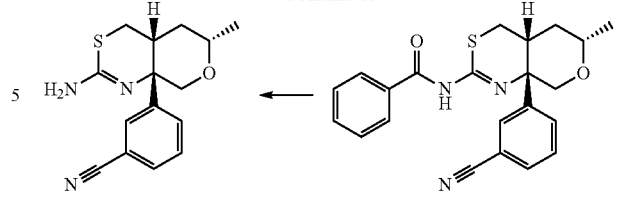

Step 1: Synthesis of 3-[(3aR,5S,7aS)-5-methyltetrahydro-1H-pyrano[3,4-c][1,2]oxazol-7a(7H)-yl]benzonitrile (C21)

P2 was converted to the product using the method described for the synthesis of 4-chloro-3-[(3aR,5S,7aS)-5-methyltetrahydro-1H-pyrano[3,4-c][1,2]oxazol-7a(7H)-yl]benzonitrile (C17) in Example 6. The resulting product was used in the next step without further purification. Yield: 173 mg, 0.708 mmol, 100%. GCMS m/z 244 [M$^+$].

Step 2: Synthesis of 3-[(3S,4R,6S)-3-amino-4-(hydroxymethyl)-6-methyltetrahydro-2H-pyran-3-yl]benzonitrile (C22)

3-[(3aR,5S,7aS)-5-Methyltetrahydro-1H-pyrano[3,4-c][1,2]oxazol-7a(7H)-yl]benzonitrile (C21) was converted to the product using the method described for the synthesis of 3-[(3S,4R,6S)-3-amino-4-(hydroxymethyl)-6-methyltetrahydro-2H-pyran-3-yl]-4-chlorobenzonitrile (C18) in Example 6. The resulting product was used in the next step without further purification. Yield: 105 mg, 0.426 mmol, 60%. LCMS m/z 247.1 [M+H$^+$].

Step 3: Synthesis of N-{[(3S,4R,6S)-3-(3-cyanophenyl)-4-(hydroxymethyl)-6-methyltetrahydro-2H-pyran-3-yl]carbamothioyl}benzamide (C23)

3-[(3S,4R,6S)-3-Amino-4-(hydroxymethyl)-6-methyltetrahydro-2H-pyran-3-yl]benzonitrile (C22) was converted to the product using the method described for the synthesis of N-{[(3S,4R,6S)-3-(2-chloro-5-cyanophenyl)-4-(hydroxymethyl)-6-methyltetrahydro-2H-pyran-3-yl]carbamothioyl}benzamide (C19) in Example 6. The resulting product was used in the next step without further purification. Yield: 118 mg, 0.288 mmol, 68%. LCMS m/z 410.2 [M+H$^+$].

Step 4: Synthesis of N-[(4aR,6S,8aS)-8a-(3-cyanophenyl)-6-methyl-4,4a,5,6,8,8a-hexahydropyrano[3,4-d][1,3]thiazin-2-yl]benzamide (C24)

N-{[(3S,4R,6S)-3-(3-Cyanophenyl)-4-(hydroxymethyl)-6-methyltetrahydro-2H-pyran-3-yl]carbamothioyl}benzamide (C23) was converted to the product using the method described for the synthesis of N-[(4aR,6S,8aS)-8a-(2-chloro-5-cyanophenyl)-6-methyl-4,4a,5,6,8,8a-hexahydropyrano[3,4-d][1,3]thiazin-2-yl]benzamide (C20) in Example 6. The resulting product was used in the next step without further purification. Yield: 45.0 mg, 0.115 mmol, 40%. LCMS m/z 392.2 [M+H$^+$].

Step 5: Synthesis of 3-[(4aR,6S,8aS)-2-amino-6-methyl-4,4a,5,6-tetrahydropyrano[3,4-d][1,3]thiazin-8a(8H)-yl]benzonitrile (7)

N-[(4aR,6S,8aS)-8a-(3-Cyanophenyl)-6-methyl-4,4a,5,6,8,8a-hexahydropyrano[3,4-d][1,3]thiazin-2-yl]benzamide (C24) was converted to the product using the method described for the synthesis of 3-[(4aR,6S,8aS)-2-amino-6-methyl-4,4a,5,6-tetrahydropyrano[3,4-d][1,3]thiazin-8a (8H)-yl]-4-chlorobenzonitrile (6) in Example 6. Purification by reverse phase HPLC (Column: Waters Sunfire C18, 19×100 mm, 5 µm; Mobile phase A: 0.05% trifluoroacetic acid in water (v/v); Mobile phase B: 0.05% trifluoroacetic acid in acetonitrile (v/v); Gradient: 20.0% to 60% B, linear over 8.5 minutes). QC conditions: (Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute). Yield 22.5 mg, 0.08 mmol, 50%. LC/MS m/z 288.2 [M+H⁺]. Retention time: 1.62 minutes.

Example 8

(4aR,6R,8aS)-8a-(2,4-Difluoro-5-{[(2,2,2-trifluoro-ethyl)amino]methyl}phenyl)-6-(fluoromethyl)-4,4a,5,6,8,8a-hexahydropyrano[3,4-d][1,3]thiazin-2-amine (8)

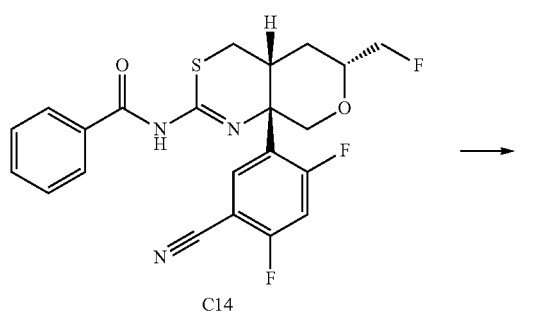

C14

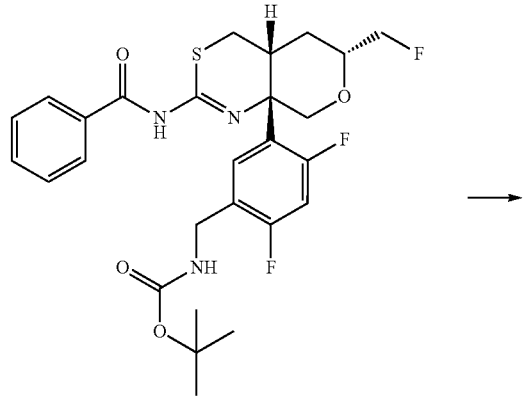

C25

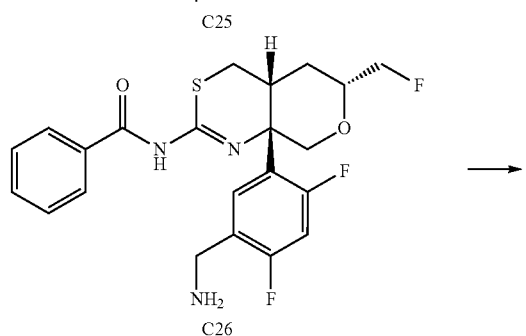

C26

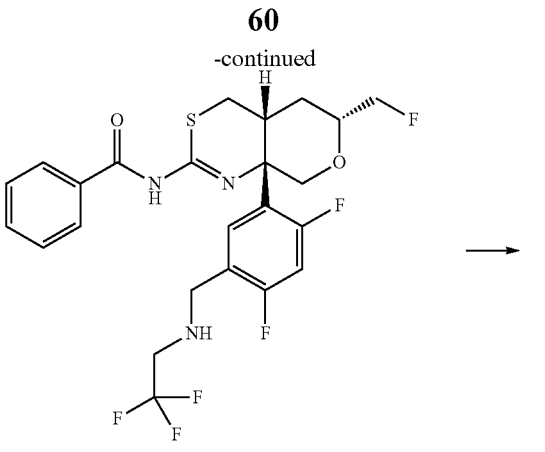

C27

8

Step 1. Synthesis of tert-butyl {5-[(4aR,6R,8aS)-2-(benzoylamino)-6-(fluoromethyl)-4,4a,5,6-tetrahydropyrano[3,4-d][1,3]thiazin-8a(8H)-yl]-2,4-difluorobenzyl}carbamate (C25)

To an ice-cooled (0° C.) heterogeneous mixture of N-[(4aR,6R,8aS)-8a-(5-cyano-2,4-difluorophenyl)-6-(fluoromethyl)-4,4a,5,6,8,8a-hexahydropyrano[3,4-d][1,3]thiazin-2-yl]benzamide (C14) (0.328 g, 0.736 mmol) in methanol (41 mL) was added di-tert-butyl dicarbonate (0.321 g, 1.47 mmol) and nickel (II) chloride hexahydrate (18 mg, 74 µmol) followed by the careful portion-wise addition of sodium borohydride (0.195 g, 5.15 mmol). The resulting black mixture was stirred at 0° C. for 20 minutes, then at room temperature for 16 hours. After that time, N-(2-aminoethyl)ethane-1,2-diamine (80 µL, 0.736 mmol) was added at room temperature and the reaction mixture was left stirring for 2 hours. The reaction mixture was partitioned between ethyl acetate (200 mL) and a saturated aqueous solution of ammonium chloride (500 mL). The aqueous layer was further extracted with ethyl acetate (2×100 mL). The combined organics were then washed sequentially with an aqueous saturated sodium bicarbonate solution (500 mL) and with brine (200 mL), dried over sodium sulfate, filtered and concentrated in vacuo to give the product as a black oily residue (0.59 g), which was taken directly to the following step. LCMS m/z 550 [M+H⁺].

Step 2. Synthesis of N-[(4aR,6R,8aS)-8a-[5-(aminomethyl)-2,4-difluorophenyl]-6-(fluoromethyl)-4,4a,5,6,8,8a-hexahydropyrano[3,4-d][1,3]thiazin-2-yl]benzamide (C26)

A solution of hydrogen chloride in dioxane (4.0 M, 10 mL, 41 mmol) was added to tert-butyl {5-[(4aR,6R,8aS)-2-(benzoylamino)-6-(fluoromethyl)-4,4a,5,6-tetrahydropyrano[3,4-d][1,3]thiazin-8a(8H)-yl]-2,4-difluorobenzyl}carbamate (C25) (0.8277 g, 1.506 mmol) at room temperature. The reaction mixture was stirred overnight and then concentrated under reduced pressure to yield a brown solid. The solid was partitioned between a 1:1 solution of ethyl acetate (100 mL) and saturated aqueous sodium bicarbonate (100 mL). The organics were separated and the aqueous layer was extracted further with ethyl acetate (2×100 mL). The combined organics were then washed with brine (200 mL), dried over sodium sulfate, filtered and concentrated under reduced pressure to yield the product as a brown solid (0.598 g), which was taken directly to the following step. LCMS m/z 450 [M+H$^+$]. $^1$H NMR (400 MHz, CD$_3$OD), characteristic peaks: δ 8.11-8.13 (m, 2H), 7.44-7.57 (m, 3H), 7.09 (dd, J=12.3, 9.6 Hz, 1H), 4.49-4.51 (m, 1H), 4.37-4.39 (m, 1H), 3.20-3.23 (m, 1H), 3.01 (dd, J=13.0, 4.2 Hz, 1H), 2.77 (dd, J=13.0, 2.8 Hz, 1H), 1.89 (m, 1H), 1.70 (ddd, J=13.4, 4.1, 2.2 Hz, 1H).

Step 3. Synthesis of N-[(4aR,6R,8aS)-8a-(2,4-difluoro-5-{[(2,2,2-trifluoroethyl)amino]methyl}phenyl)-6-(fluoromethyl)-4,4a,5,6,8,8a-hexahydropyrano[3,4-d][1,3]thiazin-2-yl]benzamide (C27)

A solution of N-[(4aR,6R,8aS)-8a-[5-(aminomethyl)-2,4-difluorophenyl]-6-(fluoromethyl)-4,4a,5,6,8,8a-hexahydropyrano[3,4-d][1,3]thiazin-2-yl]benzamide (C26) (0.598 g, 1.33 mmol) in acetonitrile (13 mL) was treated with triethylamine (0.277 mL, 2.00 mmol) and 2,2,2-trifluoroethyl trifluoromethanesulfonate (0.288 mL, 2.00 mmol). The reaction vial was sealed and the resulting solution was stirred at 70° C. for 16 hours. The reaction mixture was cooled to room temperature and concentrated under reduced pressure to yield a brown solid. The solid was partitioned between water (100 mL) and ethyl acetate (100 mL). The organics were isolated and the aqueous layer was extracted further with ethyl acetate (2×50 mL). The combined organics were then washed with brine (100 mL), dried over sodium sulfate, filtered and concentrated under reduced pressure. Purification via silica gel chromatography (Gradient: 0% to 60% ethyl acetate in heptane) afforded the product as a white solid. Yield: 0.4064 g, 57%. LCMS m/z 532.0 [M+H$^+$]. $^1$H NMR (400 MHz, CD$_3$OD) δ 8.12 (br d, J=8 Hz, 2H), 7.45-7.59 (m, 3H), 7.08 (dd, J=12.3, 9.6 Hz, 1H), 4.50-4.52 (m, 1H), 4.38-4.40 (m, 1H), 4.15 (dd, J=12.1, 2 Hz, 1H), 3.90-3.94 (m, 3H), 3.00 (dd, J=13.4, 4.0 Hz, 1H), 2.77 (dd, J=13.1, 2.9 Hz, 1H), 1.87-1.96 (m, 1H), 1.69-1.72 (m, 1H).

Step 4. Synthesis of (4aR,6R,8aS)-8a-(2,4-difluoro-5-{[(2,2,2-trifluoroethyl)amino]methyl}phenyl)-6-(fluoromethyl)-4,4a,5,6,8,8a-hexahydropyrano[3,4-d][1,3]thiazin-2-amine (8)

1,8-Diazabicyclo[5.4.0]undec-7-ene (0.084 mL, 0.534 mmol) was added to a solution of N-[(4aR,6R,8aS)-8a-(2,4-difluoro-5-{[(2,2,2-trifluoroethyl)amino]methyl}phenyl)-6-(fluoromethyl)-4,4a,5,6,8,8a-hexahydropyrano[3,4-d][1,3]thiazin-2-yl]benzamide (C27) (0.4064 g, 0.7650 mmol) in methanol (30 mL). The resulting solution was heated to 70° C. until complete consumption of starting material. The reaction mixture was concentrated under reduced pressure to yield product as an orange oily residue. Purification via silica gel chromatography (Gradient: 0% to 20% methanol in dichloromethane) afforded the product as a white solid. Yield: 0.273 g (84%). LCMS m/z 428 [M+H$^+$]. $^1$H NMR (400 MHz, CD$_3$OD) δ 7.38 (t, J=8.8 Hz, 1H), 6.98 (dd, J=12.2, 9.7 Hz, 1H), 4.42-4.48 (m, 1H), 4.30-4.37 (m, 1H), 4.09 (dd, J=11.2, 2.0 Hz, 1H), 3.86-3.90 (m, 3H), 3.72 (d, J=11.2 Hz, 1H), 3.13-3.18 (m, 2H), 2.90-2.97 (m, 2H), 2.70 (dd, J=12.4, 2.6 Hz, 1H), 1.76-1.87 (m, 1H), 1.52 (ddd, J=13.1, 4.0, 2.3 Hz, 1H).

Example 9

(4aR,6S,8aS)-8a-(2,4-Difluoro-5-{[(2,2,2-trifluoroethyl)amino]methyl}phenyl)-6-methyl-4,4a,5,6,8,8a-hexahydropyrano[3,4-d][1,3]thiazin-2-amine (9)

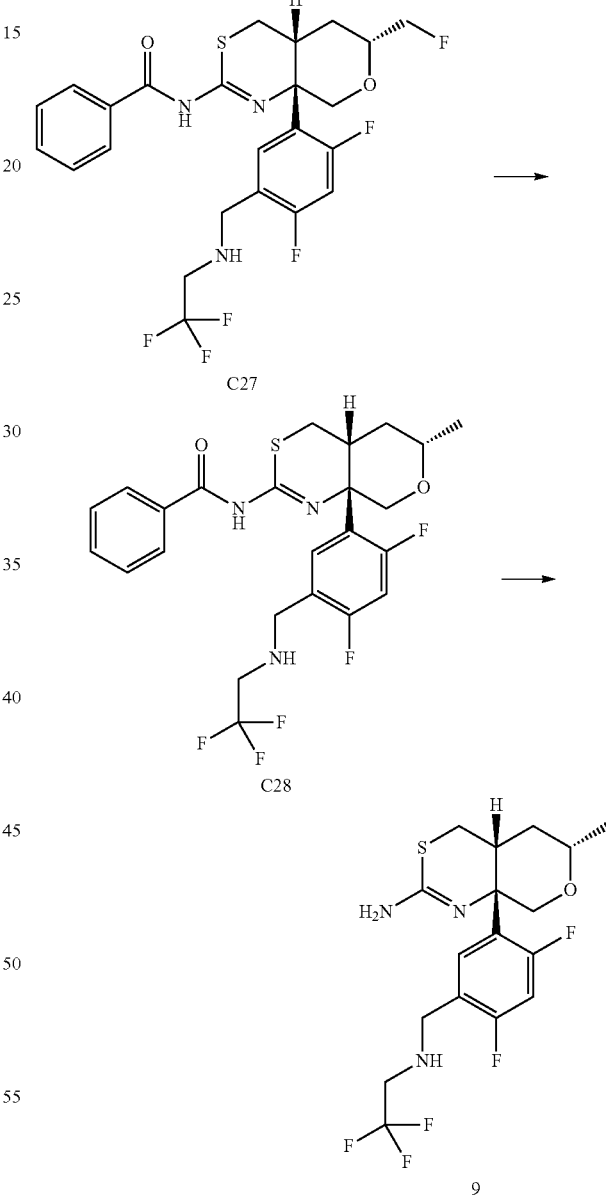

Step 1. Synthesis of N-[(4aR,6S,8aS)-8a-(2,4-difluoro-5-{[(2,2,2-trifluoroethyl)amino]methyl}phenyl)-6-methyl-4,4a,5,6,8,8a-hexahydropyrano[3,4-d][1,3]thiazin-2-yl]benzamide (C28)

Lithium triethylborohydride (1.13 mL, 1.13 mmol) was added to a solution of N-[(4aR,6R,8aS)-8a-(2,4-difluoro-5-

{[(2,2,2-trifluoroethyl)amino]methyl}phenyl)-6-(fluoromethyl)-4,4a,5,6,8,8a-hexahydropyrano[3,4-d][1,3]thiazin-2-yl]benzamide (C27) (60 mg, 0.11 mmol) in tetrahydrofuran (4 mL). The reaction mixture was allowed to stir at room temperature for 16 hours and then partitioned between ethyl acetate (25 mL) and a saturated aqueous solution of sodium bicarbonate (50 mL). The layers were separated and the aqueous layer was extracted further with ethyl acetate (3×25 mL). The combined organics were then washed sequentially with water (100 mL) and with brine (100 mL), dried over sodium sulfate and filtered. The filtrate was concentrated under reduced pressure to yield a white solid. The organic crude was re-dissolved in dichloromethane (20 mL) and the resulting solution was washed with 1 N sodium hydroxide (3×25 mL), water (100 mL), and brine (100 mL). The organic layer was dried over sodium sulfate, filtered and concentrated under reduced pressure to provide the product as an orange solid (60 mg), which was taken directly to the following step. LCMS m/z 514 [M+H$^+$].

Step 2. Synthesis of (4aR,6S,8aS)-8a-(2,4-difluoro-5-{[(2,2,2-trifluoroethyl)amino]methyl}phenyl)-6-methyl-4,4a,5,6,8,8a-hexahydropyrano[3,4-d][1,3]thiazin-2-amine (9)

N-[(4aR,6S,8aS)-8a-(2,4-Difluoro-5-{[(2,2,2-trifluoroethyl)amino]methyl}phenyl)-6-methyl-4,4a,5,6,8,8a-hexahydropyrano[3,4-d][1,3]thiazin-2-yl]benzamide (C28) was converted to the product according to the method described for the synthesis of (4aR,6R,8aS)-8a-(2,4-difluoro-5-{[(2,2,2-trifluoroethyl)amino]methyl}phenyl)-6-(fluoromethyl)-4,4a,5,6,8,8a-hexahydropyrano[3,4-d][1,3]thiazin-2-amine (8) in Example 8. Purification via silica gel chromatography (Gradient: 0% to 20% methanol in dichloromethane) afforded the product as a white solid. Yield: 12 mg, 25%. LCMS m/z 410 [M+H$^+$]. $^1$H NMR (400 MHz, CD$_3$OD) δ 7.39 (t, J=8.7 Hz, 1H), 7.00 (dd, J=12.3, 9.6 Hz, 1H), 4.07 (dd, J=11.3, 2.0 Hz, 1H), 3.70-3.79 (m, 2H), 3.18 (q, J=9.3 Hz, 2H), 2.91-3.02 (m, 2H), 2.73 (dd, J=12.5, 2.7 Hz, 1H), 1.58-1.73 (m, 2H), 1.24 (d, J=8.0 Hz, 3H).

Example 10

3-[(4aR,6R,8aS)-2-Amino-6-(3-methyl-1,2-oxazol-5-yl)-4,4a,5,6-tetrahydropyrano[3,4-d][1,3]thiazin-8a(8H)-yl]-4-fluorobenzonitrile (10)

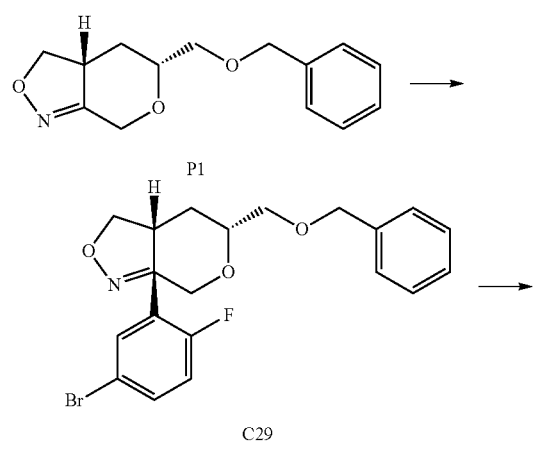

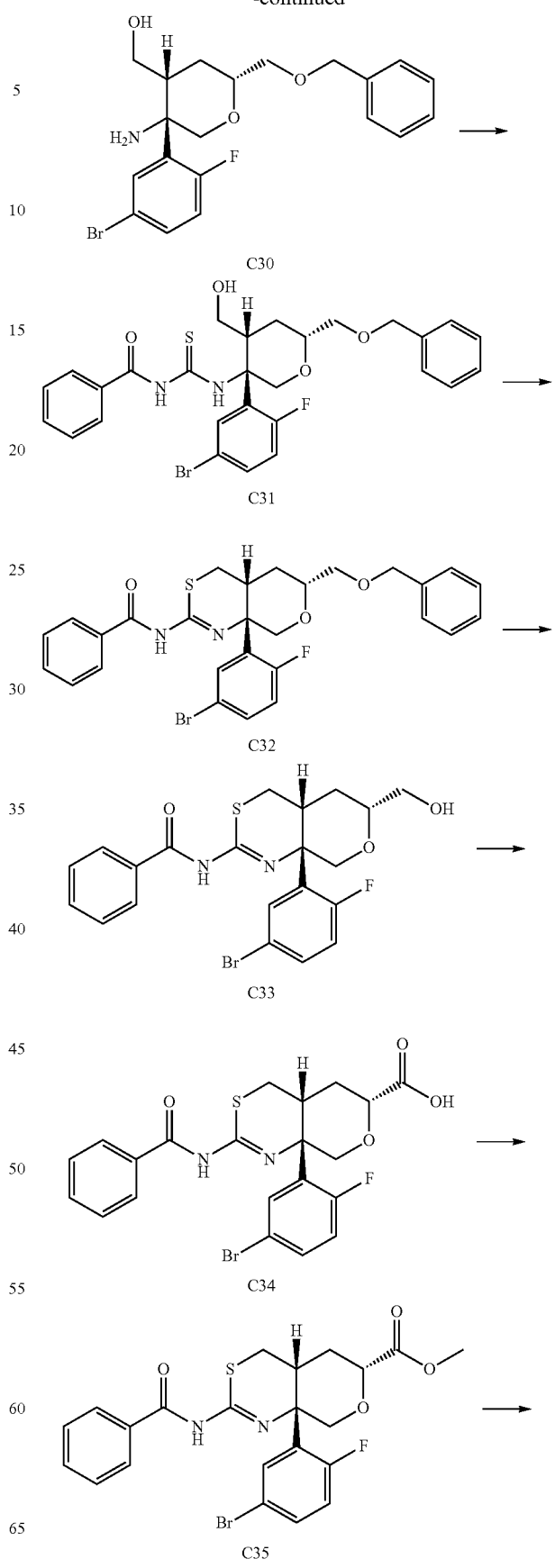

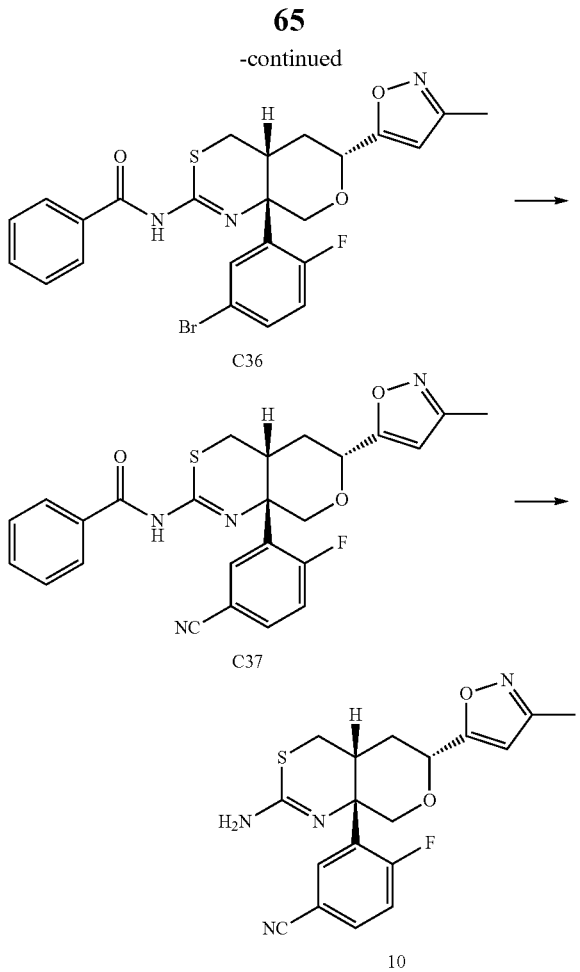

Step 1. Synthesis of (3aR,5R,7aS)-5-[(benzyloxy)methyl]-7a-(5-bromo-2-fluorophenyl)hexahydro-1H-pyrano[3,4-c][1,2]oxazole (C29)

A solution of (3aR,5R)-5-[(benzyloxy)methyl]-3,3a,4,5-tetrahydro-7H-pyrano[3,4-c][1,2]oxazole (P1) (10.0 g, 40.4 mmol) in toluene (404 mL) was cooled down to −78° C. and then boron trifluoride-diethyl etherate (46.5%, 10.8 mL, 40.8 mmol) was added. The resulting solution was allowed to stir at the same temperature for 30 minutes, with fast stirring. After that time, 4-bromo-1-fluoro-2-iodobenzene (12.3 g, 40.8 mmol) was added to the reaction mixture, followed by the slow addition (temperature never varied more than 5° C.) of n-butyllithium (2.5 M in hexanes; 16.3 mL, 42.7 mmol). The resulting solution was allowed to stir at −78° C. for 90 minutes. At this time, a saturated aqueous solution of ammonium chloride (20 mL) was added to the reaction mixture at −78° C. The reaction mixture was warmed to room temperature and partitioned between ethyl acetate (400 mL) and water (800 mL). The organics were separated and the aqueous layer was extracted with additional ethyl acetate (3×200 mL). The combined organics were then washed with brine (200 mL), dried over sodium sulfate, filtered and concentrated under reduced pressure to yield a clear oily residue. Purification via silica gel chromatography (Gradient: 10% to 70% ethyl acetate in heptane) afforded the product as an orange solid. Yield: 11.5 g, 27.1 mmol, 67%. $^1$H NMR (400 MHz, CD$_3$OD) δ 8.01 (dd, J=6.9, 2.6 Hz, 1H), 7.47 (ddd, J=8.8, 4.4, 2.7 Hz, 1H), 7.38-7.28 (m, 4H), 7.07 (dd, J=11.6, 8.7 Hz, 1H), 4.58 (s, 2H), 4.10 (dd, J=11.6, 2.4 Hz, 1H), 3.82-3.78 (m, 2H), 3.72 (d, J=7.2 Hz, 1H), 3.61-3.55 (m, 2H), 3.52 (dd, J=8.8, 4.7 Hz, 1H), 3.16-3.10 (m, 1H), 1.86 (ddd, J=14.1, 7.0, 2.2 Hz, 1H), 1.59 (dtd, J=13.7, 11.8, 1.7 Hz, 1H).

Step 2. Synthesis of [(2R,4R,5S)-5-amino-2-[(benzyloxy)methyl]-5-(5-bromo-2-fluorophenyl)tetrahydro-2H-pyran-4-yl]methanol (C30)

Molybdenum hexacarbonyl (0.702 g, 2.60 mmol) was added to a solution of (3aR,5R)-5-[(benzyloxy)methyl]-3,3a,4,5-tetrahydro-7H-pyrano[3,4-c][1,2]oxazole C29 (1.00 g, 2.37 mL) in acetonitrile (10 mL) and water (0.7 mL). The resulting solution was refluxed for 30 minutes and then cooled down to room temperature. Once at room temperature, sodium borohydride (0.089 g, 2.37 mmol) was added to the reaction mixture. The resulting solution was then heated to reflux for another 3 hours. The reaction mixture was cooled down to room temperature, quenched with methanol (100 mL), filtered through Celite and the resulting Celite pad was washed with ethyl acetate (3×200 mL). The combined filtrate was washed sequentially with a saturated aqueous solution of sodium bicarbonate (2×250 mL) and with brine (200 mL) and dried over sodium sulfate. The resulting solution was filtered and concentrated under reduced pressure to give the product as a black oily residue, which was taken directly to the following step. LCMS m/z 425.2 [M+H$^+$].

Step 3. Synthesis of N-{[(3S,4R,6R)-6-[(benzyloxy)methyl]-3-(5-bromo-2-fluorophenyl)-4-(hydroxymethyl)tetrahydro-2H-pyran-3-yl]carbamothioyl}benzamide (C31)

Benzoyl isothiocyanate (3.40 mL, 25.3 mmol) was added to a solution of [(2R,4R,5S)-5-amino-2-[(benzyloxy)methyl]-5-(5-bromo-2-fluorophenyl)tetrahydro-2H-pyran-4-yl]methanol (C30) (10.84 g, 25.55 mmol) in dichloromethane (255 mL). The reaction mixture was stirred at room temperature for 48 hours and then concentrated under reduced pressure to afford the product as a light yellow solid (9.49 g), which was taken directly to the following step. LCMS m/z 587.0 [M−H$^+$].

Step 4. Synthesis of N-[(4aR,6R,8aS)-6-[(benzyloxy)methyl]-8a-(5-bromo-2-fluorophenyl)-4,4a,5,6,8,8a-hexahydropyrano[3,4-d][1,3]thiazin-2-yl]benzamide (C32)

A solution of N-{[(3S,4R,6R)-6-[(benzyloxy)methyl]-3-(5-bromo-2-fluorophenyl)-4-(hydroxymethyl)tetrahydro-2H-pyran-3-yl]carbamothioyl}benzamide (C31) (9.49 g, 16.2 mmol) and pyridine (4.94 mL, 61.4 mmol) in dichloromethane (278 mL) was cooled to −50° C. Trifluoromethanesulfonic anhydride (5.44 mL, 32.3 mmol) was added drop-wise to the solution and the mixture was gradually warmed to 0° C. After 2 hours, the reaction mixture was partitioned between dichloromethane (1 L) and water (500 mL). The organic layer was washed with dichloromethane (2×250 mL) and the combined organics were then washed with brine (500 mL). The resulting organic layer was dried over magnesium sulfate, filtered and concentrated in vacuo to yield an orange oily residue. Purification via silica gel chromatography (Gradient: 0% to 60% ethyl acetate in heptane) afforded the product as an orange solid. Yield: 5.53 g, 60%. LCMS m/z 571.2 [M+H$^+$]. $^1$H NMR (400 MHz, CD$_3$OD) characteristic peaks: δ 8.12 (d, J=7.4 Hz, 2H), 7.43-5.58 (m, 5H), 7.12-7.32 (m, 6H), 4.51-4.60 (m, 2H), 4.10-4.13 (m, 1H), 3.87-3.91 (m, 1H), 3.55-3.63 (m, 2H), 3.18-3.21 (m, 1H), 2.94 (dd, J=13.2, 4.0 Hz, 1H), 2.74 (dd, J=13.1, 2.9 Hz, 1H), 1.90-1.99 (m, 1H), 1.67-1.72 (m, 1H).

Step 5. Synthesis of N-[(4aR,6R,8aS)-8a-(5-bromo-2-fluorophenyl)-6-(hydroxymethyl)-4,4a,5,6,8,8a-hexahydropyrano[3,4-d][1,3]thiazin-2-yl]benzamide (C33)

Boron trichloride (45.8 mL, 45.8 mmol) was added to a solution of N-[(4aR,6R,8aS)-6-[(benzyloxy)methyl]-8a-(5-bromo-2-fluorophenyl)-4,4a,5,6,8,8a-hexahydropyrano[3,4-d][1,3]thiazin-2-yl]benzamide (C32) (8.70 g, 15.3 mmol) in dichloromethane (76 mL) at 0° C., while maintaining the internal temperature below 5° C. The heterogeneous mixture was allowed to stir for 10 minutes at 0° C. and then at room temperature for 16 hours. The reaction mixture was then quenched by drop-wise addition of methanol (100 mL). The methanol solution was refluxed for 15 minutes and then concentrated under reduced pressure. The residue was re-dissolved in dichloromethane (100 mL) and washed sequentially with 1 N sodium hydroxide (2×100 mL) and with brine (100 mL), dried over sodium sulfate and filtered. Purification via silica gel chromatography (Gradient: 30% to 100% ethyl acetate in heptane) afforded the product as an off-white solid. Yield: 4.98 g, 68%. LCMS m/z 410 [M+H$^+$]. $^1$H NMR (400 MHz, CD$_3$OD) δ 8.13 (d, J=6.8 Hz, 1H), 7.59-7.45 (m, 4H), 7.16 (dd, J=12.1, 8.6 Hz, 1H), 4.15-4.11 (m, 1H), 3.91 (d, J=11.9 Hz, 1H), 3.79-3.73 (m, 1H), 3.59 (d, J=5.1 Hz, 1H), 3.21 (br s, 1H), 2.96 (dd, J=13.0, 4.0 Hz, 1H), 2.76 (dd, J=13.2, 2.8 Hz, 1H), 1.81-1.90 (m, 1H), 1.72-1.68 (m, 1H).

Step 6. Synthesis of (4aR,6R,8aS)-2-(benzoylamino)-8a-(5-bromo-2-fluorophenyl)-4,4a,5,6,8,8a-hexahydropyrano[3,4-d][1,3]thiazine-6-carboxylic acid (C34)

N-Methylmorpholine N-oxide monohydrate (3.38 g, 25.0 mmol) and tetrapropylammonium perruthenate (0.147 g, 0.417 mmol) were added to a solution of N-[(4aR,6R,8aS)-8a-(5-bromo-2-fluorophenyl)-6-(hydroxymethyl)-4,4a,5,6,8,8a-hexahydropyrano[3,4-d][1,3]thiazin-2-yl]benzamide (C33) (2.0 g, 4.17 mmol) in acetonitrile (75 mL). The reaction mixture was allowed to stir at room temperature for 16 hours. 2-Propanol (200 mL) was added to the reaction mixture and the resulting solution was left stirring at room temperature for 35 minutes. After that time, the reaction mixture was concentrated under reduced pressure. The oily residue was partitioned between aqueous 0.25 M sodium hydroxide (200 mL) and a 1:1 solution of diethyl ether:ethyl acetate (200 mL each). The layers were isolated and the organic layer was washed with aqueous 0.25 M sodium hydroxide (3×200 mL). The combined aqueous layers were then acidified to pH 1 with 2 M aqueous hydrochloric acid (300 mL). The now heterogeneous mixture was extracted with ethyl acetate (4×200 mL). The combined organics were then dried over sodium sulfate, filtered and concentrated under reduced pressure to give the product (2.34 g) as a purple solid, which was taken directly to the following step. LCMS m/z 495.1 [M+H$^+$].

$^1$H NMR (400 MHz, CD$_3$OD) δ 8.08-8.11 (m, 1H), 7.50-7.64 (m, 4H), 7.17-7.22 (m, 1H), 4.39 (dd, J=11.8, 2.8 Hz, 1H), 4.20 (d, J=12.1 Hz, 1H), 4.04-4.07 (m, 1H), 3.06 (dd, J=12.9, 4.3 Hz, 1H), 2.92 (dd, J=13.7, 3.1 Hz, 1H), 2.13-2.18 (m, 1H), 2.05-2.09 (m, 1H), 1.99-2.02 (m, 4H).

Step 7. Synthesis of (4aR,6R,8aS)-2-(benzoylamino)-8a-(5-bromo-2-fluorophenyl)-4,4a,5,6,8,8a-hexahydropyrano[3,4-d][1,3]thiazine-6-carboxylate (C35)

To a solution of (4aR,6R,8aS)-2-(benzoylamino)-8a-(5-bromo-2-fluorophenyl)-4,4a,5,6,8,8a-hexahydropyrano[3,4-d][1,3]thiazine-6-carboxylic acid (C34) (1.00 g, 2.03 mmol) in dichloromethane (15 mL) was added oxalyl chloride (0.536 mL, 6.24 mmol) in a drop-wise manner, followed by slow addition of N,N-dimethylformamide (0.025 mL, 0.32 mmol). The resulting solution was stirred at room temperature for 15 minutes. The reaction mixture was quenched with methanol (20 mL) and concentrated under reduced pressure. Purification via silica gel chromatography (Gradient: 30% to 100% ethyl acetate in heptane) afforded the product as a yellow solid. Yield: 1.09 g (quantitative). LCMS m/z 507.1 [M+H$^+$].

$^1$H NMR (400 MHz, CD$_3$OD) δ 8.04-8.07 (m, 1H), 7.58-7.76 (m, 4H), 7.24 (dd, J=12.3, 8.6 Hz, 1H), 4.49 (dd, J=11.7, 2.7 Hz, 1H), 4.22 (s, 1H), 4.03-4.12 (m, 1H), 3.53 (dd, J=12.0, 4.2 Hz, 1H), 3.21 (td, J=13.6, 3.3 Hz, 2H), 2.21 (ddd, J=14.0, 4.6, 2.5 Hz, 1H).

Step 8. Synthesis of N-[(4aR,6R,8aS)-8a-(5-bromo-2-fluorophenyl)-6-(3-methyl-1,2-oxazol-5-yl)-4,4a,5,6,8,8a-hexahydropyrano[3,4-d][1,3]thiazin-2-yl]benzamide (C36)

A solution of propan-2-one oxime (0.216 g, 2.96 mmol) in tetrahydrofuran (10 mL) was cooled to 0° C. To this solution was added n-butyllithium (2.5 M in hexanes, 2.40 mL, 6.00 mmol) in a drop-wise manner. The resulting solution was allowed to warm to room temperature and left stirring at room temperature for 25 minutes. The resulting solution was cooled again to 0° C., followed by a drop-wise addition of methyl (4aR,6R,8aS)-2-(benzoylamino)-8a-(5-bromo-2-fluorophenyl)-4,4a,5,6,8,8a-hexahydropyrano[3,4-d][1,3]thiazine-6-carboxylate (C35) (1.09 g, 2.03 mmol) in tetrahydrofuran (3 mL). The reaction mixture was allowed to warm to room temperature and was left stirring for 25 minutes. The reaction mixture was cooled to 0° C. again, and sulfuric acid (0.840 mL, 15.8 mmol) was added in a drop-wise manner. The reaction mixture was allowed to warm up to room temperature and was left stirring for 16 hours at room temperature. The reaction mixture was basified to pH 12 with sodium hydroxide (5 N, ~4 mL) and then extracted with ethyl acetate (3×100 mL). The combined organics were dried over sodium sulfate, filtered and concentrated under reduced pressure to give an oily residue. Purification via silica gel chromatography (Gradient: 0% to 100% ethyl acetate in heptane) afforded the product as a white solid. Yield: 330 mg, 63%. LCMS m/z 532.2 [M+H$^+$]. $^1$H NMR (400 MHz, CD$_3$OD) δ 8.12 (br s, 1H), 7.47-7.61 (m, 4H), 7.19 (dd, J=12.0, 8.9 Hz, 1H), 4.97 (br d, J=9.4 Hz, 1H), 4.31 (dd, J=11.8, 1.5 Hz, 1H), 4.00-4.14 (m, 2H), 3.00 (dd, J=13.2, 4.0 Hz, 1H), 2.83 (dd, J=13.1, 2.9 Hz, 1H), 2.10 (d, J=12.1 Hz, 1H).

Step 9. Synthesis of N-[(4aR,6R,8aS)-8a-(5-cyano-2-fluorophenyl)-6-(3-methyl-1,2-oxazol-5-yl)-4,4a,5,6,8,8a-hexahydropyrano[3,4-d][1,3]thiazin-2-yl]benzamide (C37)

N-[(4aR,6R,8aS)-8a-(5-Bromo-2-fluorophenyl)-6-(3-methyl-1,2-oxazol-5-yl)-4,4a,5,6,8,8a-hexahydropyrano[3,4-d][1,3]thiazin-2-yl]benzamide (C36) (0.100 g, 0.189 mmol), zinc cyanide (0.027 g, 0.227 mmol), tetrakis(triphenylphosphine)palladium(0) (0.127 g, 0.110 mmol) and N,N-dimethylformamide (6 mL) were added to an Emrys microwave reaction vial. The vial was sealed and purged with nitrogen gas for 10 minutes with stirring. After that time, the vial was placed on a Biotage microwave processor and heated to 80° C. for 3 hours. The reaction mixture was partitioned between ethyl acetate (100 mL) and a saturated aqueous solution of sodium bicarbonate (100 mL). The layers were separated and aqueous layer was extracted further with ethyl acetate (3×50 mL). The combined organics were washed with brine (200 mL), dried over sodium sulfate, filtered and concentrated in vacuo. Purification via silica gel chromatography (Gradient: 30% to 100% ethyl acetate in heptane) afforded the product as an off-white solid. Yield: 51 mg, 57%. LCMS m/z 477.3 [M+H$^+$]. $^1$H NMR (400 MHz, CD$_3$OD) characteristic peaks: δ 8.09 (br s, 2H), 7.83-7.87 (m, 2H), 7.40-7.59 (m, 4H), 4.97 (d, J=9.2 Hz, 1H), 4.30 (dd, J=11.7, 1.6 Hz, 1H), 4.00-4.13 (m, 2H), 2.97 (dd, J=12.9, 3.9 Hz, 1H), 2.82 (dd, J=13.2, 3.0 Hz, 1H).

Step 10. Synthesis of 3-[(4aR,6R,8aS)-2-amino-6-(3-methyl-1,2-oxazol-5-yl)-4,4a,5,6-tetrahydropyrano[3,4-d][1,3]thiazin-8a(8H)-yl]-4-fluorobenzonitrile (10)

Methylamine (8 M in ethanol, 1.34 mmol) was added to a solution of N-[(4aR,6R,8aS)-8a-(5-cyano-2-fluorophenyl)-6-(3-methyl-1,2-oxazol-5-yl)-4,4a,5,6,8,8a-hexahydropyrano[3,4-d][1,3]thiazin-2-yl]benzamide (C37) (0.051 g, 0.11 mmol) in ethanol (4 mL). The resulting solution was allowed to stir at room temperature for 16 hours. The reaction mixture was concentrated under reduced pressure to give a yellow oily residue. Purification via silica gel chromatography (Gradient: 0% to 15% methanol in dichloromethane) afforded the product as an off-white solid. Yield: 25 mg, 63%. LCMS m/z 373.1 [M+H$^+$]. $^1$H NMR (400 MHz, CD$_3$OH) δ 7.78 (ddd, J=8.5, 4.5, 2.2 Hz, 1H), 7.69 (dd, J=7.2, 2.2 Hz, 1H), 7.35 (dd, J=8.6, 11.3 Hz, 1H), 6.26 (s, 1H), 4.89 (dd, J=11.9, 2.5 Hz, 1H), 4.25 (dd, J=11.2, 2.2 Hz, 1H), 3.80 (d, J=11.2 Hz, 1H), 3.08-3.14 (m, 1H), 2.89 (dd, J=12.7, 4.1 Hz, 1H), 2.78 (dd, J=12.7, 2.9 Hz, 1H), 2.28 (s, 3H), 2.10-2.22 (m, 1H), 1.91-1.96 (m, 1H).

Example 11

3-[(4aR,6R,8aS)-2-Amino-6-(4-methyl-1,3-oxazol-2-yl)-4,4a,5,6-tetrahydropyrano[3,4-d][1,3]thiazin-8a(8H)-yl]-4-fluorobenzonitrile (11)

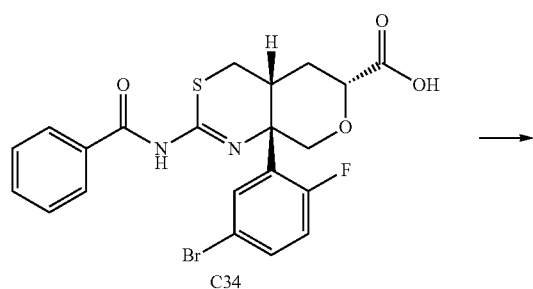

C34

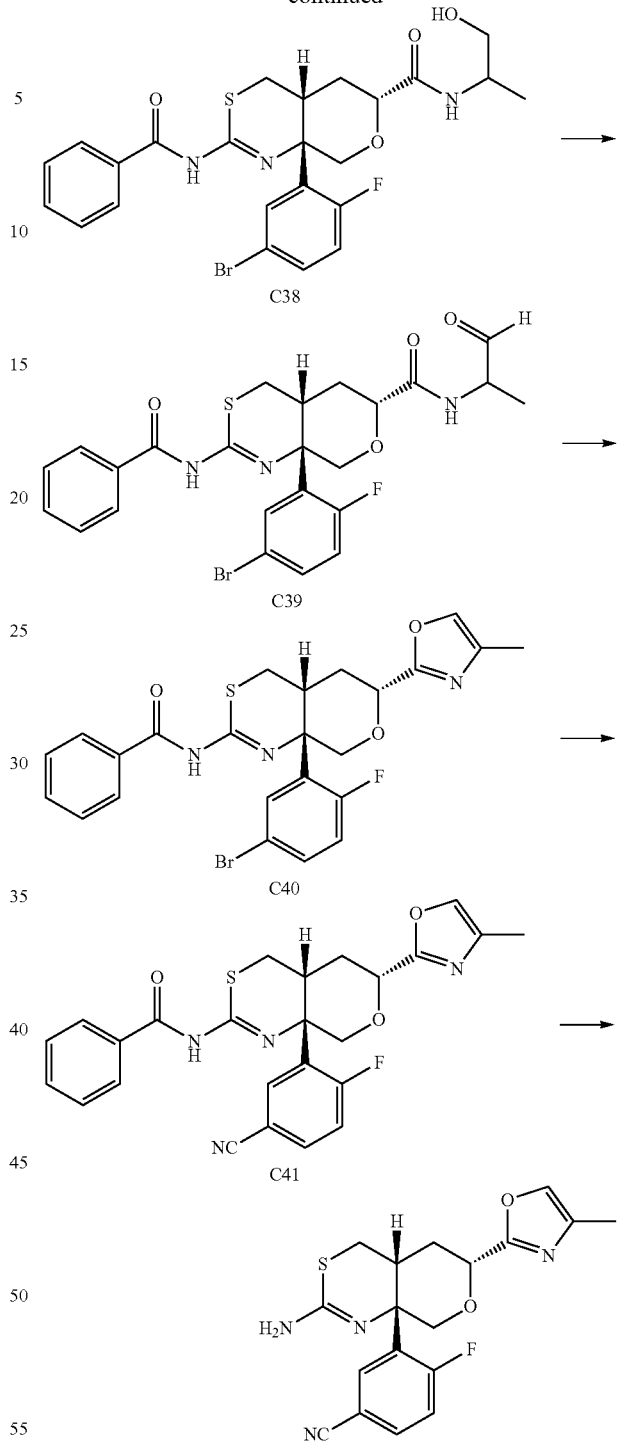

Step 1. Synthesis of (4aR,6R,8aS)-2-(benzoylamino)-8a-(5-bromo-2-fluorophenyl)-N-(1-hydroxypropan-2-yl)-4,4a,5,6,8,8a-hexahydropyrano[3,4-d][1,3]thiazine-6-carboxamide (C38)

Diisopropylethylamine (0.706 mL, 4.05 mmol) and O-(2-oxo-1(2H)pyridyl)-N,N,N',N'-tetramethyluronium tetrafluoroborate (0.662 g, 2.23 mmol) were added to a solution of (4aR,6R,8aS)-2-(benzoylamino)-8a-(5-bromo-2-fluorophenyl)-4,4a,5,6,8,8a-hexahydropyrano[3,4-d][1,3]thiazine-6-carboxylic acid (C34) (1.00 g, 2.03 mmol) in N,N-dimethylformamide (22 mL). The resulting solution was allowed to stir at room temperature for 30 minutes. Additional diisopropylethylamine (0.7 mL, 4.05 mmol) and O-(2-oxo-1(2H)pyridyl)-N,N,N',N'-tetramethyluronium tetrafluoroborate (0.6 g, 2 mmol) were added to the reaction mixture and the resulting solution was allowed to stir at room temperature for an additional 60 minutes. Then 2-amino-1-propanol (0.632 mL, 8.11 mmol) was added in one portion. The resulting black solution was allowed to stir at room temperature for 16 hours. The reaction mixture was partitioned between an aqueous saturated solution of sodium bicarbonate (100 mL), water (100 mL) and diethyl ether (100 mL). The organic layer was isolated and the aqueous layer was further extracted with diethyl ether (3×100 mL). The combined organics were then washed with water (100 mL), brine (100 mL), dried over sodium sulfate and concentrated to give the product (897 mg, 80%), which was used directly in the following step. LCMS m/z 552.2 [M+H$^+$]. $^1$H NMR (400 MHz, CD$_3$OH) characteristic peaks δ 8.11 (br s, 2H), 7.46-7.59 (m, 4H), 7.17 (dd, J=12.0, 9.1 Hz, 1H), 4.20 (d, J=11.9 Hz, 1H), 3.96-4.12 (m, 2H).

Step 2. Synthesis of (4aR,6R,8aS)-2-(benzoylamino)-8a-(5-bromo-2-fluorophenyl)-N-(1-oxopropan-2-yl)-4,4a,5,6,8,8a-hexahydropyrano[3,4-d][1,3]thiazine-6-carboxamide (C39)

Dess-Martin periodinane (1.04 g, 2.44 mmol) was added to a solution of (4aR,6R,8aS)-2-(benzoylamino)-8a-(5-bromo-2-fluorophenyl)-N-(1-hydroxypropan-2-yl)-4,4a,5,6,8,8a-hexahydropyrano[3,4-d][1,3]thiazine-6-carboxamide (C38) (0.897 g, 1.63 mmol) in dichloromethane (75 mL). The resulting solution was left stirring overnight at room temperature. The reaction mixture was diluted with diethyl ether (100 mL), a saturated aqueous solution of sodium bicarbonate (50 mL) and a 10% aqueous solution of sodium thiosulfate (50 mL). The layers were separated and the resulting aqueous layer was further extracted with diethyl ether (2×100 mL). The combined organics were then washed with water (100 mL), brine (100 mL), dried over sodium sulfate, filtered and concentrated under reduced pressure to give the product as a white solid. Yield 747 mg, 84%. LCMS m/z 532.1 [M+H$^+$]. $^1$H NMR (400 MHz, CD$_3$OD) characteristic peaks: δ 9.47 (d, J=6.7 Hz, 1H), 8.11 (br d, J=6.7 Hz, 2H), 7.46-7.60 (m, 4H), 7.18 (dd, J=12.1, 9.2 Hz, 1H), 4.19-4.31 (m, 2H), 4.01-4.13 (m, 1H).

Step 3. Synthesis of N-[(4aR,6R,8aS)-8a-(5-bromo-2-fluorophenyl)-6-(4-methyl-1,3-oxazol-2-yl)-4,4a,5,6,8,8a-hexahydropyrano[3,4-d][1,3]thiazin-2-yl]benzamide (C40)

Methyl N-(triethylammoniumsulfonyl)carbamate (Burgess reagent) (0.811 g, 3.40 mmol) was added to a solution of (4aR,6R,8aS)-2-(benzoylamino)-8a-(5-bromo-2-fluorophenyl)-N-(1-oxopropan-2-yl)-4,4a,5,6,8,8a-hexahydropyrano[3,4-d][1,3]thiazine-6-carboxamide (C39) (0.747 g, 1.36 mmol) in toluene (34 mL). The resulting solution was stirred at room temperature for 10 minutes, followed by heating to 65° C. for 16 hours. The reaction mixture was concentrated under reduced pressure. Purification via silica gel chromatography (Gradient: 0% to 100% ethyl acetate in heptane) afforded the product as a yellow oily residue. Yield: 417 mg, 58%. LCMS m/z 532.1 [M+H$^+$]. $^1$H NMR (400 MHz, CDCl$_3$) δ 8.17 (br s, 2H), 7.36-7.54 (m, 5H), 7.36 (q, J=1.2 Hz, 1H), 7.01-7.06 (m, 1H), 4.83 (dd, J=12.0, 2.4 Hz, 1H), 4.31 (dd, J=11.9, 1.6 Hz, 1H), 3.07 (dd, J=13.0, 3.8 Hz, 1H), 2.70 (m, 1H), 2.58-2.54 (m, 1H), 2.17 (d, J=1.7 Hz, 3H), 2.08-2.14 (m, 1H).

Step 4. Synthesis of N-[(4aR,6R,8aS)-8a-(5-cyano-2-fluorophenyl)-6-(4-methyl-1,3-oxazol-2-yl)-4,4a,5,6,8,8a-hexahydropyrano[3,4-d][1,3]thiazin-2-yl]benzamide (C41)

N-[(4aR,6R,8aS)-8a-(5-Bromo-2-fluorophenyl)-6-(4-methyl-1,3-oxazol-2-yl)-4,4a,5,6,8,8a-hexahydropyrano[3,4-d][1,3]thiazin-2-yl]benzamide (C40) was converted to the product using the method described for synthesis of N-[(4aR,6R,8aS)-8a-(5-cyano-2-fluorophenyl)-6-(3-methyl-1,2-oxazol-5-yl)-4,4a,5,6,8,8a-hexahydropyrano[3,4-d][1,3]thiazin-2-yl]benzamide (C37) in Example 10. The product was obtained as a white solid. Yield: 227 mg, 126%. LCMS m/z 477.2 [M+H$^+$]. $^1$H NMR (400 MHz, CD$_3$OH) δ 8.09 (br s, 2H), 7.83-7.86 (m, 2H), 7.61 (q, J=2.3 Hz, 1H), 7.55-7.65 (m, 2H), 7.40-7.51 (m, 3H), 4.91 (dd, J=11.8, 2.4 Hz, 1H), 4.35 (dd, J=11.9, 1.6 Hz, 1H), 4.00-4.13 (m, 2H), 2.97 (dd, J=13.1, 3.7 Hz, 1H), 2.82 (dd, J=13.2, 2.8 Hz, 1H), 2.38-2.47 (m, 1H), 2.15 and 2.01 (d, J=3.8 Hz, 3H), 2.03-2.07 (m, 1H).

Step 5. Synthesis of 3-[(4aR,6R,8aS)-2-amino-6-(4-methyl-1,3-oxazol-2-yl)-4,4a,5,6-tetrahydropyrano[3,4-d][1,3]thiazin-8a(8H)-yl]-4-fluorobenzonitrile (11)

Methylamine (8 M in ethanol, 7.1 mL, 57.1 mmol) was added to a solution of N-[(4aR,6R,8aS)-8a-(5-cyano-2-fluorophenyl)-6-(4-methyl-1,3-oxazol-2-yl)-4,4a,5,6,8,8a-hexahydropyrano[3,4-d][1,3]thiazin-2-yl]benzamide (C41) (0.227 g, 0.48 mmol) in ethanol (12 mL). The resulting solution was allowed to stir at room temperature for 16 hours. The reaction mixture was concentrated under reduced pressure to give a yellow oily residue. Purification via silica gel chromatography (Gradient: 0% to 20% methanol in dichloromethane) afforded the product as an off-white solid. Yield: 144 mg, 81%. LCMS m/z 374.1 [M+H$^+$]. $^1$H NMR (400 MHz, CD$_3$OH) δ 7.77 (ddd, J=8.5, 4.5, 2.2 Hz, 1H), 7.68 (dd, J=7.2, 2.3 Hz, 1H), 7.61 (q, J=2.3 Hz, 1H), 7.35 (dd, J=12.1, 8.6 Hz, 1H), 4.82 (dd, J=11.9, 2.5 Hz, 1H), 4.25 (dd, J=11.2, 2.2 Hz, 1H), 3.79 (d, J=11.2 Hz, 1H), 3.06-3.13 (m, 1H), 2.89 (dd, J=12.7, 4.1 Hz, 1H), 2.78 (dd, J=12.7, 2.9 Hz, 1H), 2.33-2.43 (m, 1H), 2.15 (d, J=1.4 Hz, 3H), 1.87-1.91 (m, 1H).

Example 12

3-[(4aR,6R,8aS)-2-Amino-6-(1-methyl-1H-pyrazol-4-yl)-4,4a,5,6-tetrahydropyrano[3,4-d][1,3]thiazin-8a(8H)-yl]-4-fluorobenzonitrile (12)

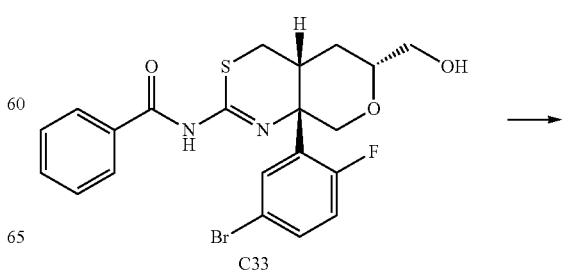

C33

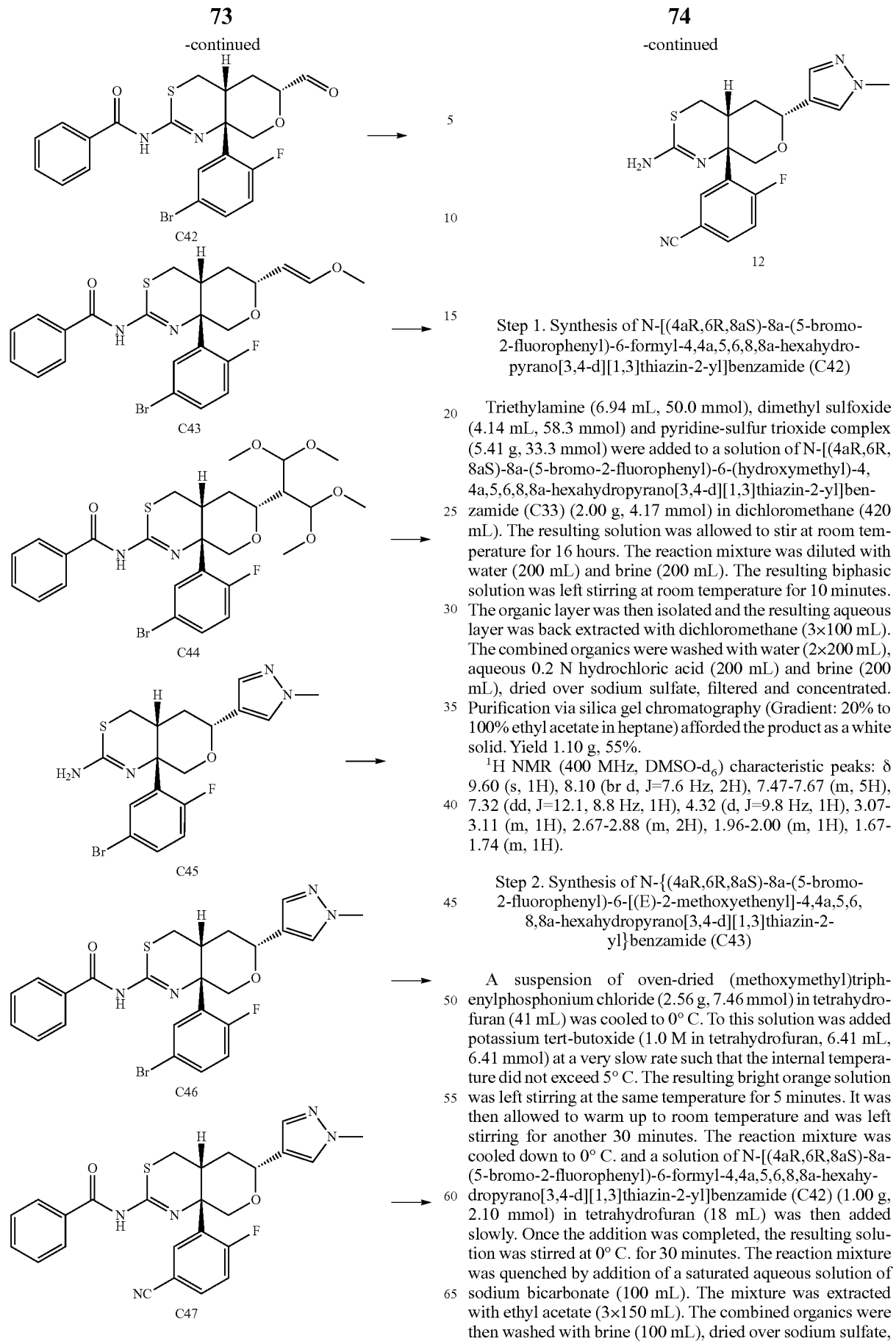

Step 1. Synthesis of N-[(4aR,6R,8aS)-8a-(5-bromo-2-fluorophenyl)-6-formyl-4,4a,5,6,8,8a-hexahydropyrano[3,4-d][1,3]thiazin-2-yl]benzamide (C42)

Triethylamine (6.94 mL, 50.0 mmol), dimethyl sulfoxide (4.14 mL, 58.3 mmol) and pyridine-sulfur trioxide complex (5.41 g, 33.3 mmol) were added to a solution of N-[(4aR,6R,8aS)-8a-(5-bromo-2-fluorophenyl)-6-(hydroxymethyl)-4,4a,5,6,8,8a-hexahydropyrano[3,4-d][1,3]thiazin-2-yl]benzamide (C33) (2.00 g, 4.17 mmol) in dichloromethane (420 mL). The resulting solution was allowed to stir at room temperature for 16 hours. The reaction mixture was diluted with water (200 mL) and brine (200 mL). The resulting biphasic solution was left stirring at room temperature for 10 minutes. The organic layer was then isolated and the resulting aqueous layer was back extracted with dichloromethane (3×100 mL). The combined organics were washed with water (2×200 mL), aqueous 0.2 N hydrochloric acid (200 mL) and brine (200 mL), dried over sodium sulfate, filtered and concentrated. Purification via silica gel chromatography (Gradient: 20% to 100% ethyl acetate in heptane) afforded the product as a white solid. Yield 1.10 g, 55%.

$^1$H NMR (400 MHz, DMSO-$d_6$) characteristic peaks: δ 9.60 (s, 1H), 8.10 (br d, J=7.6 Hz, 2H), 7.47-7.67 (m, 5H), 7.32 (dd, J=12.1, 8.8 Hz, 1H), 4.32 (d, J=9.8 Hz, 1H), 3.07-3.11 (m, 1H), 2.67-2.88 (m, 2H), 1.96-2.00 (m, 1H), 1.67-1.74 (m, 1H).

Step 2. Synthesis of N-{(4aR,6R,8aS)-8a-(5-bromo-2-fluorophenyl)-6-[(E)-2-methoxyethenyl]-4,4a,5,6,8,8a-hexahydropyrano[3,4-d][1,3]thiazin-2-yl}benzamide (C43)

A suspension of oven-dried (methoxymethyl)triphenylphosphonium chloride (2.56 g, 7.46 mmol) in tetrahydrofuran (41 mL) was cooled to 0° C. To this solution was added potassium tert-butoxide (1.0 M in tetrahydrofuran, 6.41 mL, 6.41 mmol) at a very slow rate such that the internal temperature did not exceed 5° C. The resulting bright orange solution was left stirring at the same temperature for 5 minutes. It was then allowed to warm up to room temperature and was left stirring for another 30 minutes. The reaction mixture was cooled down to 0° C. and a solution of N-[(4aR,6R,8aS)-8a-(5-bromo-2-fluorophenyl)-6-formyl-4,4a,5,6,8,8a-hexahydropyrano[3,4-d][1,3]thiazin-2-yl]benzamide (C42) (1.00 g, 2.10 mmol) in tetrahydrofuran (18 mL) was then added slowly. Once the addition was completed, the resulting solution was stirred at 0° C. for 30 minutes. The reaction mixture was quenched by addition of a saturated aqueous solution of sodium bicarbonate (100 mL). The mixture was extracted with ethyl acetate (3×150 mL). The combined organics were then washed with brine (100 mL), dried over sodium sulfate, filtered, and concentrated. Purification via silica gel chromatography (Gradient: 0% to 50% ethyl acetate in heptane) afforded the product as a white solid. Yield: 540 mg, 51%. $^1$H NMR (400 MHz, CD$_3$OD) characteristic peaks: δ 8.13 (br d, J=7.4 Hz, 2H), 7.44-7.57 (m, 4H), 7.13 (dd, J=12.1, 8.6 Hz, 1H), 6.05 (dd, J=6.3, 1.0 Hz, 1H), 4.58-4.63 (m, 1H), 4.48 (dd, J=7.9, 6.4 Hz, 1H), 4.12-4.15 (m, 1H), 3.85 (d, J=11.9 Hz, 1H), 3.63 (s, 3H), 3.20 (br s, 1H), 2.93 (dd, J=13.1, 4.1 Hz, 1H), 2.72 (J=13.2, 2.8 Hz, 1H), 1.84-1.90 (m, 1H), 1.71-1.75 (m, 1H).

Step 3. Synthesis of N-[(4aR,6R,8aS)-8a-(5-bromo-2-fluorophenyl)-6-(1,1,3,3-tetramethoxypropan-2-yl)-4,4a,5,6,8,8a-hexahydropyrano[3,4-d][1,3]thiazin-2-yl]benzamide (C44)

To a solution of N-{(4aR,6R,8aS)-8a-(5-bromo-2-fluorophenyl)-6-[(E)-2-methoxyethenyl]-4,4a,5,6,8,8a-hexahydropyrano[3,4-d][1,3]thiazin-2-yl}benzamide (C43) (0.54 g, 1.1 mmol) in dichloromethane (2 mL) at 0° C., was added trimethyl orthoformate (0.239 mL, 2.19 mmol) followed by drop-wise addition of boron trifluoride-diethyl etherate (0.136 mL, 1.08 mmol), without letting the reaction temperature exceed 3° C. The resulting solution was allowed to stir at the same temperature for 1.5 hours. The reaction mixture was diluted with dichloromethane (200 mL) and a saturated aqueous solution of sodium bicarbonate (200 mL). The organic layer was separated and resulting aqueous layer was extracted with further dichloromethane (200 mL). The combined organics were washed with brine (200 mL), dried over sodium sulfate, filtered and concentrated to give the product (0.65 g) as a white solid, which was taken directly to the following step. $^1$H NMR (400 MHz, CD$_3$OD) characteristic peaks: δ 8.23 (br d, J=7.0 Hz, 2H), 7.41-7.52 (m, 5H), 6.99 (dd, J=1.7, 9.0 Hz, 1H), 4.52 (dd, J=17.7, 4.2 Hz, 1H), 4.13 (d, J=12.5 Hz, 1H), 4.04 (d, J=8.4 Hz, 1H), 3.79 (d, J=11.9 Hz, 1H), 3.13-3.19 (m, 1H), 2.98 (dd, J=13.1, 2.7 Hz, 1H), 2.64 (dd, J=13.1, 1.3 Hz, 1H).

Step 4. Synthesis of (4aR,6R,8aS)-8a-(5-bromo-2-fluorophenyl)-6-(1-methyl-1H-pyrazol-4-yl)-4,4a,5,6,8,8a-hexahydropyrano[3,4-d][1,3]thiazin-2-amine (C45)

Methylhydrazine (0.0834 mL, 1.60 mmol) followed by water (2.2 mL) was added to a solution of N-[(4aR,6R,8aS)-8a-(5-bromo-2-fluorophenyl)-6-(1,1,3,3-tetramethoxypropan-2-yl)-4,4a,5,6,8,8a-hexahydropyrano[3,4-d][1,3]thiazin-2-yl]benzamide (C44) (0.65 g, 1.06 mmol) in ethanol (5 mL). Sulfuric acid (0.110 mL, 2.07 mmol) was then added in a drop-wise manner to the reaction mixture. The resulting solution was heated to 60° C. for 16 hours. The reaction mixture was partitioned between ethyl acetate (100 mL) and a saturated aqueous solution of sodium bicarbonate (100 mL). The layers were separated and the resulting aqueous layer was further extracted with ethyl acetate (3×100 mL). The combined organic layers were then dried over sodium sulfate, filtered and concentrated to give a mixture of product and benzoylated product (0.79 g), which was taken directly to the following step. LCMS m/z 427.1 [M+H$^+$] (product) and m/z 527.1 [M+H$^+$] (benzoylated product).

Step 5. Synthesis of N-[(4aR,6R,8aS)-8a-(5-bromo-2-fluorophenyl)-6-(1-methyl-1H-pyrazol-4-yl)-4,4a,5,6,8,8a-hexahydropyrano[3,4-d][1,3]thiazin-2-yl]benzamide (C46)

A solution of (4aR,6R,8aS)-8a-(5-bromo-2-fluorophenyl)-6-(1-methyl-1H-pyrazol-4-yl)-4,4a,5,6,8,8a-hexahydropyrano[3,4-d][1,3]thiazin-2-amine (C45) (0.79 g, 2.17 mmol) in tetrahydrofuran (10 mL) and methanol (5 mL) was treated with triethylamine (0.488 mL, 3.48 mmol) followed by benzoic anhydride (0.639 g, 2.82 mmol). The resulting homogeneous solution was allowed to stir at room temperature for 16 hours. The reaction mixture was partitioned between water (100 mL) and ethyl acetate (100 mL). The layers were isolated and resulting aqueous layer was further extracted with ethyl acetate (2×100 mL). The combined organics were then washed with water (150 mL), and with brine (150 mL), dried over sodium sulfate and filtered. Purification via silica gel chromatography (Gradient: 30% to 100% ethyl acetate in heptane) afforded the product as an off-white solid. Yield 338 mg, 60% over 2 steps. LCMS m/z 531.2 [M+H$^+$]. $^1$H NMR (400 MHz, CD$_3$OD) characteristic peaks δ 8.13 (br d, J=6.8 Hz, 2H), 7.53-7.62 (m, 3H), 7.45-7.48 (m, 2H), 7.17 (dd, J=12.2, 8.7 Hz, 1H), 5.49 (s, 1H), 4.76 (dd, J=11.5, 2.2 Hz, 1H), 4.27 (d, J=12.1 Hz, 1H), 4.07-4.12 (m, 1H), 3.96-3.93 (d, J=11.9 Hz, 1H), 3.84 (s, 3H), 2.98 (dd, J=13.0, 4.0 Hz, 1H), 2.79 (dd, J=13.1, 2.7 Hz, 1H), 2.12-2.17 (m, 1H), 1.97-2.01 (m, 1H).

Step 6. Synthesis of N-[(4aR,6R,8aS)-8a-(5-cyano-2-fluorophenyl)-6-(1-methyl-1H-pyrazol-4-yl)-4,4a,5,6,8,8a-hexahydropyrano[3,4-d][1,3]thiazin-2-yl]benzamide (C47)

N-[(4aR,6R,8aS)-8a-(5-Bromo-2-fluorophenyl)-6-(1-methyl-1H-pyrazol-4-yl)-4,4a,5,6,8,8a-hexahydropyrano[3,4-d][1,3]thiazin-2-yl]benzamide (C46) was converted to the product using the method described for synthesis of N-[(4aR,6R,8aS)-8a-(5-cyano-2-fluorophenyl)-6-(3-methyl-1,2-oxazol-5-yl)-4,4a,5,6,8,8a-hexahydropyrano[3,4-d][1,3]thiazin-2-yl]benzamide (C37) as in Example 10. The product was obtained as a white solid. Yield: 265 mg, 98%. LCMS m/z 476.2 [M+H$^+$]. $^1$H NMR (400 MHz, CD$_3$OD) characteristic peaks: δ 8.11 (br d, J=7.4 Hz, 2H), 7.98 (br s, 1H), 7.83-7.85 (m, 1H), 7.64-7.67 (m, 3H), 7.54-7.58 (m, 2H), 7.40-7.53 (m, 1H), 4.77 (dd, J=11.4, 2.2 Hz, 1H), 4.25-4.29 (m, 1H), 4.07-4.12 (m, 1H), 3.96 (d, J=11.5 Hz, 1H), 3.84 (s, 3H), 2.93-2.97 (m, 1H), 2.80 (dd, J=13.2, 2.6 Hz, 1H), 2.13-2.120 (m, 1H), 1.97-2.01 (m, 1H).

Step 7. Synthesis of 3-[(4aR,6R,8aS)-2-amino-6-(1-methyl-1H-pyrazol-4-yl)-4,4a,5,6-tetrahydropyrano[3,4-d][1,3]thiazin-8a(8H)-yl]-4-fluorobenzonitrile (12)

1,8-Diazabicycloundec-7-ene (0.298 mL, 1.89 mmol) was added to a solution of N-[(4aR,6R,8aS)-8a-(5-cyano-2-fluorophenyl)-6-(1-methyl-1H-pyrazol-4-yl)-4,4a,5,6,8,8a-hexahydropyrano[3,4-d][1,3]thiazin-2-yl]benzamide (C47) (1.11 g, 2.71 mmol) in methanol (100 mL). The resulting solution was heated to 50° C. for 16 hours. The reaction mixture was concentrated under reduced pressure. Purification via silica gel chromatography (Gradient: 0% to 20% methanol in dichloromethane) afforded the product as an off-white solid. Yield: 79 mg, 38%. LCMS m/z 372.2 [M+H$^+$]. $^1$H NMR (400 MHz, CD$_3$OD) δ 7.77 (ddd, J=8.5, 4.5, 2.2 Hz, 1H), 7.69 (dd, J=7.2, 2.2 Hz, 1H), 7.60 (s, 1H), 7.47 (s, 1H), 7.36 (dd, J=12.1, 8.6 Hz, 1H), 4.71 (dd, J=11.6, 2.2 Hz, 1H), 4.24 (dd, J=11.2, 2.3 Hz, 1H), 3.87 (s, 3H), 3.76 (d, J=11.2 Hz, 1H), 3.06-3.11 (m, 1H), 2.89 (dd, J=12.5, 4.1 Hz, 1H), 2.76 (dd, J=12.7, 2.7 Hz, 1H), 2.04-2.14 (m, 1H), 1.82-1.87 (m, 1H).

Example 13
3-[(4aR,6R,8aS)-2-Amino-6-cyclopropyl-4,4a,5,6-tetrahydropyrano[3,4-d][1,3]thiazin-8a(8H)-yl]-4-fluorobenzonitrile (13)
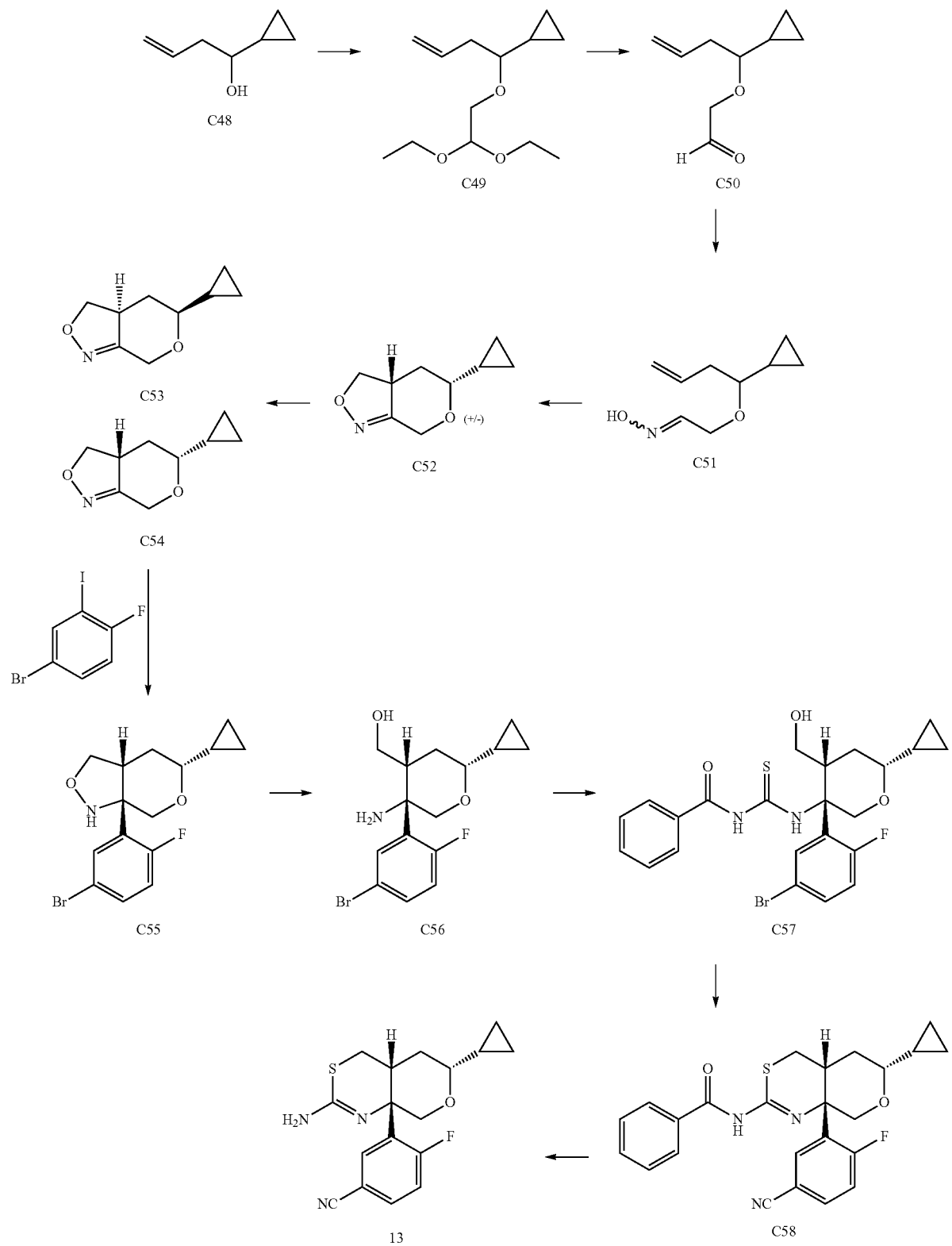

Step 1. Synthesis of [1-(2,2-diethoxyethoxy)but-3-en-1-yl]cyclopropane (C49)

1-Cyclopropylbut-3-en-1-ol (C48, see C. Tahtaoui et al., *J. Org. Chem.* 2010, 75, 3781-3785) (92%, 8.1 g, 66 mmol) was added to a 0° C. suspension of sodium hydride (60% in mineral oil, 8.25 g, 206 mmol) in tetrahydrofuran (105 mL). The cooling bath was removed and the suspension was stirred until the internal temperature reached 21° C. The reaction mixture was then cooled in an ice bath, and 2-bromo-1,1-diethoxyethane (97%, 18.5 mL, 119 mmol) was added drop-wise at a rate that maintained the internal temperature below 5° C. After warming to room temperature, the reaction mixture was heated to 58° C. for 27 hours. Sodium hydride (60% in mineral oil, 3.3 g, 83 mmol) and 2-bromo-1,1-diethoxyethane (97%, 10 mL, 64 mmol) were added again, and the reaction mixture was heated at mild reflux for 14 hours. It was then cooled to 0° C., slowly quenched with water (100 mL) and extracted with diethyl ether (3×200 mL). The combined organic layers were dried over sodium sulfate, filtered, and concentrated in vacuo; purification via silica gel chromatography (Gradient: 0% to 10% ethyl acetate in heptane) afforded the product as a colorless oil. Yield: 12.1 g, 53.0 mmol, 80%. $^1$H NMR (400 MHz, CDCl$_3$) δ 5.87-5.98 (m, 1H), 5.05-5.11 (m, 1H), 5.00-5.04 (m, 1H), 4.61 (t, J=5.3 Hz, 1H), 3.66-3.75 (m, 3H), 3.54-3.62 (m, 2H), 3.47 (dd, J=10.3, 5.5 Hz, 1H), 2.70 (dt, J=8.4, 6.0 Hz, 1H), 2.36-2.41 (m, 2H), 1.22 (t, J=7.0 Hz, 3H), 1.22 (t, J=7.0 Hz, 3H), 0.80-0.90 (m, 1H), 0.54-0.62 (m, 1H), 0.35-0.50 (m, 2H), 0.07-0.14 (m, 1H).

Step 2. Synthesis of [(1-cyclopropylbut-3-en-1-yl)oxy]acetaldehyde (C50)

A mixture of [1-(2,2-diethoxyethoxy)but-3-en-1-yl]cyclopropane (C49) (2.97 g, 13.0 mmol), aqueous hydrochloric acid (1 M, 39 mL, 39 mmol) and tetrahydrofuran (39 mL) was stirred at room temperature for 12.5 hours, then heated to 40° C. for 3 hours. The reaction mixture was cooled to room temperature and slowly transferred into a stirring biphasic mixture of saturated aqueous sodium bicarbonate solution (200 mL) and diethyl ether (200 mL). The aqueous layer was extracted with diethyl ether (2×100 mL) and the combined organic extracts were dried over sodium sulfate, filtered, and concentrated in vacuo (900 mbar, 60° C.) to afford the product as a colorless oil (3.63 g), which contained residual diethyl ether and tetrahydrofuran by $^1$H NMR analysis. This material was taken directly into the following step. $^1$H NMR (400 MHz, CDCl$_3$) δ 9.76-9.78 (m, 1H), 5.86-5.98 (m, 1H), 5.04-5.15 (m, 2H), 4.15 (br AB quartet, J$_{AB}$=17.8 Hz, Δν$_{AB}$=22.8 Hz, 2H), 2.71 (dt, J=8.8, 5.9 Hz, 1H), 2.41-2.47 (m, 2H), 0.81-0.91 (m, 1H), 0.58-0.66 (m, 1H), 0.49-0.57 (m, 1H), 0.31-0.38 (m, 1H), 0.08-0.15 (m, 1H).

Step 3. Synthesis of 2-[(1-cyclopropylbut-3-en-1-yl)oxy]-N-hydroxyethanimine (C51)

[(1-Cyclopropylbut-3-en-1-yl)oxy]acetaldehyde (C50) (3.63 g from the previous step, ≤13.0 mmol) was dissolved in a 2:1 mixture of ethanol and water (39 mL). Sodium acetate (5.32 g, 64.9 mmol) was added; after the reaction mixture had been stirred for 15 minutes, hydroxylamine hydrochloride (98%, 2.76 g, 38.9 mmol) was added. The reaction mixture was heated to 60° C. for 5 minutes, at which time water (4×1 mL) was added until a solution formed. After 1 hour at 60° C., the reaction mixture was cooled, concentrated under reduced pressure to remove ethanol, and diluted with saturated aqueous sodium chloride solution (100 mL). The mixture was extracted with diethyl ether (3×100 mL), and the combined organic layers were dried over sodium sulfate, filtered, and concentrated in vacuo at 22° C. Silica gel chromatography (Gradient: 0% to 25% ethyl acetate in heptane) provided the product as a thick, opaque oil. By $^1$H NMR analysis, this material consisted of a roughly 1:1 mixture of E and Z oxime isomers. Yield: 1.771 g, 10.47 mmol, 81% over two steps. $^1$H NMR (400 MHz, CDCl$_3$) δ [7.50 (dd, J=5.7, 5.6 Hz) and 6.92-6.99 (m), total 1H], 5.84-5.97 (m, 1H), 5.03-5.15 (m, 2H), {[4.53 (dd, half of ABX pattern, J=16.4, 3.5 Hz) and 4.41 (dd, half of ABX pattern, J=16.4, 3.6 Hz)] and [4.27 (dd, half of ABX pattern, J=12.9, 5.5 Hz) and 4.16 (dd, half of ABX pattern, J=12.9, 5.8 Hz)], total 2H}, 2.65-2.74 (m, 1H), 2.37-2.44 (m, 2H), 0.81-0.91 (m, 1H), 0.59-0.68 (m, 1H), 0.47-0.56 (m, 1H), 0.35-0.44 (m, 1H), 0.07-0.15 (m, 1H).

Step 4. Synthesis of rel-(3aR,5R)-5-cyclopropyl-3,3a,4,5-tetrahydro-7H-pyrano[3,4-c][1,2]oxazole (C52)

An aqueous solution of sodium hypochlorite (6.15% solution, 27.1 mL, 22.4 mmol) was added drop-wise over 24 minutes to a solution of 2-[(1-cyclopropylbut-3-en-1-yl)oxy]-N-hydroxyethanimine (C51) (1.85 g, 10.9 mmol) and triethylamine (0.114 mL, 0.818 mmol) in dichloromethane (64 mL) that was immersed in a room temperature water bath. The rate of addition was adjusted to maintain the internal temperature of the reaction between 19.5° C. and 22.8° C. After completion of the addition, the reaction mixture was diluted with water (50 mL) and the aqueous layer was extracted with dichloromethane (3×50 mL). The combined organic layers were washed with saturated aqueous sodium chloride solution (50 mL), dried over sodium sulfate, filtered, and concentrated in vacuo (300 mbar, 40° C.) to provide the product as a pale yellow oil. The indicated relative stereochemistry of compound C52 was assigned based on nuclear Overhauser enhancement studies, which revealed an interaction between the methine protons on carbons 3a and 5. Yield: 1.73 g, 10.3 mmol, 94%. GCMS m/z 167 [M$^+$]. $^1$H NMR (400 MHz, CDCl$_3$) δ 4.73 (d, J=13.5 Hz, 1H), 4.61 (dd, J=10.2, 8.0 Hz, 1H), 4.14 (dd, J=13.5, 1.0 Hz, 1H), 3.80 (dd, J=11.5, 8.0 Hz, 1H), 3.36-3.48 (m, 1H), 2.83 (ddd, J=11.0, 8.0, 1.8 Hz, 1H), 2.31 (ddd, J=13.0, 6.5, 1.5 Hz, 1H), 1.64 (ddd, J=12.8, 11.4, 11.3 Hz, 1H), 0.89-0.98 (m, 1H), 0.51-0.64 (m, 2H), 0.38-0.45 (m, 1H), 0.21-0.28 (m, 1H).

Step 5. Preparation of (3aS,5S)-5-cyclopropyl-3,3a, 4,5-tetrahydro-7H-pyrano[3,4-c][1,2]oxazole and (3aR,5R)-5-cyclopropyl-3,3a,4,5-tetrahydro-7H-pyrano[3,4-c][1,2]oxazole (C53 and C54)

Racemic rel-(3aR,5R)-5-cyclopropyl-3,3a,4,5-tetrahydro-7H-pyrano[3,4-c][1,2]oxazole (C52) (20 g, 0.12 mol) was separated into its enantiomers using supercritical fluid chromatography (Column: ChiralPAK® AS-H, 5 µm; Eluent: 9:1 carbon dioxide/methanol). The second-eluting enantiomer provided (3aR,5R)-5-cyclopropyl-3,3a,4,5-tetrahydro-7H-pyrano[3,4-c][1,2]oxazole as a pale yellow solid. The indicated absolute stereochemistry was assigned to compound C54 on the basis of the biological activity of this compound's final targets, which proved active (Table 1).

The first-eluting enantiomer provided (3aS,5S)-5-cyclopropyl-3,3a,4,5-tetrahydro-7H-pyrano[3,4-c][1,2]oxazole as a pale yellow solid. Yield: 8.97 g, 0.053 mol, 44%. GCMS m/z 167 [M+]. $^1$H NMR (400 MHz, CDCl$_3$) δ 4.69 (d, J=13.5 Hz, 1H), 4.57 (ddd, J=10.2, 7.9, 0.7 Hz, 1H), 4.14 (dt, J=13.4, 1.0 Hz, 1H), 3.77 (dd, J=11.8, 7.7 Hz, 1H), 3.39 (qd, J=11.1, 6.7, 1H), 2.81 (ddd, J=10.3, 8.7, 1.4 Hz, 1H), 2.28 (ddd, J=13.1, 6.5, 1.6 Hz, 1H), 1.64 (ddd, J=12.8, 11.4, 11.3 Hz, 1H), 0.86-0.95 (m, 1H), 0.49-0.61 (m, 2H), 0.36-0.42 (m, 1H), 0.19-0.25 (m, 1H).

The second-eluting enantiomer provided (3aR,5R)-5-cyclopropyl-3,3a,4,5-tetrahydro-7H-pyrano[3,4-c][1,2]oxazole as a pale yellow solid. Yield: 8.75 g, 52.3 mmol, 44%. GCMS m/z 167 [M+]. $^1$H NMR (400 MHz, CDCl$_3$) δ 4.51 (d, J=13.7 Hz, 1H), 4.39 (dd, J=10.3, 8 Hz, 1H), 3.92 (dd, J=13.7, 1.2 Hz, 1H), 3.58 (dd, J=11.7, 8.2 Hz, 1H), 3.19 (qd, J=11.1, 6.4 Hz, 1H), 2.61 (ddd, J=11.1, 8, 1.6 Hz, 1H), 2.08 (ddd, J=13, 6.5, 1.6 Hz, 1H), 1.38-1.46 (m, 1H), 0.718 (qt, J=8.1, 4.9 Hz, 1H), 0.31-0.42 (m, 2H), 0.17-0.23 (m, 1H), 0.0-0.06 (m, 1H).

Step 6. Synthesis of (3aR,5R,7aS)-7a-(5-bromo-2-fluorophenyl)-5-cyclopropylhexahydro-1H-pyrano [3,4-c][1,2]oxazole (C55)

A solution of (3aR,5R)-5-cyclopropyl-3,3a,4,5-tetrahydro-7H-pyrano[3,4-c][1,2]oxazole (C54) (180 mg, 1.08 mmol) in toluene (7 mL) was cooled to −78° C. Boron trifluoride-diethyl etherate (46.5%, 0.318 mL, 1.18 mmol) was added and the reaction was stirred at −78° C. for 15 minutes. A solution of 4-cyano-1-fluoro-2-bromobenzene (237 mg, 1.18 mmol) in toluene (2 mL) was slowly added and the reaction was stirred for 5 minutes. tert-Butyllithium (1.7 M in toluene, 1.39 mL, 2.37 mmol) was added drop-wise and the reaction was allowed to stir at −78° C. for 1.25 hours. The reaction was quenched by addition of a saturated aqueous solution of ammonium chloride (5 mL) and allowed to warm to room temperature. The mixture was diluted with water (5 mL) and extracted with ethyl acetate (2×50 mL). The organics were combined, dried over magnesium sulfate, filtered and concentrated to give the product, which was taken directly to the following step. LCMS m/z 289.2 [M+H+].

Step 7. Synthesis of [(2R,4R,5S)-5-amino-5-(5-bromo-2-fluorophenyl)-2-cyclopropyltetrahydro-2H-pyran-4-yl]methanol (C56)

Zinc dust (1.06 g, 16.2 mmol) was added to a solution of (3aR,5R,7aS)-7a-(5-bromo-2-fluorophenyl)-5-cyclopropyl-hexahydro-1H-pyrano[3,4-c][1,2]oxazole (C55) (311 mg, 1.08 mmol) in acetic acid (56 mL). The reaction mixture was allowed to stir at room temperature overnight. The reaction was filtered through an empty Bakerbond cartridge, eluting with ethyl acetate to remove the zinc. The filtrate was concentrated and then passed through a 4 g methanol-conditioned MCX cartridge. This was washed with methanol (4×15 mL), dichloromethane (4×15 mL) and 2 N ammonia in methanol (40 mL). The filtrate was concentrated in vacuo to give the product (225 mg), which was taken directly to the following step. LCMS m/z 291.2 [M+H+].

Step 8. Synthesis of N-{[(3S,4R,6R)-3-(5-bromo-2-fluorophenyl)-6-cyclopropyl-4-(hydroxymethyl)tetrahydro-2H-pyran-3-yl]carbamothioyl}benzamide (C57)

Benzoyl isothiocyanate (120 mg, 0.74 mmol) was added drop-wise to a solution of [(2R,4R,5S)-5-amino-5-(5-bromo-2-fluorophenyl)-2-cyclopropyltetrahydro-2H-pyran-4-yl] methanol (C56) (from the previous step, 225 mg, 50.78 mmol) in dichloromethane (25 mL) at 0° C. The reaction mixture was allowed to stir at 0° C. for 1.5 hours, then was warmed to room temperature and stirred overnight before concentrating in vacuo. Purification via silica gel chromatography (Gradient: 0% to 100% ethyl acetate in heptane) afforded the product as a solid. Yield: 127 mg, 26% over 2 steps LCMS m/z 454.3 [M+H+].

Step 9. Synthesis of N-[(4aR,6R,8aS)-8a-(5-cyano-2-fluorophenyl)-6-cyclopropyl-4,4a,5,6,8,8a-hexahydropyrano[3,4-d][1,3]thiazin-2-yl]benzamide (C58)

A solution of N-{[(3S,4R,6R)-3-(5-bromo-2-fluorophenyl)-6-cyclopropyl-4-(hydroxymethyl)tetrahydro-2H-pyran-3-yl]carbamothioyl}benzamide (C57) (127 mg, 0.28 mmol) and pyridine (81 µL, 1.01 mmol) in dichloromethane (12 mL) was cooled to −50° C. Trifluoromethanesulfonic anhydride (94 µL, 0.56 mmol) was added drop-wise to the solution and the mixture was gradually warmed to 0° C. over 90 minutes. The reaction mixture was diluted with dichloromethane (20 mL), washed with water (2×30 mL), dried over magnesium sulfate, filtered, and concentrated in vacuo. Purification via silica gel chromatography (Gradient: 0% to 100% ethyl acetate in heptane) afforded the product as a solid. Yield: 83 mg, 68%. LCMS m/z 436.2 [M+H⁺].

Step 10. Synthesis of 3-[(4aR,6R,8aS)-2-amino-6-cyclopropyl-4,4a,5,6-tetrahydropyrano[3,4-d][1,3]thiazin-8a(8H)-yl]-4-fluorobenzonitrile (13)

Hydrazine monohydrate (0.101 mL, 1.34 mmol) was added to a solution of N-[(4aR,6R,8aS)-8a-(5-cyano-2-fluorophenyl)-6-cyclopropyl-4,4a,5,6,8,8a-hexahydropyrano[3,4-d][1,3]thiazin-2-yl]benzamide (C58) (83 mg, 0.19 mmol) in ethanol (4 mL). The reaction mixture was allowed to stir at room temperature overnight and was then concentrated in vacuo. The residue was purified by reverse phase chromatography to provide the product as a white solid. Yield: 40.3 mg, 64%. Column: Waters XBridge C18, 19×100 mm, 5 μm; Mobile phase A: 0.03% ammonium hydroxide in water (v/v); Mobile phase B: 0.03% ammonium hydroxide in acetonitrile (v/v); Gradient: 20.0% acetonitrile to 60% B, linear over 8.5 minutes; Flow rate: 25 mL/min. LCMS m/z 332.1868 [M+H⁺]. QC retention time: 1.92 minutes (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/min).

Example 14

3-[(4aR,6S,8aS)-2-Amino-6-methyl-4,4a,5,6-tetrahydropyrano[3,4-d][1,3]thiazin-8a(8H)-yl]-4-fluorobenzonitrile (14)

Step 1. Synthesis of 4-fluoro-3-[(3aR,5S,7aS)-5-methyltetrahydro-1H-pyrano[3,4-c][1,2]oxazol-7a(7H)-yl]benzonitrile (C59)

To a mixture of 3-bromo-4-fluorobenzonitrile (22.3 g, 112 mmol) dissolved in a 10:1 toluene-tetrahydrofuran mixture (530 mL) cooled to −78° C. was added n-butyllithium (2.5 M in hexanes, 42.5 mL, 106 mmol) drop-wise. The reaction mixture was stirred at −78° C. for 1 hour at which point a solution of P2 (7.5 g, 53 mmol) in 10:1 toluene-tetrahydrofuran (177 mL) and boron trifluoride-diethyl etherate complex (46.5%, 13.3 mL, 50.1 mmol) were simultaneously added drop-wise. The reaction mixture was stirred at −78° C. for 2 hours, at which point a solution of saturated aqueous ammonium chloride was added. The reaction mixture was warmed to room temperature and the aqueous was extracted three times with ethyl acetate. The combined organic layers were washed with water and with brine, dried over sodium sulfate, filtered and concentrated. Silica gel chromatography (Gradient: 0% to 50% ethyl acetate in heptane) provided the product as a yellow oil that solidified over time. Yield: 11.4 g, 45.1 mmol, 85%. LCMS m/z 263.3 [M+H⁺]. ¹H NMR (400 MHz, CDCl₃), δ 8.34 (dd, J=7.3, 2.2 Hz, 1H), 7.60 (ddd, J=8.5, 4.6, 2.3 Hz, 1H), 7.16 (dd, J=11.5, 8.4 Hz, 1H), 4.10 (dd, J=12.5, 2.2 Hz, 1H), 3.80 (br d, J=12.7 Hz, 1H), 3.68-3.77 (m, 2H), 3.51 (dd, J=7.2, 5.1 Hz, 1H), 3.08 (dddd, J=11.5, 6.8, 4.9, 1.9 Hz, 1H), 1.88 (ddd, J=14.2, 6.9, 2.2 Hz, 1H), 1.41-1.50 (m, 1H), 1.27 (d, J=6.1, 3H).

Step 2. Synthesis of 3-[(3S,4R,6S)-3-amino-4-(hydroxymethyl)-6-methyltetrahydro-2H-pyran-3-yl]-4-fluorobenzonitrile (C60)

To a solution of C59 (23.5 g, 89.8 mmol) in glacial acetic acid (428 mL) was added zinc dust (58.7 g, 898 mmol). The

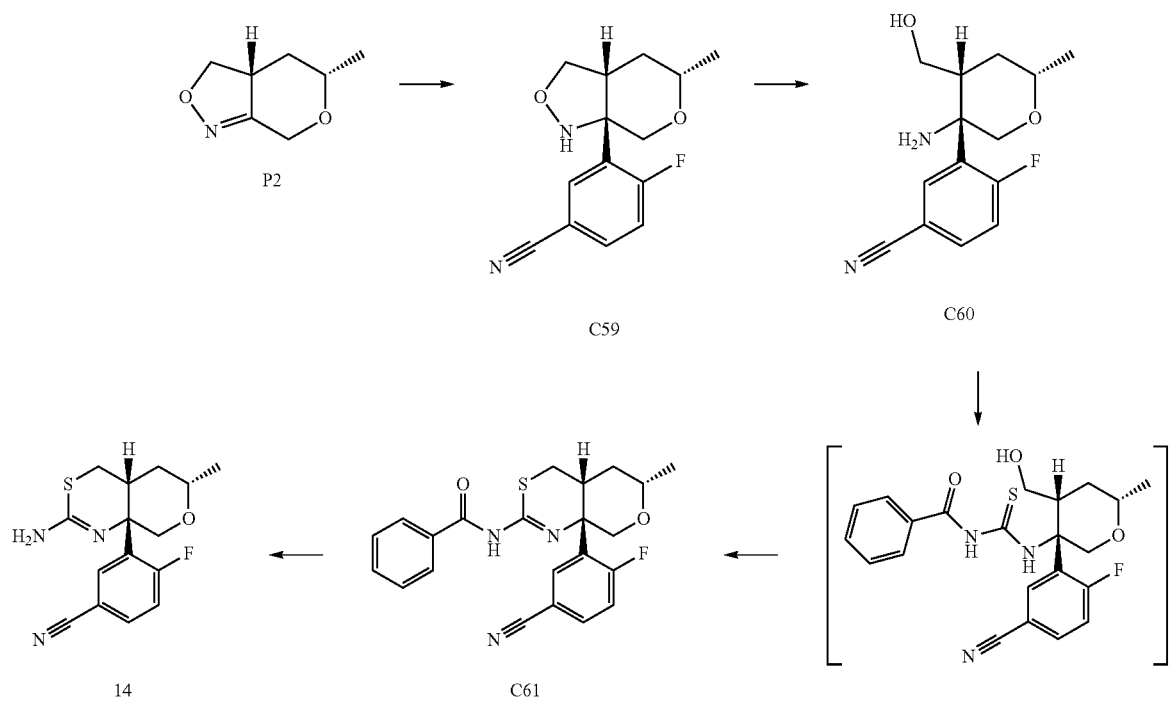

reaction mixture was allowed to stir at 40° C. for 16 hours. The reaction mixture was filtered through a Celite pad with ethyl acetate (3×500 mL). The combined filtrate was washed with 1 N aqueous sodium hydroxide (900 mL). The organic layer was removed and the aqueous washed with ethyl acetate (3×250 mL). The combined organics were washed with brine (1×500 mL), dried over sodium sulfate, filtered and concentrated in vacuo to provide 10 g of product as a yellow oil. To the aqueous layer from the extraction was added 1 N aqueous sodium hydroxide until a pH of 9 was achieved. The resulting aqueous was extracted with dichloromethane (3×500 mL) and the combined organics were washed with brine (1×1000 mL), dried over sodium sulfate, filtered and concentrated in vacuo to provide 13.5 g of product as a yellow oil. Yield: 23.5 g, 88.9 mmol, 99%. $^1$H NMR (400 MHz, CDCl$_3$), δ 8.12 (dd, J=7.1, 2.1 Hz, 1H), 7.63 (ddd, J=8.4, 4.5, 2.2 Hz, 1H), 7.16 (dd, J=11.8, 8.5 Hz, 1H), 4.16 (dd, J=11.3, 2.7 Hz, 1H), 3.72 (dqd, J=11.7, 6.1, 2.6 Hz, 1H), 3.44-3.48 (m, 1H), 3.35-3.39 (m, 2H), 2.36 (dq, J=12.7, 3.6 Hz, 1H), 1.83-1.93 (m, 1H), 1.71 (ddd, J=14.2, 4.4, 2.7 Hz, 1H), 1.33 (d, J=6.3 Hz, 3H).

Step 3. Synthesis of N-[(4aR,6S,8aS)-8a-(5-cyano-2-fluorophenyl)-6-methyl-4,4a,5,6,8,8a-hexahydropyrano[3,4-d][1,3]thiazin-2-yl]benzamide (C61)

To C60 (20.47 g, 77.45 mmol) dissolved in dichloromethane (774 mL) was added benzoyl isothiocyanate (10.3 mL, 76.7 mmol). The resulting solution was stirred at room temperature for 18 hours at which point Ghosez's reagent (26.7 mL, 194 mmol) was added. The reaction mixture was allowed to stir at room temperature for 2 hours at which point saturated aqueous sodium bicarbonate (500 mL) was added. The aqueous was removed and the organic layer was washed with water (3×500 mL) and with brine (500 mL), dried over sodium sulfate, filtered and concentrated in vacuo to provide a yellow solid. The solids were triturated with ethyl acetate (100 mL) to provide a white solid that was washed with ethyl acetate (2×50 mL) and dried in vacuo. Yield: 23.3 g, 56.9 mmol, 74%. LCMS m/z 410.2 [M+H$^+$]. $^1$H NMR (400 MHz, CD$_3$OD), δ 8.08-8.15 (m, 2H), 7.79-7.84 (m, 2H), 7.54-7.58 (m, 1H), 7.46-7.49 (m, 2H), 7.4 (dd, J=12, 8.5 Hz, 1H), 4.11 (dd, J=11.9, 1.8 Hz, 1H), 3.86 (d, J=11.7 Hz, 1H), 3.77-3.85 (m, 1H), 3.14-3.21 (m, 1H), 2.91 (dd, J=13.9, 3.1 Hz, 1H), 2.73 (dd, J=13.2, 2.8 Hz, 1H), 1.70-1.83 (m, 2H), 1.26 (d, J=6.1, 3H).

Step 4. Synthesis of 3-[(4aR,6S,8aS)-2-amino-6-methyl-4,4a,5,6-tetrahydropyrano[3,4-d][1,3]thiazin-8a(8H)-yl]-4-fluorobenzonitrile (14)

To C61 (5.96 g, 14.6 mmol) in methanol (539 mL) was added 1,8-diazabicycloundec-7-ene (1.60 mL, 10.1 mmol) and the reaction mixture was heated at 50° C. for 16 hours. Glacial acetic acid (1.48 mL) was added and the reaction mixture was concentrated in vacuo. The residue was dissolved with dichloromethane (200 mL) at which point saturated aqueous sodium bicarbonate (500 mL) was added. The organic layer was removed and the aqueous was extracted with dichloromethane (3×100 mL). The organics were combined and washed with brine (250 mL), dried over sodium sulfate, filtered and concentrated on silica gel. Silica gel chromatography (Gradient: 0% to 100% ethyl acetate in heptane) provided the product as a white solid. Yield: 3.25 g, 10.65 mmol, 73%. LCMS m/z 306.1 [M+H$^+$]. $^1$H NMR (400 MHz, CD$_3$OD), δ 7.74 (ddd, J=8.4, 4.4, 2.2 Hz, 1H), 7.65 (dd, J=7.2, 2.2 Hz, 1H), 7.31 (dd, J=12.1, 8.4 Hz, 1H), 4.07 (dd, J=11.1, 2.4 Hz, 1H), 3.7-3.78 (m, 1H), 3.64 (d, J=11.2 Hz, 1H), 2.92 (dtd, J=11.9, 4.3, 2.9 Hz, 1H), 2.80-2.84 (m, 1H), 2.67 (dd, J=12.6, 2.8 Hz, 1H), 1.66-1.76 (m, 1H), 1.55 (ddd, J=13.1, 4.2, 2.4 Hz, 1H), 1.22 (d, J=6.1 Hz, 3H).

Example 15

(4aR,6R,8aS)-6-(Fluoromethyl)-8a-(2-fluoro-5-{[(2,2,2-trifluoroethyl)amino]methyl}phenyl)-4,4a,5,6,8,8a-hexahydropyrano[3,4-d][1,3]thiazin-2-amine (15)

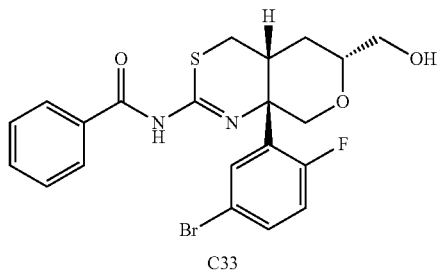

C33

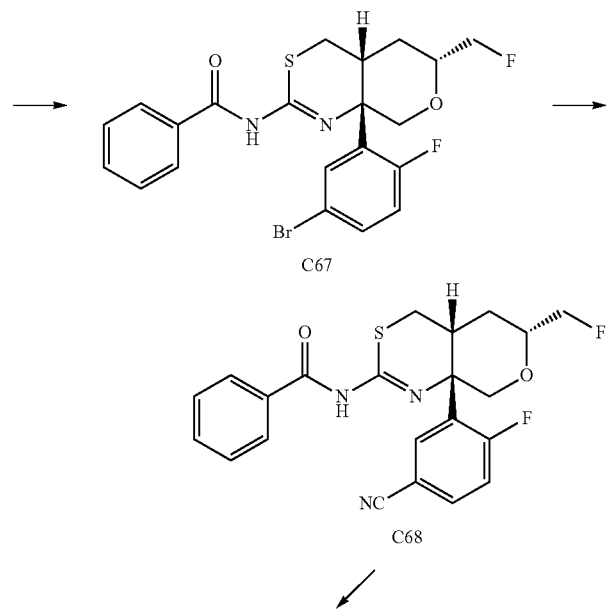

C67

C68

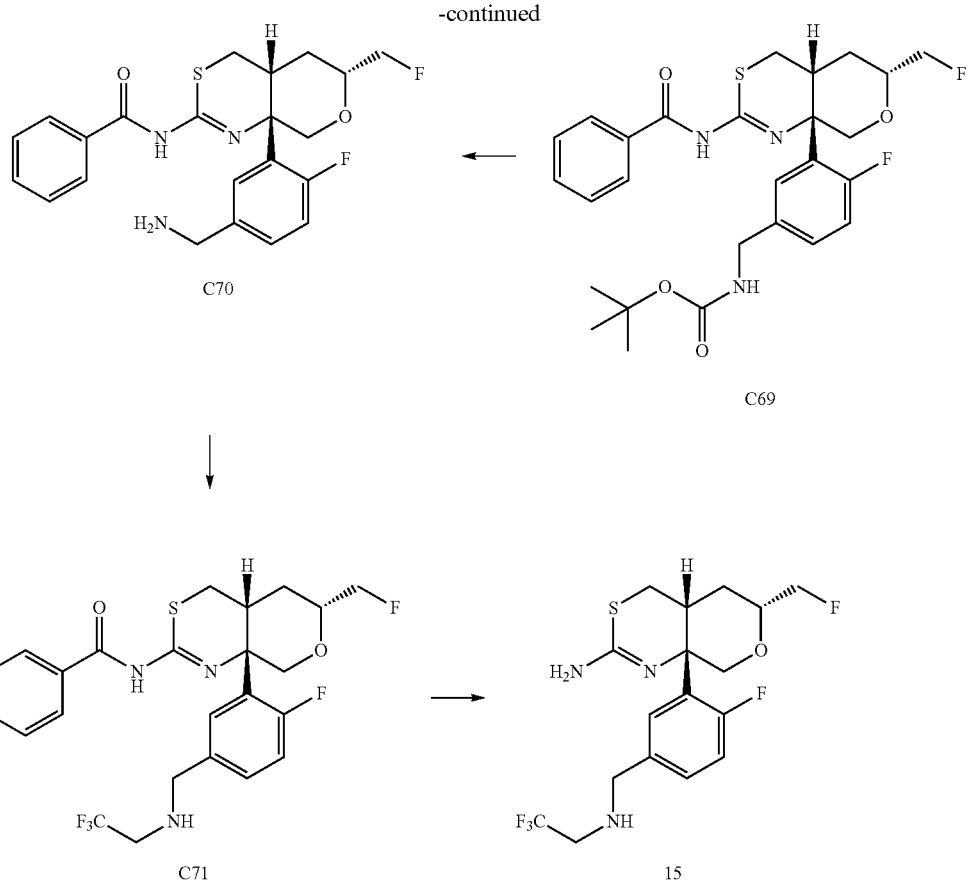

Step 1. Synthesis of N-[(4aR,6R,8aS)-8a-(5-bromo-2-fluorophenyl)-6-(fluoromethyl)-4,4a,5,6,8,8a-hexahydropyrano[3,4-d][1,3]thiazin-2-yl]benzamide (C67)

Diethylaminosulfur trifluoride (0.434 mL, 3.28 mmol) was added to a mixture of pentanes (20 mL) and dichloromethane (31 mL). To the resulting solution was added C33 (525 mg, 1.10 mmol) in dichloromethane (21 mL; it was necessary to apply mild heat to this mixture to afford a solution, and to use the solution promptly) in a drop-wise manner, whereupon the reaction mixture was allowed to stir at room temperature for 16 hours. Saturated aqueous sodium bicarbonate solution (100 mL) was added and the aqueous layer was extracted with dichloromethane (3×50 mL). The combined organic layers were washed with saturated aqueous sodium chloride solution (100 mL), dried over sodium sulfate, filtered, and concentrated in vacuo; silica gel chromatography (Gradient: 20% to 100% ethyl acetate in heptane) provided the product as a white solid. Yield: 166 mg, 0.345 mmol, 31%. LCMS m/z 481.2, 483.2 [M+H$^+$]. $^1$H NMR (400 MHz, CD$_3$OD) δ 8.08-8.17 (br m, 2H), 7.52-7.60 (m, 3H), 7.47 (br dd, J=7.7, 7.3, 2H), 7.17 (dd, J=12.2, 8.7 Hz, 1H), 4.34-4.42 and 4.46-4.54 (2 m, J$_{HF}$=47.3 and 47.8 Hz, total 2H), 4.15 (dd, J=11.9, 1.6 Hz, 1H), 3.92-4.04 (br m, 1H), 3.92 (d, J=11.9 Hz, 1H), 3.18-3.28 (br m, 1H), 2.96 (dd, J=13, 4 Hz, 1H), 2.77 (dd, J=13, 3 Hz, 1H), 1.84-1.96 (m, 1H), 1.66-1.73 (m, 1H).

Step 2. Synthesis of N-[(4aR,6R,8aS)-8a-(5-cyano-2-fluorophenyl)-6-(fluoromethyl)-4,4a,5,6,8,8a-hexahydropyrano[3,4-d][1,3]thiazin-2-yl]benzamide (C68)

Conversion of C67 to the product, which was isolated as a light yellow solid, was carried out using the method described for synthesis of C10 in Example 1. Yield: 143 mg, 0.334 mmol, 97%. LCMS m/z 428.2 [M+H$^+$]. $^1$H NMR (400 MHz, CD$_3$OD) δ 8.05-8.15 (br m, 2H), 7.79-7.86 (m, 2H), 7.57 (br dd, J=7.4, 7.1 Hz, 1H), 7.49 (br dd, J=7.6, 7.1 Hz, 2H), 7.41 (dd, J=12.1, 8.7 Hz, 1H), 4.35-4.42 and 4.47-4.54 (m, J$_{HF}$=47.4 and 47.8 Hz, total 2H), 4.15 (dd, J=11.8, 1.9 Hz, 1H), 3.94-4.05 (br m, 1H), 3.94 (d, J=11.8 Hz, 1H), 3.18-3.28 (br m, 1H), 2.94 (dd, J=13, 4 Hz, 1H), 2.77 (dd, J=13, 3 Hz, 1H), 1.85-1.97 (m, 1H), 1.67-1.74 (m, 1H).

Step 3. Synthesis of tert-butyl {3-[(4aR,6R,8aS)-2-(benzoylamino)-6-(fluoromethyl)-4,4a,5,6-tetrahydropyrano[3,4-d][1,3]thiazin-8a(8H)-yl]-4-fluorobenzyl}carbamate (C69)

Compound C68 (143 mg, 0.334 mmol) was converted to the product using the method described for synthesis of C25 in Example 8. In this case, addition of tetrahydrofuran to the initial mixture of C68 and methanol was required in order to obtain a solution. The product (235 mg) was obtained as a brown solid, contaminated with unreacted starting material; this mixture was carried directly into the following step. LCMS m/z 532.3 [M+H$^+$].

Step 4. Synthesis of N-[(4aR,6R,8aS)-8a-[5-(aminomethyl)-2-fluorophenyl]-6-(fluoromethyl)-4,4a,5,6,8,8a-hexahydropyrano[3,4-d][1,3]thiazin-2-yl]benzamide (C70)

Compound C69 (235 mg, from the previous step) was converted to the product using the method described for synthesis of C26 in Example 8. The product (100 mg), obtained as a brown solid, was carried directly to the following step. LCMS m/z 432.3 [M+H$^+$].

Step 5. Synthesis of N-[(4aR,6R,8aS)-6-(fluoromethyl)-8a-(2-fluoro-5-{[(2,2,2-trifluoroethyl)amino]methyl}phenyl)-4,4a,5,6,8,8a-hexahydropyrano[3,4-d][1,3]thiazin-2-yl]benzamide (C71)

Compound C70 (100 mg, from the previous step) was converted to the product using the method described for synthesis of C27 in Example 8, providing the product as a white solid. Yield: 23 mg, 45 μmol, 13% over three steps. LCMS m/z 514.3 [M+H$^+$]. $^1$H NMR (400 MHz, CDCl$_3$) δ 8.23 (d, J=7.3 Hz, 2H), 7.53 (br dd, J=7.2, 7.1 Hz, 1H), 7.46 (br dd, J=7.7, 7.0 Hz, 2H), 7.37-7.43 (m, 1H), 7.31 (br dd, J=7.6, 1.7 Hz, 1H), 7.11 (dd, J=12.2, 8.3 Hz, 1H), 4.50 (ddd, J=47.5, 9.8, 6.3 Hz, 1H), 4.42 (ddd, J=46.7, 9.8, 3.8 Hz, 1H), 4.22 (br d, J=12.2 Hz, 1H), 3.96-4.07 (m, 1H), 3.84-3.92 (m, 3H), 3.21-3.29 (m, 1H), 3.16 (q, J$_{HF}$=9.4 Hz, 2H), 3.04 (dd, J=13.0, 3.9 Hz, 1H), 2.66 (dd, J=12.9, 2.9 Hz, 1H), 1.94-2.07 (m, 1H), 1.63-1.72 (m, 1H).

Step 6. Synthesis of (4aR,6R,8aS)-6-(fluoromethyl)-8a-(2-fluoro-5-{[(2,2,2-trifluoroethyl)amino]methyl}phenyl)-4,4a,5,6,8,8a-hexahydropyrano[3,4-d][1,3]thiazin-2-amine (15)

Conversion of C71 to the product was carried out using the method described for synthesis of 8 in Example 8. The product was obtained as a white solid. Yield: 17 mg, 42 μmol, 93%. LCMS m/z 410.3 [M+H$^+$]. $^1$H NMR (400 MHz, CDCl$_3$) δ 7.25-7.31 (m, 2H), 6.99-7.06 (m, 1H), 4.51 (ddd, J=47.6, 9.7, 6.1 Hz, 1H), 4.42 (ddd, J=47.0, 9.7, 3.8 Hz, 1H), 4.15 (dd, J=11.3, 1.9 Hz, 1H), 3.91-4.02 (m, 1H), 3.86-3.91 (m, 3H), 3.17 (q, J$_{HF}$=9.4 Hz, 2H), 2.96-3.07 (m, 2H), 2.60-2.67 (m, 1H), 1.80-1.92 (m, 1H), 1.52 (ddd, J=13, 4, 2 Hz, 1H).

Example 16 rel-(4aR,6R,8aS)-8a-(2-Fluoro-5-{[(2,2,2-trifluoroethyl)amino]methyl}phenyl)-6-(1-methyl-1H-pyrazol-4-yl)-4,4a,5,6,8,8a-hexahydropyrano[3,4-d][1,3]thiazin-2-amine (16)

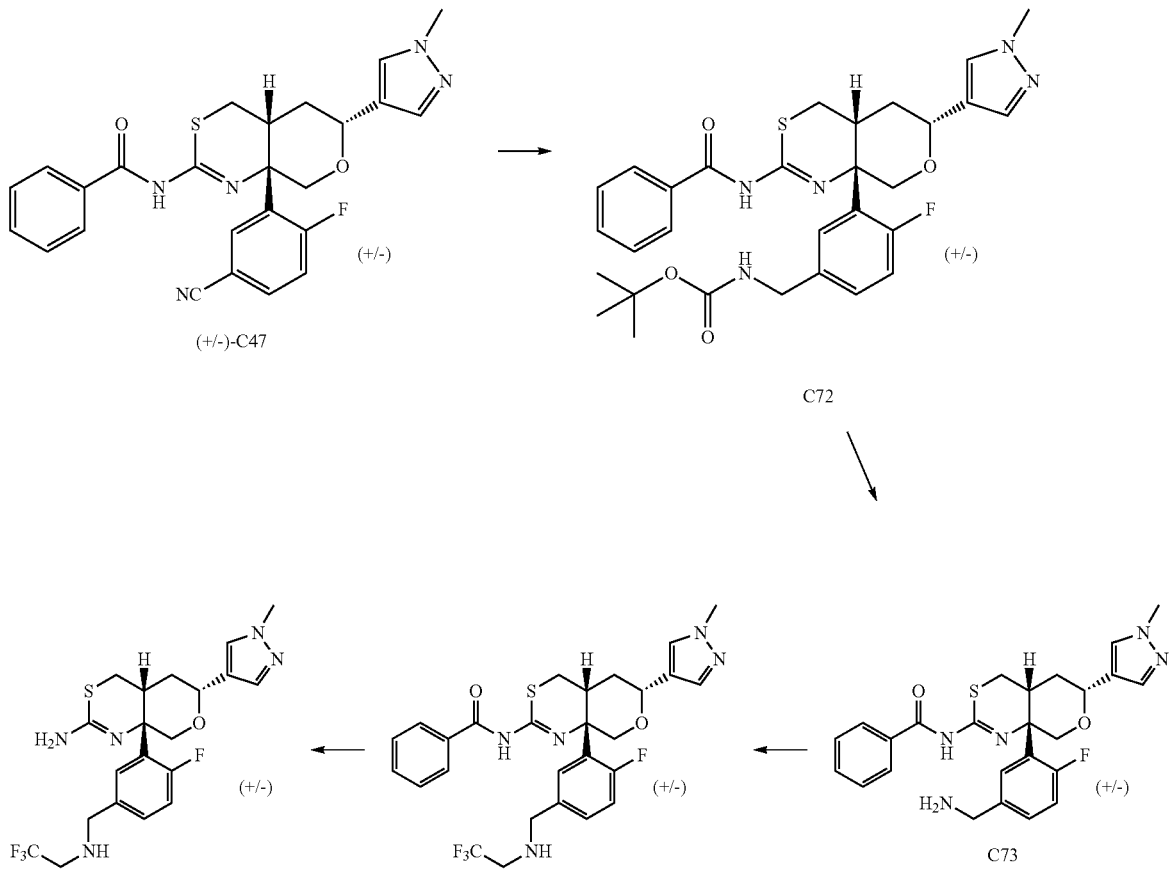

Step 1. Synthesis of tert-butyl {3-[rel-(4aR,6R,8aS)-2-(benzoylamino)-6-(1-methyl-1H-pyrazol-4-yl)-4,4a,5,6-tetrahydropyrano[3,4-d][1,3]thiazin-8a(8H)-yl]-4-fluorobenzyl}carbamate (C72)

N-[rel-(4aR,6R,8aS)-8a-(5-Cyano-2-fluorophenyl)-6-(1-methyl-1H-pyrazol-4-yl)-4,4a,5,6,8,8a-hexahydropyrano[3,4-d][1,3]thiazin-2-yl]benzamide [(+/−)—C47, which may be prepared in the same manner as C47, by using the chemistry described in Preparation 1 followed by Examples 10 and 12, but employing racemic 2-[(benzyloxy)methyl]oxirane as starting material] (440 mg, 0.925 mmol) was converted to the product using the method described for synthesis of C25 in Example 8. In this case, preparative thin layer chromatography (Eluent: 1:2 petroleum ether/ethyl acetate) was carried out, affording the product as a yellow solid. Starting material C47 (110 mg) was also recovered. Yield: 200 mg, 0.345 mmol, 37% (50% based on recovered starting material). $^1$H NMR (400 MHz, CDCl$_3$), characteristic peaks: δ 8.24 (br d, J=8 Hz, 2H), 7.49-7.54 (m, 1H), 7.47 (s, 1H), 7.44 (br dd, J=8, 7 Hz, 2H), 7.41 (s, 1H), 7.10 (dd, J=12.2, 8.5 Hz, 1H), 4.73 (br d, J=11.4 Hz, 1H), 4.22-4.35 (m, 3H), 3.86 (s, 3H), 3.83-3.91 (m, 1H), 3.28-3.36 (m, 1H), 3.06 (dd, J=12.7, 4.1 Hz, 1H), 2.66 (dd, J=12.7, 2.6 Hz, 1H), 2.23-2.35 (m, 1H), 1.89-1.97 (m, 1H), 1.40 (s, 9H).

Step 2. Synthesis of N-[rel-(4aR,6R,8aS)-8a-[5-(aminomethyl)-2-fluorophenyl]-6-(1-methyl-1H-pyrazol-4-yl)-4,4a,5,6,8,8a-hexahydropyrano[3,4-d][1,3]thiazin-2-yl]benzamide (C73)

A solution of C72 (185 mg, 0.319 mmol) in methanolic hydrogen chloride (4 N, 6 mL) was stirred at room temperature for 1.5 hours. The reaction mixture was concentrated in vacuo, and the residue was partitioned between ethyl acetate (100 mL) and saturated aqueous sodium bicarbonate solution (10 mL). The organic layer was washed with saturated aqueous sodium chloride solution (10 mL), dried over sodium sulfate, and concentrated under reduced pressure to provide the product as a brown foam. Yield: 150 mg, 0.313 mmol, 98%.

Step 3. Synthesis of N-[rel-(4aR,6R,8aS)-8a-(2-fluoro-5-{[(2,2,2-trifluoroethyl)amino]methyl}phenyl)-6-(1-methyl-1H-pyrazol-4-yl)-4,4a,5,6,8,8a-hexahydropyrano[3,4-d][1,3]thiazin-2-yl]benzamide (C74)

Compound C73 was converted to the product using the method described for synthesis of C27 in Example 8; in this case, the concentrated reaction mixture was directly subjected to silica gel chromatography (Gradient: 0% to 100% ethyl acetate in petroleum ether), affording the product as a yellow foam. Yield: 95 mg, 0.17 mmol, 60%. LCMS m/z 562.1 [M+H$^+$]. $^1$H NMR (400 MHz, CDCl$_3$) δ 8.21-8.28 (m, 2H), 7.48 (s, 1H), 7.42 (s, 1H), 7.39-7.56 (m, 4H), 7.30-7.36 (m, 1H), 7.12 (dd, J=12.2, 8.4 Hz, 1H), 4.74 (br d, J=11.4 Hz, 1H), 4.33 (d, J=12.2 Hz, 1H), 3.87 (s, 3H), 3.84-3.92 (m, 3H), 3.29-3.37 (m, 1H), 3.16 (q, J$_{HF}$=9.3 Hz, 2H), 3.03-3.09 (m, 1H), 2.68 (br d, J=13 Hz, 1H), 2.24-2.35 (m, 1H), 1.90-1.97 (m, 1H).

Step 4. Synthesis of rel-(4aR,6R,8aS)-8a-(2-fluoro-5-{[(2,2,2-trifluoroethyl)amino]methyl}phenyl)-6-(1-methyl-1H-pyrazol-4-yl)-4,4a,5,6,8,8a-hexahydropyrano[3,4-d][1,3]thiazin-2-amine (16)

Hydrazine monohydrate (76 mg, 1.52 mmol) was added in one portion to a solution of C74 (95 mg, 0.17 mmol) in ethanol (5 mL), and the reaction mixture was allowed to stir at room temperature for 18 hours. After removal of solvent in vacuo, the residue was purified by preparative thin layer chromatography (Eluent: 10:1 dichloromethane/methanol) followed by silica gel chromatography (Eluent: 10% methanol in dichloromethane) to afford the product as a white solid. Yield: 25 mg, 55 μmol, 32%. LCMS m/z 458.0 [M+H$^+$]. $^1$H NMR (400 MHz, CDCl$_3$) δ 7.48 (s, 1H), 7.45 (s, 1H), 7.28-7.34 (m, 2H), 7.05 (dd, J=12, 8 Hz, 1H), 4.70 (br d, J=11.4 Hz, 1H), 4.25 (br dd, J=11.4, 1.4 Hz, 1H), 3.88 (s, 3H), 3.86-3.95 (m, 3H), 3.11-3.23 (m, 3H), 3.01 (dd, J=12.5, 4.0 Hz, 1H), 2.67 (dd, J=12.4, 2.7 Hz, 1H), 2.06-2.17 (m, 1H), 1.78-1.85 (m, 1H).

Example 17

3-[(4R,4aR,6R,8aS)-2-Amino-4-methyl-6-(3-methyl-1,2-oxazol-5-yl)-4,4a,5,6-tetrahydropyrano[3,4-d][1,3]thiazin-8a(8H)-yl]-4-fluorobenzonitrile (17)

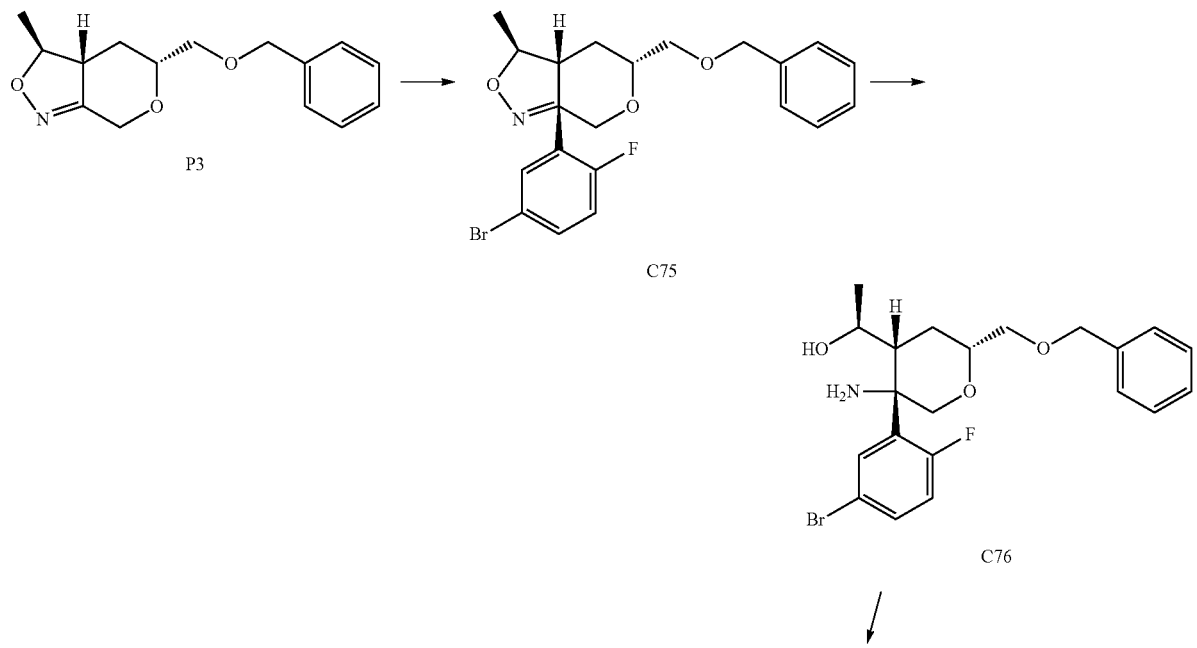

-continued

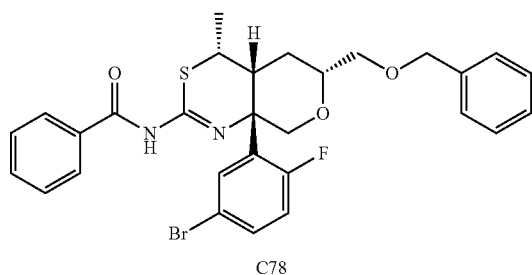
C78

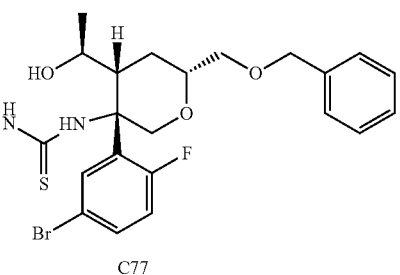
C77

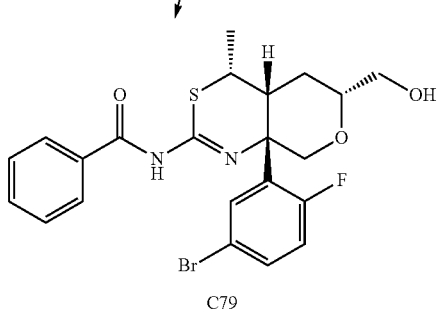
C79

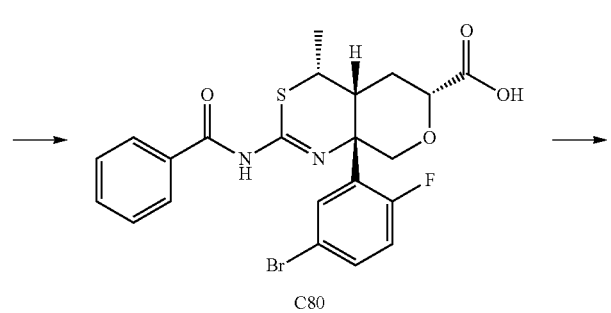
C80

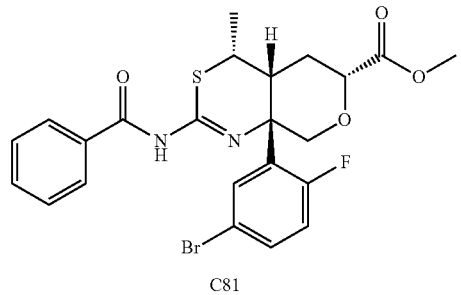
C81

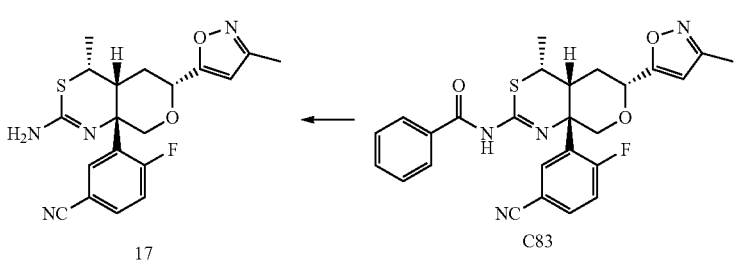
17      C83

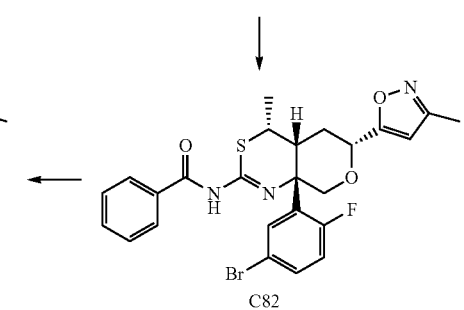
C82

Step 1. Synthesis of (3S,3aR,5R,7aS)-5-[(benzyloxy)methyl]-7a-(5-bromo-2-fluorophenyl)-3-methyl-hexahydro-1H-pyrano[3,4-c][1,2]oxazole (C75)

Boron trifluoride-diethyl etherate (10.3 mL, 83.5 mmol) was added to a −78° C. solution of P3 (10.0 g, 38.3 mmol) in toluene (383 mL) and stirring was continued at −78° C. for 30 minutes. Subsequent addition of 4-bromo-1-fluoro-2-iodobenzene (11.6 g, 38.6 mmol) was followed by slow introduction of n-butyllithium (2.5 M in hexanes, 15.5 mL, 38.8 mmol), at a rate such that the internal reaction temperature did not exceed −73° C. After the reaction mixture had stirred at −78° C. for 90 minutes, saturated aqueous ammonium chloride solution (200 mL) was added; the resulting mixture was allowed to warm to room temperature, whereupon it was partitioned between ethyl acetate (400 mL) and water (800 mL). The aqueous layer was extracted with ethyl acetate (3×200 mL), and the combined organic layers were washed with saturated aqueous sodium chloride solution (200 mL), dried over sodium sulfate, filtered, and concentrated in vacuo. Silica gel chromatography (Gradient: 10% to 70% ethyl acetate in heptane) provided the product as a colorless oily residue. Yield: 6.14 g, 14.1 mmol, 37%. LCMS m/z 436.2, 438.2 [M+H$^+$]. $^1$H NMR (400 MHz, CD$_3$OD) δ 8.06 (dd, J=7.0, 2.7 Hz, 1H), 7.46 (ddd, J=8.7, 4.3, 2.7 Hz, 1H), 7.26-7.38 (m, 5H), 7.06 (dd, J=11.6, 8.7 Hz, 1H), 4.57 (AB quartet, J$_{AB}$=12.1 Hz, Δν$_{AB}$=1 Hz, 2H), 4.02 (qd, J=6.4, 2.4 Hz, 1H), 3.94 (dd, J=12.8, 2.1 Hz, 1H), 3.77 (dd, J=12.8, 1.5 Hz, 1H), 3.75-3.82 (m, 1H), 3.57 (dd, half of ABX pattern, J=10.4, 5.4 Hz, 1H), 3.54 (dd, half of ABX pattern, J=10.4, 4.4 Hz, 1H), 2.83-2.90 (m, 1H), 2.02 (ddd, J=14.0, 7.7, 2.6 Hz, 1H), 1.57-1.68 (m, 1H), 0.77 (d, J=6.4 Hz, 3H).

Step 2. Synthesis of (1S)-1-[(2R,4R,5S)-5-amino-2-[(benzyloxy)methyl]-5-(5-bromo-2-fluorophenyl) tetrahydro-2H-pyran-4-yl]ethanol (C76)

Samarium iodide (0.1 M solution in tetrahydrofuran, 800 mL, 80 mmol) was added drop-wise to a 0° C. solution of C75 (6.00 g, 13.8 mmol) in tetrahydrofuran (140 mL), and the reaction mixture was allowed to stir at room temperature for 24 hours. A saturated aqueous solution of sodium thiosulfate pentahydrate (500 mL) was added to the reaction mixture, followed by extraction with ethyl acetate (3×250 mL). The combined organic layers were washed with saturated aqueous sodium chloride solution (500 mL), dried over sodium sulfate, filtered, and concentrated in vacuo, affording the product as a yellow oily residue. This was used directly in the next step. Yield: 6.00 g, 13.7 mmol, 99%. LCMS m/z 438.2, 440.2 [M+H$^+$]. $^1$H NMR (400 MHz, CD$_3$OD) δ 7.89 (dd, J=7.1, 2.6 Hz, 1H), 7.40 (ddd, J=8.7, 4.1, 2.6 Hz, 1H), 7.26-7.38 (m, 5H), 6.98 (dd, J=12.4, 8.6 Hz, 1H), 4.58 (s, 2H), 3.97 (dd, J=11.3, 2.0 Hz, 1H), 3.70-3.77 (m, 1H), 3.61 (dd, half of ABX pattern, J=10.3, 5.8 Hz, 1H), 3.57-3.65 (m, 1H), 3.56 (dd, half of ABX pattern, J=10.3, 4.0 Hz, 1H), 3.39 (d, J=11.3 Hz, 1H), 2.56-2.63 (m, 1H), 1.58-1.70 (m, 2H), 0.99 (d, J=6.5 Hz, 3H).

Step 3. Synthesis of N-{[(3S,4R,6R)-6-[(benzyloxy)methyl]-3-(5-bromo-2-fluorophenyl)-4-[(1S)-1-hydroxyethyl]tetrahydro-2H-pyran-3-yl]carbamothioyl}benzamide (C77)

Compound C76 (from the previous step, 6.00 g, 13.7 mmol) was converted to the product using the method described for synthesis of C8 in Example 1. A portion of the resulting orange solid (8.22 g, 513.7 mmol) was taken on to the following step.

Step 4. Synthesis of N-[(4R,4aR,6R,8aS)-6-[(benzyloxy)methyl]-8a-(5-bromo-2-fluorophenyl)-4-methyl-4,4a,5,6,8,8a-hexahydropyrano[3,4-d][1,3]thiazin-2-yl]benzamide (C78)

1-Chloro-N,N,2-trimethylprop-1-en-1-amine (Ghosez's reagent, 4.62 mL, 34.9 mmol) was added in a drop-wise manner to a solution of C77 (from the previous step, 7.00 g, 511.6 mmol) in dichloromethane (225 mL). After the reaction mixture had stirred at room temperature for 1.5 hours, it was partitioned between ethyl acetate (500 mL) and saturated aqueous sodium bicarbonate solution (1 L). The aqueous layer was extracted with ethyl acetate (3×250 mL), and the combined organic layers were washed sequentially with water (2×1 L) and saturated aqueous sodium chloride solution (500 mL), dried over sodium sulfate, filtered, and concentrated in vacuo. The residue was combined with an identical reaction product obtained from the same batch of C77 (0.250 g, 50.416 mmol) and purified via silica gel chromatography (Gradient: 0% to 70% ethyl acetate in heptane), providing the product as a white solid. Yield: 4.80 g, 8.23 mmol, 68% over two steps. LCMS m/z 583.2, 585.2 [M+H$^+$]. $^1$H NMR (400 MHz, CD$_3$OD) δ 8.12 (d, J=7.4 Hz, 2H), 7.49-7.57 (m, 3H), 7.43-7.48 (m, 2H), 7.28-7.33 (m, 2H), 7.17-7.26 (m, 3H), 7.14 (dd, J=12.1, 8.6 Hz, 1H), 4.55 (AB quartet, J$_{AB}$=11.8 Hz, Δv$_{AB}$=22.4 Hz, 2H), 4.13 (br d, J=12 Hz, 1H), 3.91 (d, J=11.8 Hz, 1H), 3.83-3.9 (m, 1H), 3.60 (dd, half of ABX pattern, J=10.7, 5.4 Hz, 1H), 3.57 (dd, half of ABX pattern, J=10.8, 4.1 Hz, 1H), 3.16-3.26 (br m, 1H), 2.97-3.05 (m, 1H), 1.71-1.78 (m, 1H), 1.58-1.69 (m, 1H), 1.23 (d, J=7.0 Hz, 3H).

Step 5. Synthesis of N-[(4R,4aR,6R,8aS)-8a-(5-bromo-2-fluorophenyl)-6-(hydroxymethyl)-4-methyl-4,4a,5,6,8,8a-hexahydropyrano[3,4-d][1,3]thiazin-2-yl]benzamide (C79)

Compound C78 was converted to the product using the method described for synthesis of C33 in Example 10. The product was obtained as a white solid. Yield: 3.98 g, 8.07 mmol, 98%. LCMS m/z 493.2, 495.1 [M+H$^+$]. $^1$H NMR (400 MHz, CD$_3$OD) δ 8.13 (br d, J=7 Hz, 2H), 7.51-7.59 (m, 3H), 7.47 (br dd, J=7.6, 7.3 Hz, 2H), 7.16 (dd, J=12.1, 8.6 Hz, 1H), 4.15 (br d, J=12 Hz, 1H), 3.92 (d, J=11.7 Hz, 1H), 3.70-3.77 (m, 1H), 3.60 (d, J=5.2 Hz, 2H), 3.18-3.27 (br m, 1H), 2.99-3.07 (br m, 1H), 1.74-1.81 (m, 1H), 1.49-1.61 (m, 1H), 1.26 (d, J=6.9 Hz, 3H).

Step 6. Synthesis of (4R,4aR,6R,8aS)-2-(benzoylamino)-8a-(5-bromo-2-fluorophenyl)-4-methyl-4,4a,5,6,8,8a-hexahydropyrano[3,4-d][1,3]thiazine-6-carboxylic acid (C80)

Using the method described for synthesis of C34 in Example 10, C79 (3.98 g, 8.07 mmol) was converted to the product, which was obtained as a purple solid (3.73 g). This material exhibited aromatic impurities in the $^1$H NMR, but was carried directly to the following step. LCMS m/z 507.1, 509.1 [M+H$^+$]. $^1$H NMR (400 MHz, CD$_3$OD), characteristic peaks: δ 8.06-8.11 (m, 2H), 7.50-7.56 (m, 2H), 4.37 (dd, J=12.0, 2.5 Hz, 1H), 4.14 (br AB quartet, J$_{AB}$=12.1 Hz, Δv$_{AB}$=57.5 Hz, 2H), 3.3-3.41 (br m, 1H), 3.15-3.23 (m, 1H), 2.17-2.24 (m, 1H), 1.70-1.81 (m, 1H), 1.33 (d, J=7.0 Hz, 3H).

Step 7. Synthesis of methyl (4R,4aR,6R,8aS)-2-(benzoylamino)-8a-(5-bromo-2-fluorophenyl)-4-methyl-4,4a,5,6,8,8a-hexahydropyrano[3,4-d][1,3]thiazine-6-carboxylate (C81)

Compound C80 (from the previous step, 3.73 g, <7.35 mmol) was converted to the product using the method described for synthesis of C35 in Example 10. The product, obtained as a yellow solid (3.50 g), contained aromatic impurities as assessed by $^1$H NMR, and was taken directly to the following step. LCMS m/z 521.1, 523.1 [M+H$^+$]. $^1$H NMR (400 MHz, CD$_3$OD), characteristic peaks: δ 8.05-8.09 (m, 2H), 7.69-7.74 (m, 1H), 7.57-7.62 (m, 2H), 4.47 (dd, J=12, 3 Hz, 1H), 4.21 (br AB quartet, J$_{AB}$=12.5 Hz, Δv$_{AB}$=25 Hz, 2H), 3.78 (s, 3H), 3.51-3.61 (br m, 1H), 2.21-2.27 (m, 1H), 1.72-1.83 (m, 1H), 1.41 (d, J=7.0 Hz, 3H).

Step 8. Synthesis of N-[(4R,4aR,6R,8aS)-8a-(5-bromo-2-fluorophenyl)-4-methyl-6-(3-methyl-1,2-oxazol-5-yl)-4,4a,5,6,8,8a-hexahydropyrano[3,4-d][1,3]thiazin-2-yl]benzamide (C82)

Compound C81 (from the previous step, 3.50 g, <6.71 mmol) was converted to the product using the chemistry described for synthesis of C36 in Example 10. The product was isolated as a white solid. Yield: 2.30 g, 4.22 mmol, 52% over 3 steps. LCMS m/z 544.2, 546.1 [M+H$^+$]. $^1$H NMR (400 MHz, CD$_3$OD) δ 8.06-8.16 (m, 2H), 7.53-7.60 (m, 3H), 7.48 (br dd, J=7.6, 7.4 Hz, 2H), 7.17 (dd, J=12.1, 8.6 Hz, 1H), 6.30 (s, 1H), 4.94 (br dd, J=12, 2 Hz, 1H), 4.32 (br d, J=11.7 Hz, 1H), 4.02 (d, J=11.7 Hz, 1H), 3.12-3.29 (br m, 2H), 2.26 (s, 3H), 2.13 (br d, J=13 Hz, 1H), 1.86-1.98 (m, 1H), 1.28 (d, J=6.9 Hz, 3H).

Step 9. Synthesis of N-[(4R,4aR,6R,8aS)-8a-(5-cyano-2-fluorophenyl)-4-methyl-6-(3-methyl-1,2-oxazol-5-yl)-4,4a,5,6,8,8a-hexahydropyrano[3,4-d][1,3]thiazin-2-yl]benzamide (C83)

Using the method described for synthesis of C37 in Example 10, C82 was converted to the product, which was obtained as an off-white solid. Yield: 18 mg, 37 μmol, 37%. LCMS m/z 491.1 [M+H$^+$]. $^1$H NMR (400 MHz, CD$_3$OD) δ 8.08 (br d, J=7 Hz, 2H), 7.80-7.87 (m, 2H), 7.54-7.60 (m, 1H), 7.49 (br dd, J=7.7, 7.2 Hz, 2H), 7.41 (dd, J=12.1, 8.8 Hz, 1H), 6.29-6.30 (m, 1H), 4.94 (dd, J=11.7, 2.4 Hz, 1H), 4.31 (dd, J=11.6, 1.6 Hz, 1H), 4.03 (d, J=11.6 Hz, 1H), 3.12-3.24 (br m, 2H), 2.26 (br s, 3H), 2.10-2.17 (m, 1H), 1.86-1.98 (m, 1H), 1.28 (d, J=6.8 Hz, 3H).

Step 10. Synthesis of 3-[(4R,4aR,6R,8aS)-2-amino-4-methyl-6-(3-methyl-1,2-oxazol-5-yl)-4,4a,5,6-tetrahydropyrano[3,4-d][1,3]thiazin-8a(8H)-yl]-4-fluorobenzonitrile (17)

Compound C83 was converted to the product using the method described for synthesis of 12 in Example 12. In this case, silica gel chromatographic purification was carried out using a gradient of 0% to 100% ethyl acetate in heptane. The product was isolated as a white solid. Yield: 24.3 mg, 62.9 μmol, 69%. LCMS m/z 387.1 [M+H$^+$]. $^1$H NMR (400 MHz, CD$_3$OD) δ 7.78 (ddd, J=8.5, 4.4, 2.2 Hz, 1H), 7.67 (dd, J=7.2, 2.1 Hz, 1H), 7.36 (dd, J=12.1, 8.5 Hz, 1H), 6.26 (br s, 1H), 4.88 (dd, J=11.8, 2.5 Hz, 1H, assumed; partially obscured by water peak), 4.28 (dd, J=11.2, 2.1 Hz, 1H), 3.84 (d, J=11.2 Hz, 1H), 3.08-3.14 (m, 1H), 2.94-3.00 (m, 1H), 2.28 (br s, 3H), 1.96-2.03 (m, 1H), 1.77-1.88 (m, 1H), 1.22 (d, J=6.9 Hz, 3H).

Example 18

(4aR*,6R*,8aS*)-8a-[2-Fluoro-5-({[(2R)-1-methoxypropan-2-yl]amino}methyl)phenyl]-6-(1-methyl-1H-pyrazol-4-yl)-4,4a,5,6,8,8a-hexahydropyrano[3,4-d][1,3]thiazin-2-amine (18)

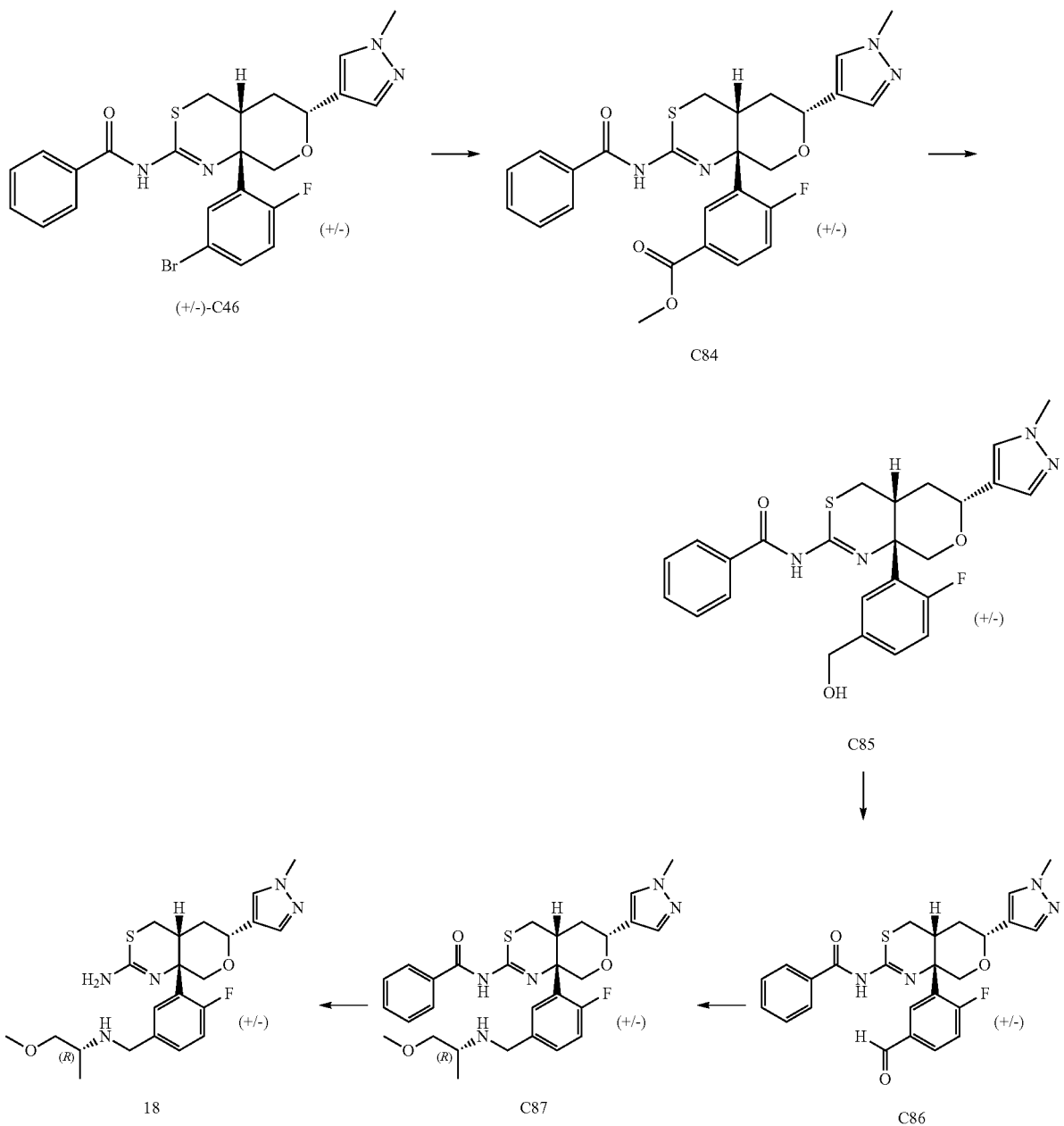

Step 1. Synthesis of methyl 3-[rel-(4aR,6R,8aS)-2-(benzoylamino)-6-(1-methyl-1H-pyrazol-4-yl)-4,4a,5,6-tetrahydropyrano[3,4-d][1,3]thiazin-8a(8H)-yl]-4-fluorobenzoate (C84)

To a mixture of N-[rel-(4aR,6R,8aS)-8a-(5-bromo-2-fluorophenyl)-6-(1-methyl-1H-pyrazol-4-yl)-4,4a,5,6,8,8a-hexahydropyrano[3,4-d][1,3]thiazin-2-yl]benzamide [(+/−)-C46, which may be prepared in the same manner as C46, by using the chemistry described in Preparation 1 followed by Examples 10 and 12, but employing racemic 2-[(benzyloxy)methyl]oxirane as starting material] (1.0 g, 1.9 mmol) and triethylamine (580 mg, 5.73 mmol) in methanol (20 mL) and 1-methylpyrrolidin-2-one (10 mL) was added [1,1'-bis(diphenylphosphino)ferrocene]dichloropalladium(II) (140 mg, 0.19 mmol) in one portion at room temperature. The reaction mixture was stirred under carbon monoxide (2.5 MPa) at 120° C. for 18 hours, whereupon it was concentrated in vacuo to remove methanol, and partitioned between water (500 mL) and ethyl acetate (500 mL). The organic layer was washed with saturated aqueous sodium chloride solution (2×400 mL), dried over sodium sulfate, filtered, and concentrated under reduced pressure. Silica gel chromatography (Eluent: ethyl acetate) afforded the product as a red solid. Yield: 570 mg, 1.12 mmol, 59%. LCMS m/z 509.1 [M+H$^+$].

Step 2. Synthesis of N-[rel-(4aR,6R,8aS)-8a-[2-fluoro-5-(hydroxymethyl)phenyl]-6-(1-methyl-1H-pyrazol-4-yl)-4,4a,5,6,8,8a-hexahydropyrano[3,4-d][1,3]thiazin-2-yl]benzamide (C85)

Lithium aluminum hydride (213 mg, 5.61 mmol) was added in one portion to a 0° C. solution of C84 (570 mg, 1.12 mmol) in tetrahydrofuran (50 mL), and the reaction mixture was stirred at room temperature for 1 hour. It was then cooled to 0° C., quenched with acetic acid (5 mL), and partitioned between ethyl acetate (20 mL) and water (20 mL). The organic layer was washed with saturated aqueous sodium chloride solution (50 mL), dried over sodium sulfate, filtered, and concentrated in vacuo to provide the product (560 mg) as a red foam, which was used directly in the next step. LCMS m/z 481.1 [M+H$^+$].

Step 3. Synthesis of N-[rel-(4aR,6R,8aS)-8a-(2-fluoro-5-formylphenyl)-6-(1-methyl-1H-pyrazol-4-yl)-4,4a,5,6,8,8a-hexahydropyrano[3,4-d][1,3]thiazin-2-yl]benzamide (C86)

A solution of C85 (560 mg from the previous step, 51.12 mmol) and pyridinium chlorochromate (484 mg, 2.24 mmol) in dichloromethane (100 mL) was stirred at room temperature for 18 hours. After concentration of the reaction mixture in vacuo, purification via chromatography on silica gel afforded the product as a dark solid. Yield: 400 mg, 0.836 mmol, 75% over two steps. $^1$H NMR (400 MHz, CDCl$_3$), characteristic peaks: δ 9.97 (s, 1H), 8.21 (br d, J=7 Hz, 2H), 4.75 (br d, J=11.3 Hz, 1H), 4.32 (br d, J=11.5 Hz, 1H), 3.87 (s, 3H), 3.27-3.37 (m, 1H), 2.72 (br d, J=12.3 Hz, 1H).

Step 4. Synthesis of N-[(4aR*,6R*,8aS*)-8a-[2-fluoro-5-({[(2R)-1-methoxypropan-2-yl]amino}methyl)phenyl]-6-(1-methyl-1H-pyrazol-4-yl)-4,4a,5,6,8,8a-hexahydropyrano[3,4-d][1,3]thiazin-2-yl]benzamide (C87)

Sodium acetate (237 mg, 2.89 mmol) and (2R)-1-methoxypropan-2-amine hydrochloride (121 mg, 0.963 mmol) were added to a solution of C86 (228 mg, 0.476 mmol) in anhydrous ethanol (50 mL), and the reaction mixture was stirred at reflux for 2 hours. Solvent was then removed in vacuo and the residue was dissolved in anhydrous methanol (100 mL), treated with sodium borohydride (36.5 mg, 0.965 mmol) in one portion, and stirred at reflux for 1 hour. The reaction mixture was concentrated under reduced pressure; purification by preparative thin layer chromatography (Eluent: 4:1 dichloromethane/methanol) provided the product as a gray solid Yield: 180 mg, 0.326 mmol, 68%.

Step 5. Synthesis of (4aR*,6R*,8aS*)-8a-[2-fluoro-5-({[(2R)-1-methoxypropan-2-yl]amino}methyl)phenyl]-6-(1-methyl-1H-pyrazol-4-yl)-4,4a,5,6,8,8a-hexahydropyrano[3,4-d][1,3]thiazin-2-amine (18)

Compound C87 was converted to the product according to the method described for synthesis of 13 in Example 13. In this case, reversed phase HPLC (Column: Phenomenex Gemini C18, 8 μm; Mobile phase A: aqueous ammonia, pH 10; Mobile phase B: acetonitrile; Gradient: 30% to 50% B) afforded the product as a white gum. By $^1$H NMR analysis, this was judged to consist of a mixture of the expected diastereomers. Yield: 37 mg, 83 μmol, 25%. LCMS m/z 448.3 [M+H$^+$]. $^1$H NMR (400 MHz, DMSO-d$_6$), characteristic peaks: δ 7.60 (s, 1H), 7.33 (s, 1H), 7.24-7.32 (m, 2H), 7.12 (dd, J=12, 8 Hz, 1H), 6.14 (br s, 2H), 4.55 (d, J=11.0 Hz, 1H), 4.46 (br s, 1H), 4.06 (d, J=11 Hz, 1H), 3.79 (s, 3H), 3.58-3.75 (m, 3H), 3.21 and 3.22 (2 s, total 3H), 2.80-2.88 (m, 1H), 2.63-2.79 (m, 3H), 1.85-1.98 (m, 1H), 1.71-1.80 (m, 1H), 0.96 (d, J=6.3 Hz, 3H).

Example 19

(4S,4aR,6S,8aS)-4-(Fluoromethyl)-8a-(2-fluoro-5-{[(2,2,2-trifluoroethyl)amino]methyl}phenyl)-6-methyl-4,4a,5,6,8,8a-hexahydropyrano[3,4-d][1,3]thiazin-2-amine (19)

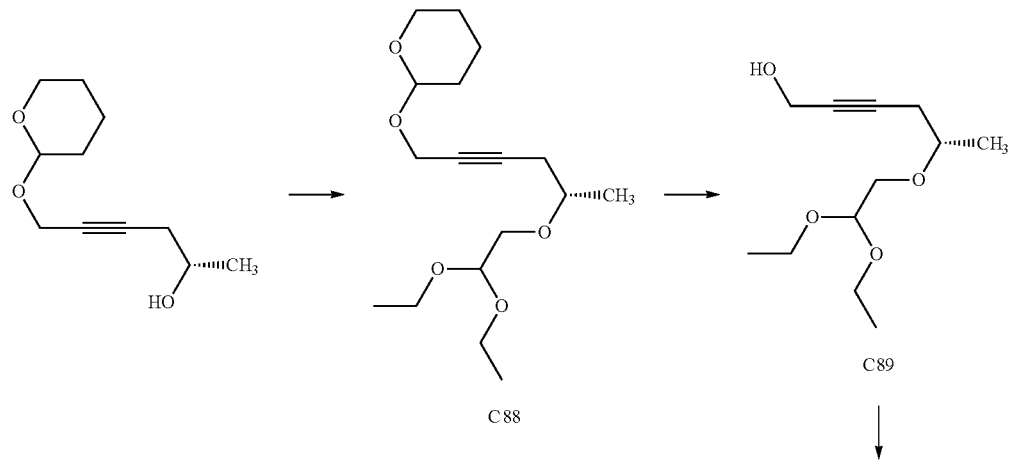

-continued
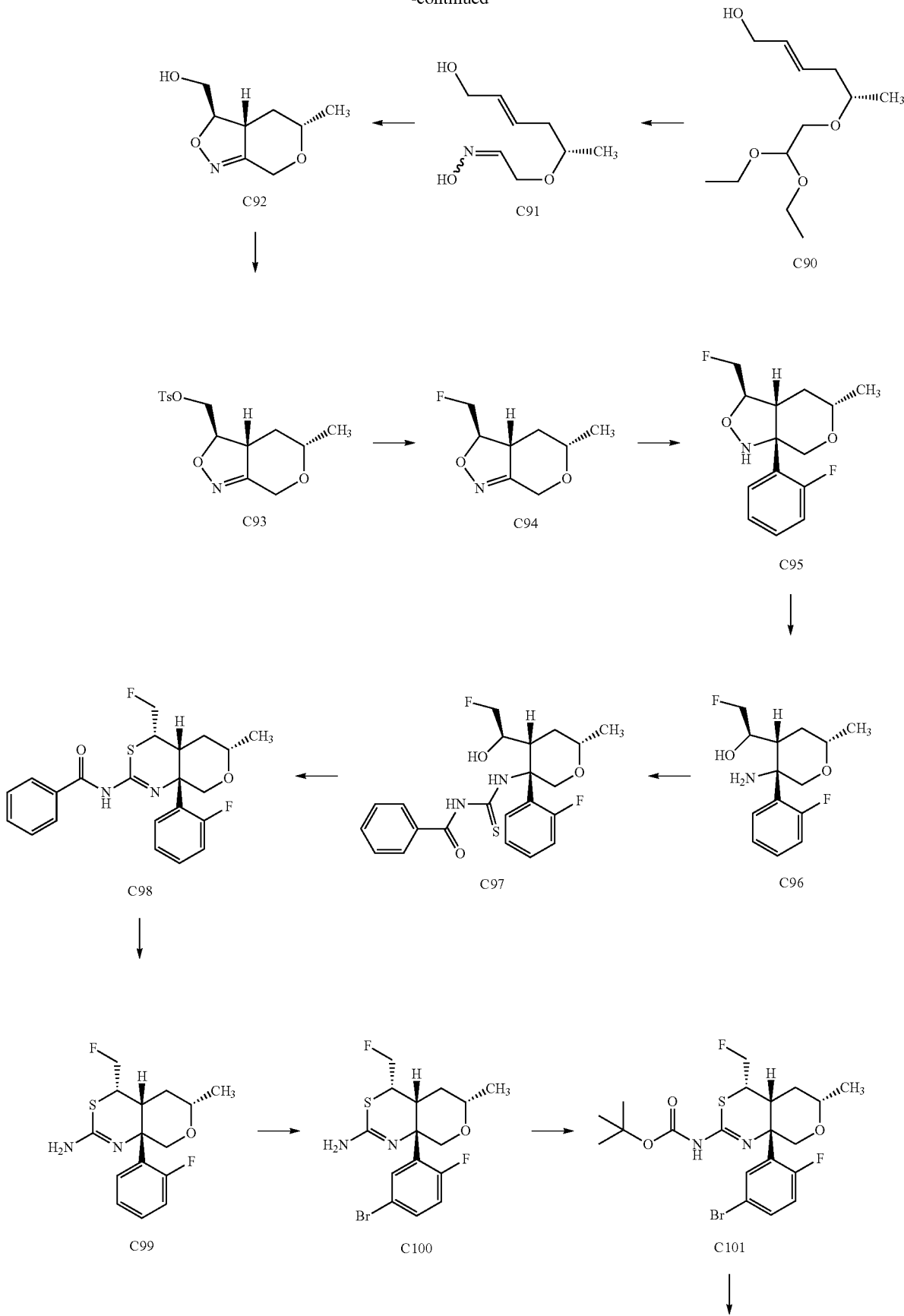

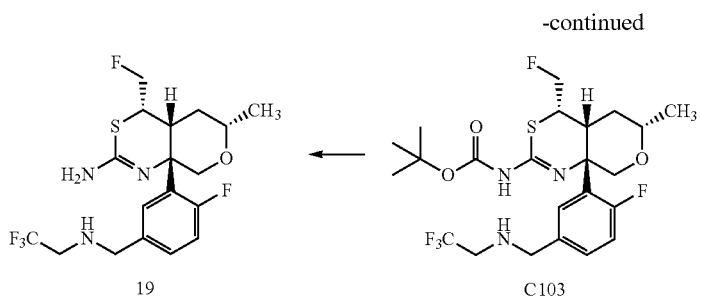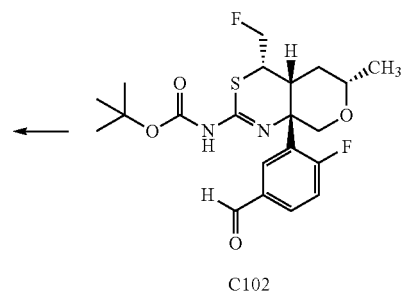

Step 1. Synthesis of 2-{[(5S)-5-(2,2-diethoxyethoxy) hex-2-yn-1-yl]oxy}tetrahydro-2H-pyran (C88)

Sodium hydride (60% in mineral oil, 9.8 g, 240 mmol) was added portion-wise to a 0° C. solution of (2S)-6-(tetrahydro-2H-pyran-2-yloxy)hex-4-yn-2-ol (synthesized as described by G. V. M. Sharma and K. Veera Babu, *Tetrahedron: Asymmetry* 2007, 18, 2175-2184) (27.0 g, 136 mmol) in tetrahydrofuran (130 mL), at a rate such that the reaction temperature remained below 5° C. After 5 minutes, the cooling bath was removed and the reaction mixture was allowed to stir at room temperature for 3.5 hours, whereupon it was again cooled to 0° C. A solution of 1,1-diethoxy-2-iodoethane (49.9 g, 204 mmol) in tetrahydrofuran (5 mL) was added drop-wise over 30 minutes, at a rate that maintained the reaction temperature below 10° C. After removal of the cooling bath, the reaction mixture was stirred at room temperature for 30 minutes, and then placed in a 50° C. oil bath for 90 minutes, at which time additional 1,1-diethoxy-2-iodoethane (3.3 g, 14 mmol) was added, as a solution in tetrahydrofuran (5 mL). Heating was continued for 1 hour, at which time the reaction mixture was cooled in an ice bath and quenched with a mixture of saturated aqueous ammonium chloride solution (210 mL) and saturated aqueous sodium chloride solution (210 mL). The resulting mixture was extracted with tert-butyl methyl ether (3×200 mL), and the combined organic layers were washed with saturated aqueous sodium chloride solution, dried over sodium sulfate, filtered, and concentrated in vacuo. Silica gel chromatography (Gradient: 0% to 50% ethyl acetate in hexanes) afforded the product as a yellow oil. Yield: 22.8 g, 72.5 mmol, 53%. $^1$H NMR (500 MHz, CDCl$_3$), characteristic peaks: δ 4.80 (t, J=3.5 Hz, 1H), 4.59 (t, J=5.2 Hz, 1H), 4.28 (dt, half of ABX$_2$ pattern, J=15.3, 2.1 Hz, 1H), 4.20 (dt, half of ABX$_2$ pattern, J=15.3, 2.1 Hz, 1H), 3.81-3.87 (m, 1H), 2.48-2.56 (m, 1H), 2.28-2.36 (m, 1H), 1.78-1.88 (m, 1H), 1.69-1.77 (m, 1H), 1.25 (d, J=6.1 Hz, 3H), 1.22 (t, J=7.1 Hz, 6H).

Step 2. Synthesis of (5S)-5-(2,2-diethoxyethoxy)hex-2-yn-1-ol (C89)

Benzenesulfonic acid (1.62 g, 10.2 mmol) was added in one portion to a 0° C. solution of C88 (32.2 g, 102 mmol) in absolute ethanol (250 mL). The reaction mixture was stirred under ice cooling for 2 hours, then at room temperature for 18 hours, whereupon it was poured into stirring saturated aqueous sodium bicarbonate solution (400 mL). Saturated aqueous sodium chloride solution (200 mL) was added, the aqueous layer was saturated via addition of solid sodium chloride, and the mixture was extracted with tert-butyl methyl ether (400 mL, then 3×200 mL). The combined organic layers were washed with saturated aqueous sodium chloride solution, dried over sodium sulfate, filtered, and concentrated in vacuo, providing the product as a yellow oil. Yield: 23.2 g, 101 mmol, 99%. $^1$H NMR (500 MHz, CDCl$_3$) δ 4.61 (t, J=5.2 Hz, 1H), 4.24 (dt, J=5.8, 2.2 Hz, 2H), 3.49-3.74 (m, 7H), 2.45-2.53 (m, 1H), 2.34 (ddt, J=16.6, 6.9, 2.2 Hz, 1H), 1.67 (t, J=6.0 Hz, 1H), 1.25 (d, J=6.2 Hz, 3H), 1.22 (t, J=7.0 Hz, 6H).

Step 3. Synthesis of (2E,5S)-5-(2,2-diethoxyethoxy) hex-2-en-1-ol (C90)

A solution of C89 (36.8 g, 160 mmol) in tetrahydrofuran (360 mL) was cooled in an ice bath. A solution of lithium aluminum hydride in tetrahydrofuran (1.0 M, 288 mL, 288 mmol) was added drop-wise over 35 minutes, at a rate that kept the internal reaction temperature below 7° C. The cooling bath was removed, and the reaction mixture was allowed to warm to room temperature and stir for 4 hours, whereupon it was cooled in an ice bath and treated sequentially with water (68 mL), 6 M aqueous sodium hydroxide solution (34 mL), and water (55 mL). tert-Butyl methyl ether (600 mL) was added, and the mixture was stirred for 20 minutes and filtered through diatomaceous earth; the filter pad was rinsed three times with tert-butyl methyl ether. The combined filtrates were concentrated in vacuo and purified by silica gel chromatography (Gradient: 0% to 50% ethyl acetate in hexanes) to provide the product as a light yellow oil. Yield: 29.0 g, 125 mmol, 78%. $^1$H NMR (500 MHz, CDCl$_3$) δ 5.63-5.79 (m, 2H), 4.59 (t, J=5.3 Hz, 1H), 4.06-4.13 (m, 2H), 3.66-3.73 (m, 2H), 3.49-3.61 (m, 4H), 3.44 (dd, half of ABX pattern, J=10.4, 5.4 Hz, 1H), 2.27-2.34 (m, 1H), 2.15-2.22 (m, 1H), 1.34 (t, J=5.8 Hz, 1H), 1.22 (t, J=7.1 Hz, 6H), 1.15 (d, J=6.2 Hz, 3H).

Step 4. Synthesis of (2E,5S)-5-{[(2Z)-2-(hydroxyimino)ethyl]oxy}hex-2-en-1-ol (C91)

Hydroxylamine hydrochloride (12.5 g, 180 mmol) was added to a solution of C90 (29.0 g, 125 mmol) in ethanol (360 mL) and water (72 mL), and the reaction mixture was placed in a 70° C. oil bath for 3.5 hours. After the reaction mixture had cooled to room temperature, sodium acetate (20.5 g, 250 mmol) was added, and stirring was continued for 20 minutes. Solvent was removed in vacuo, and the aqueous residue was saturated via addition of solid sodium chloride, then extracted six times with dichloromethane. The combined organic layers were dried over sodium sulfate, filtered, and concentrated in vacuo, providing the product as a yellow oil. This material was assigned as a mixture of geometric isomers around the oxime, from examination of its $^1$H NMR spectrum. Yield: 18.1 g, 104 mmol, 83%. $^1$H NMR (500 MHz, CDCl$_3$) δ [7.48 (t, J=5.6 Hz) and 6.84-6.95 (m), total 1H], 5.59-5.82 (m, 2H), 4.25-4.41 (m, 1H), 4.03-4.17 (m, 3H), 3.47-3.60 (m, 1H), 2.27-2.36 (m, 1H), 2.17-2.27 (m, 1H), [1.18 (d, J=6.0 Hz) and 1.17 (d, J=6.1 Hz), total 3H].

Step 5. Synthesis of [(3R,3aR,5S)-5-methyl-3,3a,4,5-tetrahydro-7H-pyrano[3,4-c][1,2]oxazol-3-yl]methanol (C92)

Saturated aqueous sodium chloride solution (50 mL) was added to a solution of C91 (18.5 g, 107 mmol) in dichloromethane (520 mL). The pH of the aqueous layer was adjusted to 9 through drop-wise addition of aqueous 6 M sodium hydroxide solution, and an aqueous solution of sodium hypochlorite (6%, 140 mL, 113 mmol) was then added drop-wise over 40 minutes; after 1.5 hours, the pH was again adjusted to 9, and additional sodium hypochlorite (6%, 140 mL, 113 mmol) was added drop-wise over 20 minutes. After 1 hour, the aqueous layer was saturated with solid sodium chloride and extracted with dichloromethane (6×125 mL), and the combined organic layers were dried over sodium sulfate, filtered, concentrated in vacuo, and purified via silica gel chromatography (Gradient: 0% to 65% ethyl acetate in hexanes). The product was isolated as a light yellow oil. Yield: 14.0 g, 81.8 mmol, 76%. $^1$H NMR (500 MHz, CDCl$_3$) δ 4.63 (d, J=13.4 Hz, 1H), 4.24 (ddd, J=10.3, 3.2, 3.2 Hz, 1H), 4.17 (dd, J=13.4, 1.2 Hz, 1H), 3.99 (ddd, J=12.4, 4.7, 3.0 Hz, 1H), 3.71 (ddd, J=12.4, 8.7, 3.5 Hz, 1H), 3.58-3.66 (m, 1H), 3.37-3.45 (m, 1H), 2.10 (ddd, J=12.8, 6.6, 1.6 Hz, 1H), 1.80 (dd, J=8.6, 4.7 Hz, 1H), 1.48-1.56 (m, 1H), 1.26 (d, J=6.2 Hz, 3H).

Step 6. Synthesis of [(3R,3aR,5S)-5-methyl-3,3a,4,5-tetrahydro-7H-pyrano[3,4-c][1,2]oxazol-3-yl]methyl 4-methylbenzenesulfonate (C93)

A solution of C92 (11.9 g, 69.5 mmol) in pyridine (25 mL) was added drop-wise over 15 minutes to a 0° C. solution of p-toluenesulfonyl chloride (21.2 g, 111 mmol) in pyridine (35 mL), and the reaction mixture was allowed to stir for 18 hours while the cooling bath warmed to room temperature. Solvent was removed in vacuo, and the residue was diluted with water (200 mL) and extracted with ethyl acetate (4×120 mL). The combined organic layers were washed sequentially with aqueous hydrochloric acid (1 M, 180 mL), saturated aqueous sodium bicarbonate solution (180 mL), and water (2×100 mL), dried over sodium sulfate, filtered, and concentrated under reduced pressure. The resulting solid was triturated with tert-butyl methyl ether and washed twice with tert-butyl methyl ether to afford the product as an off-white solid. Yield: 17.4 g, 53.5 mmol, 77%. $^1$H NMR (500 MHz, CDCl$_3$) δ 7.80 (br d, J=8 Hz, 2H), 7.37 (d, J=8.0 Hz, 2H), 4.60 (d, J=13.3 Hz, 1H), 4.22-4.33 (m, 2H), 4.18 (dd, J=10.6, 5.3 Hz, 1H), 4.14 (dd, J=13.3, 1.1 Hz, 1H), 3.56-3.64 (m, 1H), 3.27-3.36 (m, 1H), 2.46 (s, 3H), 2.11-2.17 (m, 1H), 1.45-1.53 (m, 1H), 1.25 (d, J=6.2 Hz, 3H).

Step 7. Synthesis of (3R,3aR,5S)-3-(fluoromethyl)-5-methyl-3,3a,4,5-tetrahydro-7H-pyrano[3,4-c][1,2]oxazole (C94)

Compound C93 (24.1 g, 74.1 mmol) was dissolved in a solution of tetrabutylammonium fluoride in tetrahydrofuran (1.0 M, 148 mL, 148 mmol), and the reaction mixture was heated at 80° C. for 22 hours. After cooling to room temperature, the reaction mixture was concentrated in vacuo and purified via silica gel chromatography (Gradient: 0% to 35% ethyl acetate in hexanes), providing the product as a light yellow oil. Yield: 9.93 g, 57.3 mmol, 77%. $^1$H NMR (500 MHz, CDCl$_3$) δ 4.65 (ddd, J=47.4, 10.3, 3.9 Hz, 1H), 4.65 (d, J=13.4 Hz, 1H), 4.59 (ddd, J=46.6, 10.2, 4.1 Hz, 1H), 4.29-4.39 (m, 1H), 4.18 (dd, J=13.3, 1.2 Hz, 1H), 3.59-3.68 (m, 1H), 3.30-3.41 (m, 1H), 2.14 (ddd, J=12.8, 6.5, 1.6 Hz, 1H), 1.50-1.60 (m, 1H), 1.27 (d, J=6.2 Hz, 3H).

Step 8. Synthesis of (3R,3aR,5S,7aS)-3-(fluoromethyl)-7a-(2-fluorophenyl)-5-methylhexahydro-1H-pyrano[3,4-c][1,2]oxazole (C95)

A solution of 1-fluoro-2-iodobenzene (9.9 mL, 85 mmol) in a 10:1 mixture of toluene and tetrahydrofuran was cooled to −73° C. and treated in a drop-wise manner with boron trifluoride-diethyl etherate (10.2 mL, 82.6 mmol), at a rate that kept the internal reaction temperature below −70° C. n-Butyllithium (2.5 M solution in hexanes, 32.3 mL, 80.8 mmol) was then added drop-wise over 45 minutes, while maintaining the internal reaction temperature below −72° C. After 30 minutes, a solution of C94 (7.00 g, 40.4 mmol) in a 10:1 mixture of toluene and tetrahydrofuran (a total of 220 mL of this solvent mixture was used for the reaction) was added drop-wise over 20 minutes, at a rate that kept the internal reaction temperature below −71° C. After the reaction mixture had stirred at −70° C. for 40 minutes, it was poured into saturated aqueous ammonium chloride solution (200 mL), stirred for 20 minutes, and then extracted three times with ethyl acetate. The combined organic layers were washed with saturated aqueous sodium chloride solution, dried over sodium sulfate, filtered, and concentrated in vacuo. Silica gel chromatography (Gradient: 0% to 20% ethyl acetate in hexanes) afforded the product as a viscous yellow oil. Yield: 10.8 g, 40.1 mmol, 99%. $^1$H NMR (500 MHz, CDCl$_3$) δ 7.94 (ddd, J=8.1, 8.0, 1.8 Hz, 1H), 7.27-7.32 (m, 1H), 7.17 (ddd, J=7.7, 7.5, 1.2 Hz, 1H), 7.04 (ddd, J=12.1, 8.2, 1.1 Hz, 1H), 4.09-4.18 (m, 1H), 4.04 (dd, J=12.9, 1.9 Hz, 1H), 3.56-3.85 (m, 4H), 3.13-3.20 (m, 1H), 2.05 (ddd, J=14.2, 7.5, 1.9 Hz, 1H), 1.46-1.57 (m, 1H), 1.27 (d, J=6.2 Hz, 3H).

Step 9. Synthesis of (1R)-1-[(2S,4R,5S)-5-amino-5-(2-fluorophenyl)-2-methyltetrahydro-2H-pyran-4-yl]-2-fluoroethanol (C96)

Zinc dust (34.4 g, 52.6 mmol) was added to a solution of C95 (10.8 g, 40.1 mmol) in acetic acid (150 mL). After 16 hours at room temperature, the reaction mixture was filtered through diatomaceous earth; the filter pad was washed three times with ethyl acetate, and the combined filtrates were adjusted to pH 8 with aqueous sodium bicarbonate solution. The aqueous layer was then extracted three times with ethyl acetate, and the combined organic layers were dried over sodium sulfate, filtered, and concentrated in vacuo to provide the product as a tan syrup (11.0 g), which was taken directly to the following step. $^1$H NMR (500 MHz, CDCl$_3$) δ 7.59 (ddd, J=8.0, 8.0, 1.7 Hz, 1H), 7.30-7.37 (m, 1H), 7.21 (ddd, J=7.6, 7.6, 1.3 Hz, 1H), 7.08 (ddd, J=12.9, 8.2, 1.2 Hz, 1H), 4.16 (dd, J=11.5, 1.6 Hz, 1H), 3.56-3.86 (m, 4H), 3.24 (d, J=11.5 Hz, 1H), 2.70-2.76 (m, 1H), 1.84-1.94 (m, 1H), 1.68 (ddd, J=14.1, 4.5, 2.6 Hz, 1H), 1.32 (d, J=6.1 Hz, 3H).

Step 10. Synthesis of N-{[(3S,4R,6S)-4-[(1R)-2-fluoro-1-hydroxyethyl]-3-(2-fluorophenyl)-6-methyltetrahydro-2H-pyran-3-yl]carbamothioyl}benzamide (C97)

Benzoyl isothiocyanate (7.9 g, 48 mmol) was added to a solution of C96 (from the previous step, 11.0 g, ≤40.1 mmol) in tetrahydrofuran (165 mL), and the reaction mixture was stirred at room temperature for 15 hours. After removal of solvent under reduced pressure, silica gel chromatography (Gradient: 0% to 30% ethyl acetate in hexanes) provided the product as a foamy, light yellow solid (17.5 g), which was taken directly to the following step

Step 11. Synthesis of N-[(4S,4aR,6S,8aS)-4-(fluoromethyl)-8a-(2-fluorophenyl)-6-methyl-4,4a,5,6,8,8a-hexahydropyrano[3,4-d][1,3]thiazin-2-yl]benzamide (C98)

To a solution of C97 (from the previous step, 17.5 g, 540.1 mmol) in 1,2-dichloroethane (250 mL) was added methoxybenzene (13.2 mL, 121 mmol), followed by trifluoromethanesulfonic acid (10.7 mL, 121 mmol). The reaction mixture was heated at 60° C. for 2.5 hours, then cooled to 0°

C. and basified to pH 9 with saturated aqueous sodium carbonate solution. The aqueous layer was extracted three times with dichloromethane, and the combined organic layers were washed with saturated aqueous sodium chloride solution, dried over sodium sulfate, filtered, and concentrated in vacuo. Silica gel chromatography (Gradient: 0% to 35% ethyl acetate in hexanes) provided the product as a white foamy solid. Yield: 11.0 g, 26.4 mmol, 66% over three steps. LCMS m/z 417.2 [M+H]$^+$. $^1$H NMR (500 MHz, CDCl$_3$) δ 12.12 (br s, 1H), 8.24 (br s, 2H), 7.34-7.54 (m, 5H), 7.20 (dd, J=7.6, 7.5 Hz, 1H), 7.12 (dd, J=12.6, 8.2 Hz, 1H), 4.58 (ddd, J=46.8, 9.4, 7.7 Hz, 1H), 4.42 (ddd, J=46.3, 9.5, 6.6 Hz, 1H), 4.22 (d, J=11.9 Hz, 1H), 3.81 (d, J=12.0 Hz, 1H), 3.75-3.85 (m, 1H), 3.47-3.57 (br m, 1H), 3.26-3.35 (br m, 1H), 1.61-1.75 (m, 2H), 1.29 (d, J=6.2 Hz, 3H).

Step 12. Synthesis of (4S,4aR,6S,8aS)-4-(fluoromethyl)-8a-(2-fluorophenyl)-6-methyl-4,4a,5,6,8,8a-hexahydropyrano[3,4-d][1,3]thiazin-2-amine (C99)

To a solution of C98 (10.9 g, 26.2 mmol) in ethanol (470 mL) were added methoxylamine hydrochloride (21.9 g, 262 mmol) and pyridine (21.2 mL, 262 mmol). The reaction mixture was heated at 50° C. for 4 hours, whereupon it was cooled to room temperature and concentrated in vacuo. The residue was dissolved in water and neutralized to pH 7-8 with solid sodium bicarbonate. After removal of water under reduced pressure, the residue was purified via silica gel chromatography (Gradient: 0% to 100% ethyl acetate in hexanes) to provide the product as a white foamy solid. Yield: 6.69 g, 21.4 mmol, 82%. $^1$H NMR (500 MHz, CDCl$_3$) δ 7.34 (ddd, J=8.0, 8.0, 1.8 Hz, 1H), 7.24-7.29 (m, 1H, assumed; partially obscured by solvent peak), 7.13 (ddd, J=7.7, 7.5, 1.2 Hz, 1H), 7.04 (ddd, J=12.8, 8.2, 1.2 Hz, 1H), 4.55 (ddd, J=46.8, 9.4, 6.9 Hz, 1H), 4.35 (ddd, J=46.7, 9.4, 7.0 Hz, 1H), 4.16 (dd, J=11.0, 2.3 Hz, 1H), 3.82 (d, J=11.0 Hz, 1H), 3.70-3.77 (m, 1H), 3.43-3.51 (m, 1H), 3.04 (ddd, J=12.0, 4.0, 3.9 Hz, 1H), 1.41-1.6 (m, 2H, assumed; partially obscured by water peak), 1.27 (d, J=6.2 Hz, 3H).

Step 13. Synthesis of (4S,4aR,6S,8aS)-8a-(5-bromo-2-fluorophenyl)-4-(fluoromethyl)-6-methyl-4,4a,5,6,8,8a-hexahydropyrano[3,4-d][1,3]thiazin-2-amine (C100)

Compound C99 (500 mg, 1.60 mmol) was cooled in an ice bath, then treated with trifluoroacetic acid (3.1 mL) while keeping the internal reaction temperature below 30° C. Sulfuric acid (0.51 mL) was added drop-wise at a rate that maintained the internal reaction temperature below 7° C., and then N-bromosuccinimide (313 mg, 1.76 mmol) was introduced in portions, while keeping the internal temperature below 10° C. The reaction mixture was warmed to room temperature and subsequently placed in an oil bath preheated to 55° C. After 30 minutes, it was cooled to room temperature and poured into a cold aqueous solution of sodium hydroxide [prepared with 1.28 g (32.0 mmol) of sodium hydroxide]. After three extractions of the mixture with ethyl acetate, the combined organic layers were dried over sodium sulfate, filtered, and concentrated in vacuo. The resulting solid was suspended in aqueous sodium hydroxide solution (2 M, 20 mL) and stirred for 4 hours. The solid was collected via filtration and washed three times with water to afford the product as an off-white solid. Yield: 527 mg, 1.35 mmol, 84%. $^1$H NMR (500 MHz, CDCl$_3$), characteristic peaks: δ 7.43 (dd, J=7.0, 2.6 Hz, 1H), 7.37-7.41 (m, 1H), 6.94 (dd, J=11.9, 8.6 Hz, 1H), 4.55 (ddd, J=46.8, 9.4, 7.0 Hz, 1H), 4.36 (ddd, J=46.6, 9.3, 7.0 Hz, 1H), 4.08 (dd, J=11.1, 2.4 Hz, 1H), 3.79-3.86 (m, 1H), 3.67-3.76 (m, 1H), 3.44-3.53 (m, 1H), 3.00-3.08 (m, 1H), 1.27 (d, J=6.2 Hz, 3H).

Step 14. Synthesis of tert-butyl [(4S,4aR,6S,8aS)-8a-(5-bromo-2-fluorophenyl)-4-(fluoromethyl)-6-methyl-4,4a,5,6,8,8a-hexahydropyrano[3,4-d][1,3]thiazin-2-yl]carbamate (C101)

A solution of di-tert-butyl dicarbonate (589 mg, 2.70 mmol) in dichloromethane (2 mL) was added to a solution of C100 (527 mg, 1.35 mmol) in dichloromethane (2 mL), and the reaction mixture was stirred at room temperature for 27 hours. Silica gel chromatography (Gradient: 0% to 35% ethyl acetate in hexanes) provided the product as a white solid. Yield: 624 mg, 1.27 mmol, 94%. $^1$H NMR (500 MHz, CDCl$_3$), characteristic peaks: δ 7.40-7.45 (br m, 1H), 7.32-7.39 (br m, 1H), 6.97 (dd, J=11.9, 8.7 Hz, 1H), 4.53 (ddd, J=47.0, 9.4, 7.9 Hz, 1H), 4.37 (ddd, J=46.2, 9.5, 6.3 Hz, 1H), 4.09 (br d, J=11.6 Hz, 1H), 3.68-3.78 (m, 2H), 3.34-3.43 (br m, 1H), 3.08-3.16 (br m, 1H), 1.53 (s, 9H), 1.28 (d, J=6.1 Hz, 3H).

Step 15. Synthesis of tert-butyl [(4S,4aR,6S,8aS)-8a-(2-fluoro-5-formylphenyl)-4-(fluoromethyl)-6-methyl-4,4a,5,6,8,8a-hexahydropyrano[3,4-d][1,3]thiazin-2-yl]carbamate (C102)

A solution of C101 (390 mg, 0.794 mmol) in diethyl ether (12 mL) was cooled to −78° C. and treated drop-wise with methyllithium (3.0 M solution in 1,2-diethoxymethane, 0.79 mL, 2.37 mmol) over seven minutes. After 35 minutes, sec-butyllithium (1.4 M solution in cyclohexane, 0.62 mL, 0.87 mmol) was added drop-wise over 6 minutes; stirring was then continued at −78° C. for 35 minutes. At this point, N-methyl-N-phenylformamide (0.29 mL, 2.35 mmol) was added drop-wise over 4 minutes. The reaction mixture was stirred at −78° C. for 2.25 hours, and then quenched via addition of saturated aqueous ammonium chloride solution (2.3 mL) and water (7.7 mL). The mixture was extracted four times with ethyl acetate, and the combined organic layers were dried over sodium sulfate, filtered, and concentrated in vacuo. Silica gel chromatography (Gradient: 0% to 30% ethyl acetate in hexanes) provided the product as a white foam. Yield: 272 mg, 0.617 mmol, 78%. $^1$H NMR (500 MHz, CDCl$_3$) δ 9.98 (s, 1H), 7.86-7.92 (m, 1H), 7.81 (br d, J=6.7 Hz, 1H), 7.21-7.28 (m, 1H, assumed; partially obscured by solvent peak), 4.54 (ddd, J=47.0, 9.4, 7.9 Hz, 1H), 4.37 (ddd, J=46.2, 9.5, 6.3 Hz, 1H), 4.10-4.15 (m, 1H), 3.79 (d, J=11.3 Hz, 1H), 3.71-3.78 (m, 1H), 3.31-3.39 (br m, 1H), 3.12-3.19 (br m, 1H), 1.53 (s, 9H), 1.5-1.66 (m, 2H, assumed; partially obscured by water peak), 1.29 (d, J=6.2 Hz, 3H).

Step 16. Synthesis of tert-butyl [(4S,4aR,6S,8aS)-4-(fluoromethyl)-8a-(2-fluoro-5-{[(2,2,2-trifluoroethyl)amino]methyl}phenyl)-6-methyl-4,4a,5,6,8,8a-hexahydropyrano[3,4-d][1,3]thiazin-2-yl]carbamate (C103)

A solution of 2,2,2-trifluoroethanamine (61 mg, 0.62 mmol) in dichloromethane (0.5 mL) was added to a solution of C102 (135 mg, 0.31 mmol) in dichloromethane (0.5 mL) and the reaction mixture was stirred for 3 hours. Additional 2,2,2-trifluoroethanamine (61 mg, 0.62 mmol) was added, and stirring was continued for 2.5 hours, whereupon acetic acid (2 mL) was added. After 1.5 hours, 2,2,2-trifluoroethanamine (61 mg, 0.62 mmol) was again introduced, followed by sodium triacetoxyborohydride (130 mg, 0.61 mmol). After 12 hours, the reaction mixture was diluted with saturated aqueous sodium bicarbonate solution (3 mL) and extracted three times with ethyl acetate. The combined organic layers were washed with saturated aqueous sodium chloride solution, dried over sodium sulfate, filtered, and concentrated in vacuo. Silica gel chromatography (Gradient: 0% to 30% ethyl acetate in hexanes) provided the product as a white foamy solid. Yield: 146 mg, 0.279 mmol, 90%. $^1$H NMR (500 MHz, CDCl$_3$) δ 7.31-7.35 (m, 1H), 7.21 (br d, J=6.5 Hz, 1H), 7.06 (dd, J=12.2, 8.3 Hz, 1H), 4.53 (ddd, J=47.0, 9.4, 7.7 Hz, 1H), 4.36 (ddd, J=46.3, 9.5, 6.5 Hz, 1H), 4.16 (d, J=11.4 Hz, 1H), 3.88 (s, 2H), 3.71-3.78 (m, 2H), 3.35-3.44 (m, 1H), 3.19 (q, $J_{HF}$=9.4 Hz, 2H), 3.14-3.21 (m, 1H), 1.53 (s, 9H), 1.5-1.67 (m, 2H, assumed; partially obscured by water signal), 1.29 (d, J=6.2 Hz, 3H).

Step 17. Synthesis of (4S,4aR,6S,8aS)-4-(fluoromethyl)-8a-(2-fluoro-5-{[(2,2,2-trifluoroethyl)amino]methyl}phenyl)-6-methyl-4,4a,5,6,8,8a-hexahydropyrano[3,4-d][1,3]thiazin-2-amine (19)

Compound C103 (145 mg, 0.277 mmol) was dissolved in dichloromethane (2 mL) and treated with trifluoroacetic acid (1 mL). After 4 hours, the reaction mixture was quenched with saturated aqueous sodium bicarbonate solution and extracted three times with dichloromethane. The combined organic layers were dried over sodium sulfate, filtered, concentrated in vacuo, and purified by silica gel chromatography (Gradient: 0% to 10% methanol in dichloromethane). The material obtained from chromatography was dissolved in acetonitrile and lyophilized, then subjected to preparative HPLC (Column: Phenomenex Luna C18(2), 15 μm; Mobile phase A: 0.05% trifluoroacetic acid in water; Mobile phase B: 0.05% trifluoroacetic acid in acetonitrile; Gradient: 2% to 90% B). The combined product fractions were neutralized with solid sodium bicarbonate, saturated with solid sodium chloride and extracted three times with ethyl acetate. The combined extracts were dried over sodium sulfate, filtered, concentrated, and lyophilized to afford the product as a white solid. Yield: 31 mg, 73 μmol, 26%. LCMS m/z 424.2 [M+H]$^+$. $^1$H NMR (500 MHz, CDCl$_3$) δ 7.24-7.31 (m, 2H, assumed; partially obscured by solvent peak), 7.04 (dd, J=12.3, 8.3 Hz, 1H), 4.57 (ddd, J=46.6, 9.5, 6.7 Hz, 1H), 4.31-4.46 (m, $J_{HF}$=46.7 Hz, 1H), 4.12 (dd, J=11.4, 2.0 Hz, 1H), 3.84-3.92 (m, 3H), 3.70-3.78 (m, 1H), 3.47-3.56 (m, 1H), 3.18 (q, $J_{HF}$=9.4 Hz, 2H), 3.08-3.14 (m, 1H), 1.44-1.6 (m, 2H, assumed; partially obscured by water peak), 1.28 (d, J=6.2 Hz, 3H).

Example 20

(4S,4aR,6S,8aS)-8a-(2,4-Difluoro-5-{[(2,2,2-trifluoroethyl)amino]methyl}phenyl)-4-(fluoromethyl)-6-methyl-4,4a,5,6,8,8a-hexahydropyrano[3,4-d][1,3]thiazin-2-amine (20)

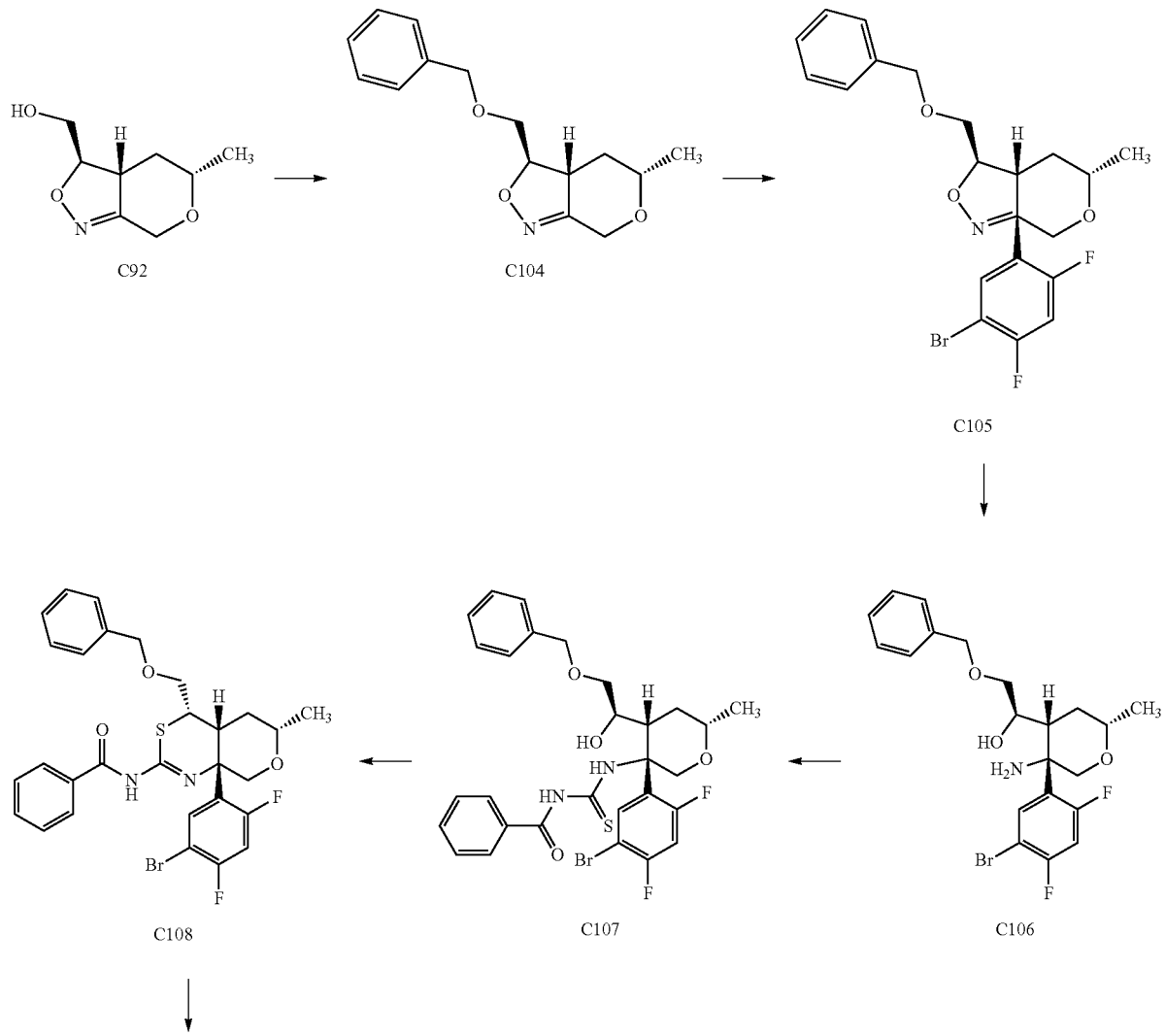

111 112

-continued

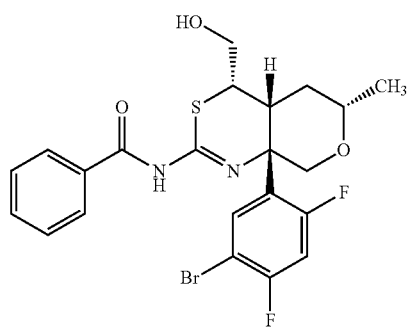

C109

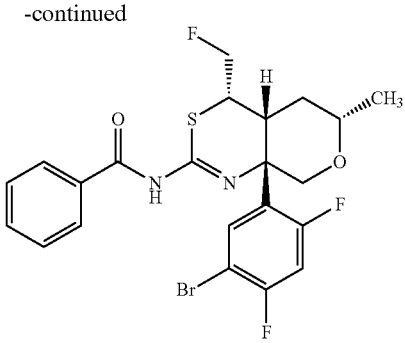

C110

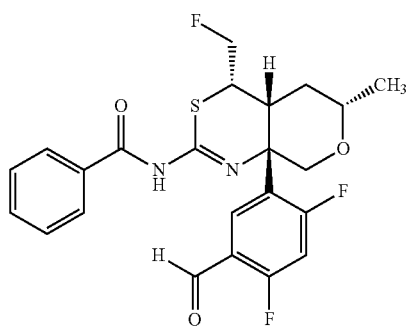

C111

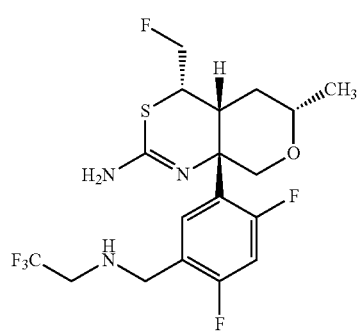

20

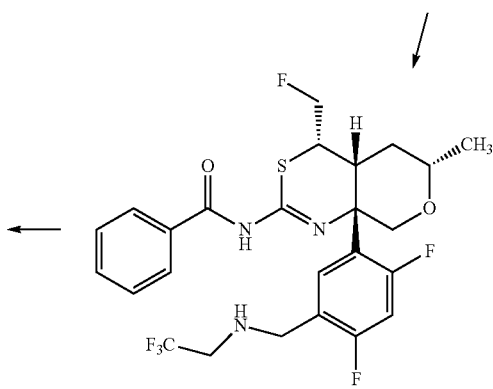

C112

Step 1. Synthesis of (3R,3aR,5S)-3-[(benzyloxy)methyl]-5-methyl-3,3a,4,5-tetrahydro-7H-pyrano[3,4-c][1,2]oxazole (C104)

A solution of C92 (65.7 g, 384 mmol) in tetrahydrofuran (500 mL) was added drop-wise over 25 minutes to a mixture of sodium hydride (60% in oil, 22.9 g, 572 mmol) in tetrahydrofuran (200 mL) that was cooled in an ice/salt/water bath. Additional tetrahydrofuran (200 mL) was used to rinse the addition funnel and facilitate stirring, which was continued under cooling. After 1 hour, benzyl bromide (98.4 g, 575 mmol) was added drop-wise over 15 minutes; at the completion of the addition, the ice bath was removed, then reapplied as needed as the reaction mixture began to exotherm. After 1.5 hours, the reaction was slowly quenched with water (650 mL), then diluted with ethyl acetate (650 mL) and allowed to stand for 18 hours. The aqueous layer was extracted with ethyl acetate (2×350 mL), and the combined organic layers were dried over magnesium sulfate (100 g), filtered, and concentrated in vacuo. Silica gel chromatography (Eluents: heptane, followed by 10%, 20% and 30% ethyl acetate in heptane) provided the product. Yield: 76.4 g, 292 mmol, 76%. LCMS m/z 261.8 [M+H$^+$]. $^1$H NMR (500 MHz, CDCl$_3$) δ 7.3-7.4 (m, 5H), 4.63 (d, J=13.4 Hz, 1H), 4.61 (AB quartet, $J_{AB}$=12.1 Hz, $\Delta v_{AB}$=6.8 Hz, 2H), 4.29 (ddd, J=10.2, 4.8, 4.8 Hz, 1H), 4.15 (dd, J=13.4, 1.2 Hz, 1H), 3.74 (dd, half of ABX pattern, J=10.5, 4.7 Hz, 1H), 3.71 (dd, half of ABX pattern, J=10.6, 4.7 Hz, 1H), 3.54-3.65 (m, 1H), 3.30 (ddd, J=11.1, 10.9, 6.6 Hz, 1H), 2.09 (ddd, J=12.9, 6.6, 1.6 Hz, 1H), 1.49 (ddd, J=12.8, 11.4, 11.4 Hz, 1H), 1.24 (d, J=6.2 Hz, 3H).

Step 2. Synthesis of (3R,3aR,5S,7aS)-3-[(benzyloxy)methyl]-7a-(5-bromo-2,4-difluorophenyl)-5-methyl-hexahydro-1H-pyrano[3,4-c][1,2]oxazole (C105)

Reaction of C104 with 1-bromo-2,4-difluoro-5-iodobenzene was carried out using the method described for synthesis of C29 in Example 10. The product was obtained as a white solid. Yield: 1.31 g, 2.88 mmol, 25%. $^1$H NMR (500 MHz, CDCl$_3$) δ 8.14 (dd, J=8.2, 8.2 Hz, 1H), 7.24-7.33 (m, 3H, assumed; partially obscured by solvent peak), 7.12-7.18 (m, 2H), 6.73 (dd, J=11.2, 8.0 Hz, 1H), 6.31 (s, 1H), 4.30 (AB quartet, J$_{AB}$=12.1 Hz, Δν$_{AB}$=89 Hz, 2H), 4.08 (ddd, J=6.6, 6.1, 1.4 Hz, 1H), 3.88 (dd, J=12.8, 2.0 Hz, 1H), 3.76 (d, J=13 Hz, 1H), 3.60-3.72 (m, 1H), 3.05-3.14 (m, 1H), 3.00 (dd, J=9.9, 6.1 Hz, 1H), 2.75 (dd, J=9.9, 6.7 Hz, 1H), 2.03 (ddd, J=14.2, 7.6, 2.0 Hz, 1H), 1.40-1.53 (m, 1H), 1.24 (d, J=6.2 Hz, 3H).

Step 3. Synthesis of (1R)-1-[(2S,4R,5S)-5-amino-5-(5-bromo-2,4-difluorophenyl)-2-methyltetrahydro-2H-pyran-4-yl]-2-(benzyloxy)ethanol (C106)

Molybdenum hexacarbonyl (1.79 g, 6.78 mmol) was added to a solution of C105 (2.80 g, 6.16 mmol) in acetonitrile (36 mL) and water (3.6 mL), and the reaction mixture was heated at reflux for 30 minutes, then cooled to room temperature. Sodium borohydride (466 mg, 12.3 mmol) was added, and the reaction mixture was heated at reflux for 4 hours, whereupon it was allowed to cool to room temperature, and was then quenched with methanol. The mixture was filtered through diatomaceous earth, and the filter pad was rinsed sequentially with methanol and with ethyl acetate. The filtrate was concentrated in vacuo and then partitioned between ethyl acetate and saturated aqueous sodium bicarbonate solution. The aqueous layer was extracted three times with ethyl acetate, and the combined organic layers were washed with saturated aqueous sodium chloride solution, dried over sodium sulfate, filtered, and concentrated in vacuo. The residue was suspended in dichloromethane (50 mL), treated with aqueous sodium hydroxide solution (1 M, 30 mL) and stirred at room temperature for 1.5 hours. Water (50 mL) was added, and the aqueous layer was extracted with dichloromethane (2×30 mL); the combined organic layers were washed with saturated aqueous sodium chloride solution, dried over sodium sulfate, filtered, and concentrated under reduced pressure. Silica gel chromatography (Gradient: 0% to 60% ethyl acetate in hexanes) afforded the product as a colorless oil. Yield: 2.52 g, 5.52 mmol, 90%. $^1$H NMR (500 MHz, CDCl$_3$) δ 8.00 (dd, J=8.1, 8.1 Hz, 1H), 7.27-7.36 (m, 3H), 7.18-7.24 (m, 2H), 6.76 (dd, J=11.8, 8.1 Hz, 1H), 4.32 (AB quartet, J$_{AB}$=11.9 Hz, Δν$_{AB}$=9.8 Hz, 2H), 3.94 (dd, J=11.4, 1.8 Hz, 1H), 3.58-3.72 (m, 2H), 3.26 (d, J=11.4 Hz, 1H), 3.05-3.15 (m, 2H), 2.73 (ddd, J=12.5, 4.6, 4.6 Hz, 1H), 1.61-1.74 (m, 1H), 1.5-1.61 (m, 1H, assumed; partially obscured by water peak), 1.27 (d, J=6.1 Hz, 3H).

Step 4. Synthesis of N-{[(3S,4R,6S)-4-[(1R)-2-(benzyloxy)-1-hydroxyethyl]-3-(5-bromo-2,4-difluorophenyl)-6-methyltetrahydro-2H-pyran-3-yl]carbamothioyl}benzamide (C107)

Compound C106 was converted to the product according to the method described for synthesis of C97 in Example 19. The product was obtained as a white foam. Yield: 3.07 g, 4.96 mmol, 90%. LCMS m/z 621.3 [M+H$^+$].

Step 5. Synthesis of N-[(4S,4aR,6S,8aS)-4-[(benzyloxy)methyl]-8a-(5-bromo-2,4-difluorophenyl)-6-methyl-4,4a,5,6,8,8a-hexahydropyrano[3,4-d][1,3]thiazin-2-yl]benzamide (C108)

Compound C107 was converted to the product according to the method described for synthesis of C78 in Example 17. The product was isolated as a white foam. Yield: 2.62 g, 4.36 mmol, 88%. LCMS m/z 601.4, 603.1 [M+H$^+$]. $^1$H NMR (500 MHz, CDCl$_3$) δ 8.07-8.31 (m, 2H), 7.48-7.57 (m, 2H), 7.41-7.48 (m, 2H), 7.27-7.39 (m, 5H), 6.95 (dd, J=11.7, 7.8 Hz, 1H), 4.49 (AB quartet, J$_{AB}$=11.9 Hz, Δν$_{AB}$=46.4 Hz, 2H), 4.03-4.11 (m, 1H), 3.77 (d, J=12.0 Hz, 1H), 3.63-3.74 (m, 2H), 3.48 (dd, J=9.1, 7.9 Hz, 1H), 3.35-3.45 (m, 1H), 3.07-3.18 (m, 1H), 1.5-1.64 (m, 1H, assumed; partially obscured by water peak), 1.40-1.49 (m, 1H), 1.23 (d, J=6.1 Hz, 3H).

Step 6. Synthesis of N-[(4S,4aR,6S,8aS)-8a-(5-bromo-2,4-difluorophenyl)-4-(hydroxymethyl)-6-methyl-4,4a,5,6,8,8a-hexahydropyrano[3,4-d][1,3]thiazin-2-yl]benzamide (C109)

Trifluoromethanesulfonic acid (1.2 mL, 14 mmol) was added to a solution of C108 (2.62 g, 4.36 mmol) in dichloromethane (40 mL). The reaction mixture was stirred at room temperature for 2.5 hours, then cooled to 0° C. and basified to pH 12 with 1 M aqueous sodium hydroxide solution. The resulting solution was partitioned between water (50 mL) and dichloromethane (50 mL), and the aqueous layer was extracted with dichloromethane (2×30 mL); the combined organic layers were washed with saturated aqueous sodium chloride solution (30 mL), dried over sodium sulfate, filtered, and concentrated in vacuo. Trituration with 20% ethyl acetate in hexanes provided the product as a white solid. Yield: 2.10 g, 4.11 mmol, 94%. LCMS m/z 511.1 [M+H$^+$]. $^1$H NMR (500 MHz, CDCl$_3$) δ 8.20 (br s, 2H), 7.50-7.59 (m, 2H), 7.42-7.49 (m, 2H), 6.95 (dd, J=11.7, 7.8 Hz, 1H), 4.05-4.17 (m, 1H), 3.66-3.92 (m, 5H), 3.26-3.39 (m, 1H), 3.09-3.26 (m, 1H), 1.60-1.68 (m, 2H), 1.27 (d, J=6.2 Hz, 3H).

Step 7. Synthesis of N-[(4S,4aR,6S,8aS)-8a-(5-bromo-2,4-difluorophenyl)-4-(fluoromethyl)-6-methyl-4,4a,5,6,8,8a-hexahydropyrano[3,4-d][1,3]thiazin-2-yl]benzamide (C110)

To a suspension of C109 (500 mg, 0.98 mmol) in dichloromethane (10 mL) at −78° C. was added (diethylamino)sulfur trifluoride (0.14 mL, 1.1 mmol), and the reaction mixture was allowed to stir at −78° C. for 10 minutes before being allowed to warm to room temperature. After 2 hours at room temperature, the reaction was quenched with saturated aqueous sodium bicarbonate solution, diluted with water, and extracted with dichloromethane (3×50 mL). The combined organic layers were washed with saturated aqueous sodium chloride solution (50 mL), dried over sodium sulfate, filtered, and concentrated in vacuo. Silica gel chromatography (Gradient: 0% to 30% ethyl acetate in hexanes) afforded the product as a colorless oil/foam. Yield: 123 mg, 0.240 mmol, 24%. $^1$H NMR (300 MHz, CDCl$_3$) δ 8.02-8.32 (m, 2H), 7.42-7.61 (m, 4H), 6.98 (dd, J=11.7, 7.8 Hz, 1H), 4.58 (ddd, J=47, 9.4, 8.0 Hz, 1H), 4.43 (ddd, J=46, 9.5, 6.3 Hz, 1H), 4.11 (br d, J=12.6 Hz, 1H), 3.80 (d, J=12.0 Hz, 1H), 3.67-3.85 (m, 1H), 3.39-3.58 (m, 1H), 3.10-3.25 (m, 1H), 1.6-1.71 (m, 2H, assumed; partially obscured by solvent peak), 1.29 (d, J=6.2 Hz, 3H).

Step 8. Synthesis of N-[(4S,4aR,6S,8aS)-8a-(2,4-difluoro-5-formylphenyl)-4-(fluoromethyl)-6-methyl-4,4a,5,6,8,8a-hexahydropyrano[3,4-d][1,3]thiazin-2-yl]benzamide (C111)

Compound C110 was converted to the product using the method described for synthesis of C102 in Example 19. The product was obtained as a colorless oil. Yield: 23 mg, 50 μmol, 21%. Also isolated was unreacted C110 (17 mg, 33 μmol). C111: LCMS m/z 463.1 [M+H]$^+$. $^1$H NMR (300 MHz, CDCl$_3$) δ 10.24 (s, 1H), 8.12 (br d, J=7.3 Hz, 2H), 7.90 (dd, J=8.7, 7.9 Hz, 1H), 7.52-7.61 (m, 1H), 7.41-7.52 (m, 2H), 7.01 (dd, J=11.8, 9.6 Hz, 1H), 4.58 (ddd, J=47, 9.4, 8.2 Hz, 1H), 4.41 (ddd, J=46, 9.5, 6.2 Hz, 1H), 4.03-4.13 (m, 1H), 3.82 (d, J=11.8 Hz, 1H), 3.69-3.88 (m, 1H), 3.35-3.54 (m, 1H), 3.10-3.26 (m, 1H), 1.55-1.72 (m, 2H, assumed; partially obscured by water peak), 1.29 (d, J=6.1 Hz, 3H).

Step 9. Synthesis of N-[(4S,4aR,6S,8aS)-8a-(2,4-difluoro-5-{[(2,2,2-trifluoroethyl)amino]methyl}phenyl)-4-(fluoromethyl)-6-methyl-4,4a,5,6,8,8a-hexahydropyrano[3,4-d][1,3]thiazin-2-yl]benzamide (C112)

To a solution of C111 (22 mg, 48 μmol) in dichloromethane (0.5 mL) was added 2,2,2-trifluoroethanamine (23 μL, 0.29 mmol), followed by sodium triacetoxyborohydride (21 mg, 99 μmol), and the reaction flask was sealed and stirred at room temperature for 18 hours. After being quenched with saturated aqueous sodium bicarbonate solution (3 mL), the reaction mixture was diluted with water (20 mL) and extracted with dichloromethane (3×10 mL). The combined organic layers were washed with saturated aqueous sodium chloride solution, dried over sodium sulfate, filtered, and concentrated in vacuo. Silica gel chromatography (Gradient: 0% to 50% ethyl acetate in hexanes) afforded the product as a colorless oil. Yield: 16 mg, 29 μmol, 60%. LCMS m/z 546.2 [M+H]$^+$. $^1$H NMR (500 MHz, CDCl$_3$) δ 8.15-8.25 (m, 2H), 7.53 (br t, J=7.3 Hz, 1H), 7.46 (br dd, J=7.7, 7.3 Hz, 2H), 7.37 (dd, J=8.4, 8.4 Hz, 1H), 6.89 (dd, J=11.9, 9.2 Hz, 1H), 4.58 (ddd, J=46.9, 9.4, 7.8 Hz, 1H), 4.42 (ddd, J=46.2, 9.5, 6.5 Hz, 1H), 4.11-4.16 (m, 1H), 3.84-3.95 (m, 2H), 3.71-3.83 (m, 2H), 3.43-3.56 (m, 1H), 3.10-3.27 (m, 3H), 1.6-1.74 (m, 2H, assumed; partially obscured by solvent peak), 1.29 (d, J=6.1 Hz, 3H).

Step 10. Synthesis of (4S,4aR,6S,8aS)-8a-(2,4-difluoro-5-{[(2,2,2-trifluoroethyl)amino]methyl}phenyl)-4-(fluoromethyl)-6-methyl-4,4a,5,6,8,8a-hexahydropyrano[3,4-d][1,3]thiazin-2-amine (20)

A mixture of C112 (16 mg, 29 μmol), pyridine (24 μL, 0.30 mmol) and methoxylamine hydrochloride (24.5 mg, 0.29 mmol) in ethanol (1 mL) was heated at 50° C. for 15 hours. The reaction mixture was allowed to cool to room temperature, whereupon it was concentrated in vacuo; the residue was purified via preparative HPLC (Column: Phenomenex Luna C18(2), 15 μm; Mobile phase A: 0.05% trifluoroacetic acid in water; Mobile phase B: 0.05% trifluoroacetic acid in acetonitrile; Gradient: 2% to 90% B). The fractions containing product were pooled, neutralized with solid sodium bicarbonate, saturated with solid sodium chloride, and extracted three times with ethyl acetate. The combined organic layers were dried over sodium sulfate, filtered, and concentrated under reduced pressure; the residue was dissolved in acetonitrile and lyophilized to afford the product as a white solid. Yield: 7.4 mg, 17 μmol, 59%. APCI m/z 442.3 [M+H]$^+$. $^1$H NMR (500 MHz, CDCl$_3$) δ 7.37 (br dd, J=8.6, 8.5 Hz, 1H), 6.84 (dd, J=11.9, 9.3 Hz, 1H), 4.59 (ddd, J=46.9, 9.5, 6.6 Hz, 1H), 4.35-4.49 (m, 1H), 4.04 (dd, J=11.6, 1.8 Hz, 1H), 3.88-3.97 (m, 3H), 3.69-3.77 (m, 1H), 3.51-3.60 (m, 1H), 3.07-3.25 (m, 3H), 1.45-1.6 (m, 2H, assumed; partially obscured by solvent peak), 1.29 (d, J=6.2 Hz, 3H).

Biological Assays

BACE1 Cell-Free Assay:
Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 μM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 μL assay buffer (100 mM sodium acetate, pH 4.5 (brought to pH with acetic acid), and 0.001% Tween-20). Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

Whole Cell Assay (In Vitro sAPPb Assay):
H4 human neuroglioma cells over-expressing the wild-type human APP$_{695}$ are treated for 18 hours with compound in cell growth media having a final concentration 1% DMSO. sAPPβ levels are measured using either TMB-ELISA or Pierce SuperSignal ELISA Pico Chemiluminescent Substrate (Pierce 37069) with capture APP N-terminal antibody (Affinity BioReagents, OMA1-03132), wild-type sAPPβ specific reporter p192 (Elan), and tertiary anti rabbit-HRP (GE Healthcare).

BACE2 Assay:
This assay measures the inhibition of the BACE2 enzyme as it cleaves a non-native peptide. A synthetic substrate that can be cleaved by BACE2 having N-terminal biotin and made fluorescent by the covalent attachment of Oregon Green at the Cys residue is used to assay BACE2 activity in the presence or absence of the inhibitory compounds. The substrate is Biotin-KEISEISYEVEFR-C(Oregon green)-KK-OH. The BACE2 enzyme is available from Enzo Life Sciences (Cat # BML-SE550). Compounds are incubated in a ½ log dose response curve from a top concentration of 100 μM with BACE2 enzyme and the biotinylated fluorescent peptide in 384-well black plates (Thermo Scientific #4318). BACE2 is at a final concentration of 2.5 nM with a final concentration of peptide substrate of 150 nM in a reaction volume of 30 μL assay buffer (100 mM sodium acetate, pH 4.5 (brought to pH with acetic acid), and 0.001% Tween-20). Plates are covered and incubated for 3 hours at 37° C. The reaction is stopped with the addition of 30 μL of 1.5 μM Streptavidin (Pierce, #21125). After a 10 minute incubation at room temperature, plates are read on a Perkin Elmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of BACE2 enzymatic cleavage of the synthetic substrate.

TABLE 1

| | Biological Data | | |
|---|---|---|---|
| Example # | BACE1 Cell-free Assay IC$_{50}$ (μM)[a] | sAPPβ Whole-Cell Assay IC$_{50}$ (nM)[a] | BACE2 Cell-free Assay IC$_{50}$ (μM) |
| 1 | 1.22 | 53.5 | N.D.[c] |
| 2 | 0.445 | 74.0 | 2.80[a] |
| 3 | 5.55 | 393 | N.D. |
| 4 | 0.854 | 93.0 | 2.52[b] |
| 5 | 0.320 | 46.5 | N.D. |
| 6 | 2.33 | 195 | N.D. |
| 7 | 1.78 | 119 | N.D. |
| 8 | 0.076 | 5.9 | N.D. |
| 9 | 0.076 | 8.94 | N.D. |
| 10 | 0.064 | 10.9 | N.D. |
| 11 | 0.107 | 12.1 | N.D. |
| 12 | 0.060 | 6.43 | N.D. |
| 13 | 0.342 | 47.6 | N.D. |
| 14 | 0.967 | 49.6 | N.D. |
| 15 | 0.376 | 8.05 | 0.423[d] |
| 16 | 0.019 | 1.88 | 0.108[d] |
| 17 | 0.082 | 11.4[d] | N.D. |
| 18 | 0.036 | 0.545 | 0.020[d] |
| 19 | 0.150 | 30.4 | N.D. |
| 20 | 0.068 | 35.7 | N.D. |

[a]Reported IC$_{50}$ values are the geometric mean of 2-3 determinations.
[b]IC$_{50}$ value is from a single determination.
[c]"N.D." means "no data".
[d]Reported IC$_{50}$ value is the geometric mean of 4-7 determinations.

We claim:

1. A compound of Formula I,

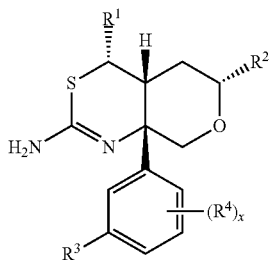

wherein

R$^1$ is hydrogen or methyl, wherein said methyl is optionally substituted with one to three substituents independently selected from halogen or methoxy;

R$^2$ is C$_{1-6}$ alkyl, —(C(R$^5$)$_2$)$_m$—(C$_{3-6}$ cycloalkyl), —C(R$^5$)$_2$)$_m$—(C$_{6-10}$ aryl), —(C(R$^5$)$_2$)$_m$— (5- to 10-membered heteroaryl) or —(C(R$^5$)$_2$)$_t$—OR$^6$; wherein said alkyl, cycloalkyl, aryl or heteroaryl moieties are optionally substituted with one to three substituents independently selected from halogen, C$_{1-6}$ alkyl, —CH$_2$F, —CHF$_2$, —CF$_3$, —CN or —OR$^7$;

R$^3$ is —C(R$^5$)$_2$)$_m$—(CN);

R$^4$ is independently selected from halogen, C$_{1-6}$ alkyl or C$_{1-6}$ alkoxy; wherein said alkyl or alkoxy is optionally substituted with one to three fluoro;

R$^5$ at each occurrence is independently selected from hydrogen or C$_{1-3}$ alkyl, wherein said alkyl is optionally substituted with one to three halogen;

R$^6$ is hydrogen, C$_{1-6}$ alkyl or —(C(R$^5$)$_2$)$_n$—(C$_{6-10}$ aryl), wherein said alkyl and aryl are optionally substituted with one to three substituents independently selected from halogen, C$_{1-3}$ alkyl, —CH$_2$F, —CHF$_2$, —CF$_3$, —CN or —OH;

R$^7$ for each occurrence is hydrogen or C$_{1-6}$ alkyl, wherein said alkyl is optionally substituted with one to three substituents independently selected from halogen or C$_{1-6}$ alkoxy;

m at each occurrence is independently 0, 1 or 2;

n at each occurrence is independently is 1 or 2;

t is 1 or 2; and x is 0, 1, 2 or 3;

or a tautomer thereof or a pharmaceutically acceptable salt of said compound or tautomer.

2. The compound of claim 1 wherein m is 0 or 1; and R$^5$ at each occurrence is hydrogen; or a tautomer thereof or a pharmaceutically acceptable salt of said compound or tautomer.

3. The compound of claim 1 wherein m is 0; R$^2$ is C$_{1-6}$ alkyl optionally substituted with one to three fluoro, or —(C(R$^5$)$_2$)$_t$—OR$^6$; wherein t is 1; R$^5$ at each occurrence is hydrogen, and R$^6$ is C$_{1-3}$ alkyl optionally substituted with one to three fluoro, or —(C(R$^5$)$_2$)$_n$—(C$_{6-10}$ aryl), wherein said aryl is optionally substituted with one to three substituents selected from halogen, C$_{1-6}$ alkyl, —CH$_2$F, —CHF$_2$, —CF$_3$, —CN or —OH; or a tautomer thereof or a pharmaceutically acceptable salt of said compound or tautomer.

4. The compound of claim 3 wherein R$^6$ is —(C(R$^5$)$_2$)$_n$—(C$_{6-10}$ aryl), said aryl is phenyl optionally substituted with one to three substituents independently selected from halogen, C$_{1-6}$ alkyl, —CH$_2$F, —CHF$_2$, —CF$_3$, —CN or —OH; n is 1; and R$^5$ at each occurrence is hydrogen; or a tautomer thereof or a pharmaceutically acceptable salt of said compound or tautomer.

5. The compound of claim 1 wherein R$^2$ is —(C(R$^5$)$_2$)$_m$—(C$_{3-6}$ cycloalkyl) or —(C(R$^5$)$_2$)$_m$-(5- to 10-membered heteroaryl), wherein said cycloalkyl or heteroaryl is optionally substituted with one to three substituents independently selected from halogen, C$_{1-6}$ alkyl, —CH$_2$F, —CHF$_2$, and —CF$_3$ m is 0; and R$^5$ at each occurrence is hydrogen; or a tautomer thereof or a pharmaceutically acceptable salt of said compound or tautomer.

6. The compound of claim 1 wherein R$^4$ is independently selected from fluoro, chloro, methyl, ethyl, propyl, methoxy or ethoxy; wherein said methyl, ethyl and propyl groups are optionally substituted with one to three fluoro; and x is 0, 1 or 2; or a tautomer thereof or a pharmaceutically acceptable salt of said compound or tautomer.

7. A compound of claim 1 of Formula Ia,

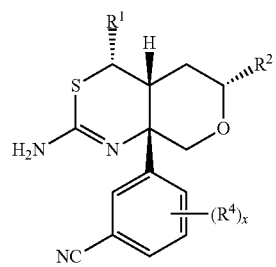

wherein

R$^1$ is hydrogen or methyl, wherein said methyl is optionally substituted with one to three halogen;

R$^2$ is C$_{1-6}$ alkyl, —(C(R$^5$)$_2$)$_m$—(C$_{3-6}$ cycloalkyl), —(C(R$^5$)$_2$)$_m$-(5- to 10-membered heteroaryl) or —(C(R$^5$)$_2$)$_t$—OR$^6$; wherein said alkyl, cycloalkyl or heteroaryl moieties are optionally substituted with one to three substituents independently selected from halogen, C$_{1-6}$ alkyl, —CH$_2$F, —CHF$_2$, —CF$_3$, —CN or —OH;

R⁴ is independently halogen, C₁₋₆ alkyl or C₁₋₆ alkoxy; wherein said alkyl or alkoxy moieties are optionally substituted with one to three fluoro;

R⁵ at each occurrence is hydrogen or C₁₋₃ alkyl, wherein said alkyl is optionally substituted with one to three halogen;

R⁶ is hydrogen, C₁₋₆ alkyl or —(C(R⁵)₂)ₙ—(C₆₋₁₀ aryl), wherein said alkyl and aryl are optionally substituted with one to three substituents selected from halogen, C₁₋₃ alkyl, —CH₂F, —CHF₂, —CF₃, —CN or —OH;

m is 0, 1 or 2;

n is 1 or 2;

t is 1 or 2; and x is 0, 1 or 2 or 3;

or a tautomer thereof or a pharmaceutically acceptable salt of said compound or tautomer.

8. The compound of claim 7 wherein R⁴ is independently selected from fluoro, chloro, methyl, ethyl, propyl, methoxy and ethoxy, wherein said methyl, ethyl and propyl groups are optionally substituted with one to three fluoro; and x is 0, 1 or 2; or a tautomer thereof or a pharmaceutically acceptable salt of said compound or tautomer.

9. The compound of claim 8 wherein R² is methyl, optionally substituted with one to three fluoro; R⁴ is independently selected from methoxy, chloro or fluoro; and x is 0, 1 or 2; or a tautomer thereof or a pharmaceutically acceptable salt of said compound or tautomer.

10. The compound of claim 8 wherein R² is —(C(R⁵)₂)ₘ-(5-membered heteroaryl); R⁴ is independently methoxy, chloro or fluoro; m is 0; and x is 0, 1 or 2; or a tautomer thereof or a pharmaceutically acceptable salt of said compound or tautomer.

11. The compound of claim 8 wherein R² is —(C(R⁵)₂)ₜ—OR⁶;

R⁶ is hydrogen, methyl or —(C(R⁵)₂)ₙ—(C₆₋₁₀ aryl), wherein the aryl of R⁶ is phenyl optionally substituted with one to three substituents selected from halogen, C₁₋₃ alkyl, —CH₂F, —CHF₂, —CF₃, —CN or —OH;

R⁴ is independently methoxy, chloro or fluoro;

x is 0, 1 or 2;

n is 1; and t is 1;

or a tautomer thereof or a pharmaceutically acceptable salt of said compound or tautomer.

12. The compound of claim 8 wherein R² is —(C(R⁵)₂)ₘ—(C₃₋₆ cycloalkyl), wherein said cycloalkyl is optionally substituted with one to three substituents selected from halogen or C₁₋₆ alkyl, optionally substituted with one to three fluoro;

R⁴ is independently methoxy, chloro or fluoro;

m is 0 or 1; and x is 0, 1 or 2;

or a tautomer thereof or a pharmaceutically acceptable salt of said compound or tautomer.

13. The compound according to claim 1, or a tautomer thereof or a pharmaceutically acceptable salt of said compound or tautomer;

wherein

R¹ is hydrogen or methyl;

R² is methyl, fluoromethyl, hydroxymethyl, methoxymethyl, benzyloxymethyl, cyclopropyl, 3-methyl-1,2-oxazol-5-yl, 4-methyl-1,3-oxazol-2-yl or 1-methyl-1H-pyrazol-4-yl;

R³ is —CN;

R⁴ is independently fluoro, chloro or methoxy; and x is 0, 1 or 2.

14. The compound according to claim 13 selected from the group consisting of

5-[(4aR,6R,8aS)-2-Amino-6-[(benzyloxy)methyl]-4,4a,5,6-tetrahydropyrano[3,4-d][1,3]thiazin-8a(8H)-yl]-4-fluoro-2-methoxybenzonitrile;

5-[(4aR,6R,8aS)-2-Amino-6-[(benzyloxy)methyl]-4,4a,5,6-tetrahydropyrano[3,4-d][1,3]thiazin-8a(8H)-yl]-2,4-difluorobenzonitrile;

5-[(4aR,6R,8aS)-2-Amino-6-(hydroxymethyl)-4,4a,5,6-tetrahydropyrano[3,4-d][1,3]thiazin-8a(8H)-yl]-2,4-difluorobenzonitrile;

5-[(4aR,6R,8aS)-2-Amino-6-(fluoromethyl)-4,4a,5,6-tetrahydropyrano[3,4-d][1,3]thiazin-8a(8H)-yl]-2,4-difluorobenzonitrile;

5-[(4aR,6R,8aS)-2-Amino-6-(methoxymethyl)-4,4a,5,6-tetrahydropyrano[3,4-d][1,3]thiazin-8a(8H)-yl]-2,4-difluorobenzonitrile;

3-[(4aR,6S,8aS)-2-Amino-6-methyl-4,4a,5,6-tetrahydropyrano[3,4-d][1,3]thiazin-8a(8H)-yl]-4-chlorobenzonitrile;

3-[(4aR,6S,8aS)-2-Amino-6-methyl-4,4a,5,6-tetrahydropyrano[3,4-d][1,3]thiazin-8a(8H)-yl]benzonitrile;

3-[(4aR,6R,8aS)-2-Amino-6-(3-methyl-1,2-oxazol-5-yl)-4,4a,5,6-tetrahydropyrano[3,4-d][1,3]thiazin-8a(8H)-yl]-4-fluorobenzonitrile;

3-[(4aR,6R,8aS)-2-Amino-6-(4-methyl-1,3-oxazol-2-yl)-4,4a,5,6-tetrahydropyrano[3,4-d][1,3]thiazin-8a(8H)-yl]-4-fluorobenzonitrile;

3-[(4aR,6R,8aS)-2-Amino-6-(1-methyl-1H-pyrazol-4-yl)-4,4a,5,6-tetrahydropyrano[3,4-d][1,3]thiazin-8a(8H)-yl]-4-fluorobenzonitrile;

3-[(4aR,6R,8aS)-2-Amino-6-cyclopropyl-4,4a,5,6-tetrahydropyrano[3,4-d][1,3]thiazin-8a(8H)-yl]-4-fluorobenzonitrile;

3-[(4aR,6S,8aS)-2-Amino-6-methyl-4,4a,5,6-tetrahydropyrano[3,4-d][1,3]thiazin-8a(8H)-yl]-4-fluorobenzonitrile; and 3-[(4R,4aR,6R,8aS)-2-Amino-4-methyl-6-(3-methyl-1,2-oxazol-5-yl)-4,4a,5,6-tetrahydropyrano[3,4-d][1,3]thiazin-8a(8H)-yl]-4-fluorobenzonitrile;

or a tautomer thereof or a pharmaceutically acceptable salt of said compound or tautomer.

15. A pharmaceutical composition comprising a therapeutically effective amount of the compound of claim 1, or a tautomer thereof or a pharmaceutically acceptable salt of said compound or tautomer, and a pharmaceutically acceptable vehicle, diluent or carrier.

16. A method of treating insulin resistance, impaired glucose intolerance, Type 2 diabetes, obesity, or hypertension in a patient, the method comprising administering a therapeutically effective amount of a compound according to claim 1, or a tautomer thereof or a pharmaceutically acceptable salt of said compound or tautomer to a patient in need of treatment thereof.

17. A compound selected from the group consisting of

3-[(4aR,6R,8aS)-2-Amino-6-(3-methyl-1,2-oxazol-5-yl)-4,4a,5,6-tetrahydropyrano[3,4-d][1,3]thiazin-8a(8H)-yl]-4-fluorobenzonitrile;

3-[(4aR,6R,8aS)-2-Amino-6-(4-methyl-1,3-oxazol-2-yl)-4,4a,5,6-tetrahydropyrano[3,4-d][1,3]thiazin-8a(8H)-yl]-4-fluorobenzonitrile;

3-[(4aR,6R,8aS)-2-Amino-6-(1-methyl-1H-pyrazol-4-yl)-4,4a,5,6-tetrahydropyrano[3,4-d][1,3]thiazin-8a(8H)-yl]-4-fluorobenzonitrile;

3-[(4aR,6R,8aS)-2-Amino-6-cyclopropyl-4,4a,5,6-tetrahydropyrano[3,4-d][1,3]thiazin-8a(8H)-yl]-4-fluorobenzonitrile; and 3-[(4aR,6S,8aS)-2-Amino-6-methyl-4,4a,5,6-tetrahydropyrano[3,4-d][1,3]thiazin-8a(8H)-yl]-4-fluorobenzonitrile;

or a tautomer thereof or a pharmaceutically acceptable salt of said compound or tautomer.

\* \* \* \* \*